US009803005B2

(12) United States Patent
Hunter et al.

(10) Patent No.: US 9,803,005 B2
(45) Date of Patent: Oct. 31, 2017

(54) HUMANEERED ANTI-FACTOR B ANTIBODY

(71) Applicant: Alexion Pharmaceuticals, Inc., Cheshire, CT (US)

(72) Inventors: Jeffrey W. Hunter, New Britain, CT (US); Douglas L. Sheridan, Branford, CT (US)

(73) Assignee: Alexion Pharmaceuticals, Inc., New Haven, CT (US)

( * ) Notice: Subject to any disclaimer, the term of this patent is extended or adjusted under 35 U.S.C. 154(b) by 299 days.

(21) Appl. No.: 14/402,031

(22) PCT Filed: May 20, 2013

(86) PCT No.: PCT/US2013/041811
§ 371 (c)(1),
(2) Date: Nov. 18, 2014

(87) PCT Pub. No.: WO2013/177035
PCT Pub. Date: Nov. 28, 2013

(65) Prior Publication Data
US 2015/0166643 A1 Jun. 18, 2015

Related U.S. Application Data

(60) Provisional application No. 61/651,472, filed on May 24, 2012.

(51) Int. Cl.
*A61K 39/395* (2006.01)
*C07K 16/18* (2006.01)

(52) U.S. Cl.
CPC .......... *C07K 16/18* (2013.01); *C07K 2317/41* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,845,083 A | 7/1989 | Fortin et al. | |
| 4,883,784 A | 11/1989 | Kaneko | |
| 5,679,546 A | 10/1997 | Ko et al. | |
| 5,714,350 A | 2/1998 | Co et al. | |
| 5,869,615 A | 2/1999 | Hourcade et al. | |
| 5,976,540 A | 11/1999 | Rittershaus et al. | |
| 6,165,463 A | 12/2000 | Platz et al. | |
| 6,248,365 B1 | 6/2001 | Romisch et al. | |
| 6,458,360 B1 | 10/2002 | Fearon et al. | |
| 6,521,450 B1 | 2/2003 | Atkinson et al. | |
| 6,820,011 B2 | 11/2004 | Chen et al. | |
| 6,897,290 B1 | 5/2005 | Atkinson et al. | |
| 7,759,304 B2 | 7/2010 | Gilkeson et al. | |
| 7,964,105 B2 | 6/2011 | Moss | |
| 7,964,705 B2 | 6/2011 | Emlen et al. | |
| 7,999,082 B2 | 8/2011 | Holers et al. | |
| 8,007,804 B2 | 8/2011 | Tomlinson et al. | |
| 8,652,475 B2 | 2/2014 | Holers et al. | |
| 8,703,140 B2 | 4/2014 | Holers et al. | |
| 8,911,733 B2 | 12/2014 | Holers et al. | |
| 2002/0015701 A1 | 2/2002 | Gupta-Bansal et al. | |
| 2002/0081293 A1 | 6/2002 | Fung et al. | |
| 2003/0198636 A1 | 10/2003 | Gupta-Bansal et al. | |
| 2003/0235582 A1 | 12/2003 | Singh et al. | |
| 2004/0005538 A1 | 1/2004 | Chen et al. | |
| 2004/0014782 A1 | 1/2004 | Krause | |
| 2005/0107319 A1 | 5/2005 | Bansal | |
| 2005/0169915 A1 | 8/2005 | Do Couto et al. | |
| 2005/0255552 A1 | 11/2005 | Flynn et al. | |
| 2005/0260198 A1 | 11/2005 | Holers et al. | |
| 2006/0002944 A1 | 1/2006 | Ashkenazi et al. | |
| 2006/0134098 A1 | 6/2006 | Bebbington et al. | |
| 2006/0178308 A1 | 8/2006 | Schwaeble et al. | |
| 2006/0263819 A1 | 11/2006 | Hageman et al. | |
| 2006/0292141 A1 | 12/2006 | Holers et al. | |
| 2007/0020647 A1 | 1/2007 | Hageman et al. | |
| 2007/0065433 A1 | 3/2007 | Mollnes et al. | |
| 2007/0183970 A1 | 8/2007 | Goldenberg et al. | |

(Continued)

FOREIGN PATENT DOCUMENTS

CA 1340879 A 1/2000
WO WO-99/42133 A1 8/1999

(Continued)

OTHER PUBLICATIONS

Rudikoff et al., Proc Natl Acad Sci USA 79: 1979-1983 (1982).*
Colman, Research in Immunology 145: 33-36 (1994).*
Kussie et al., J. Immunol. 152: 146-152 (1994).*
Chen et al., EMBO J., 14: 2784-2794 (1995).*
Adair et al., J. Nat'l. Med. Assoc. 69: 715-717 (1977).*
Abe et al., "Contribution of anaphylatoxin C5a to late airway responses after repeated exposure of antigen to allergic rats," J Immunol. 167(8):4651-60 (2001).
Abbas, et al., Lymphocyte Specificity and Activation, *Cellular and Molecular Immunology*. W.B. Saunders Company, 54 (1991).
Abrahamsen et al., "Differential mediator release from basophils of allergic and non-allergic asthmatic patients after stimulation with anti-IgE and C5a," Clin Exp Allergy. 31(3):368-78 (2001).
Alexander et al., "Complement-dependent apoptosis and inflammatory gene changes in murine lupus cerebritis," J Immunol. 175(12):8312-8319 (2005).

(Continued)

*Primary Examiner* — Phillip Gambel
(74) *Attorney, Agent, or Firm* — Clark & Elbing LLP

(57) ABSTRACT

This invention relates to humaneered anti-factor B antibodies and antigen-binding fragments thereof with modified glycosylation patterns. The humaneered anti-factor B antibodies and antigen-binding fragments thereof are derived from murine monoclonal antibody 1379, which binds factor B in the third short consensus repeat ("SCR") domain and selectively inhibits activation of the alternative complement pathway by preventing formation of the C3bBb complex. The invention also relates to methods of treating diseases or disorders in which activation of the alternative complement pathway plays a role, and methods of selectively inhibiting activation of the alternative complement pathway in an individual in need thereof.

18 Claims, 25 Drawing Sheets

(56) References Cited

U.S. PATENT DOCUMENTS

| | | |
|---|---|---|
| 2008/0075720 A1 | 3/2008 | Holers et al. |
| 2008/0102040 A1 | 5/2008 | Holers et al. |
| 2008/0267980 A1 | 10/2008 | Tomlinson et al. |
| 2008/0299114 A1 | 12/2008 | Emlen et al. |
| 2009/0123469 A1 | 5/2009 | Campagne et al. |
| 2009/0136936 A1* | 5/2009 | Georgiou .............. C07K 16/00 435/6.16 |
| 2009/0175847 A1 | 7/2009 | Barghorn et al. |
| 2011/0163412 A1 | 7/2011 | Park |
| 2011/0318337 A1 | 12/2011 | Emlen et al. |
| 2012/0171206 A1 | 7/2012 | Tomlinson et al. |
| 2013/0029912 A1 | 1/2013 | Holers et al. |

FOREIGN PATENT DOCUMENTS

| | | |
|---|---|---|
| WO | WO-00/21559 A2 | 4/2000 |
| WO | WO-01/47963 A2 | 7/2001 |
| WO | WO-2004/022096 A1 | 3/2004 |
| WO | WO-2004/031240 A1 | 4/2004 |
| WO | WO-2004/103288 A2 | 12/2004 |
| WO | WO-2004/106369 A2 | 12/2004 |
| WO | WO-2005/003159 A1 | 1/2005 |
| WO | WO-2005/016455 A2 | 2/2005 |
| WO | WO-2005/023195 A2 | 3/2005 |
| WO | WO-2005/069970 A2 | 8/2005 |
| WO | WO-2005/077417 A1 | 8/2005 |
| WO | WO-2006/012621 A2 | 2/2006 |
| WO | WO-2006/055178 A2 | 5/2006 |
| WO | WO-2006/062716 A2 | 6/2006 |
| WO | WO-2006/083533 A2 | 8/2006 |
| WO | WO-2006/122257 A2 | 11/2006 |
| WO | WO-2007/011363 A2 | 1/2007 |
| WO | WO-2007/029008 A2 | 3/2007 |
| WO | WO-2007/032876 A2 | 3/2007 |
| WO | WO-2007/034210 A2 | 3/2007 |
| WO | WO-2007/056227 A2 | 5/2007 |
| WO | WO-2007/109747 A2 | 9/2007 |
| WO | WO-2008/140653 A2 | 11/2008 |
| WO | WO-2009/061910 A1 | 5/2009 |
| WO | WO-2011/057158 A1 | 5/2011 |
| WO | WO-2011/143637 A1 | 11/2011 |
| WO | WO-2011/163412 A1 | 12/2011 |
| WO | WO-2013/177035 A2 | 11/2013 |

OTHER PUBLICATIONS

Anderson et al., "Activation of complement pathways after contusion-induced spinal cord injury," J Neurotrauma. 21(12):1831-46 (2004).

"Monoclonal antibody to human factor B (Bb), Catalog No. A227," Quidel Corporation Product Catalog, <http://www.quidel.com/products/product_detail.php?group=2&prod=83>, retrieved on Aug. 4, 2008 (2 pages).

Attwood, "The babel of bioinformatics," Science. 290(5491):471-3 (2000).

Barnum, "Inhibition of complement as a therapeutic approach in inflammatory central nervous system (CNS) disease," Mol Med. 5(9):569-82 (1999).

Becherer et al., "Segment spanning residues 727-768 of the complement C3 sequence contains a neoantigenic site and accommodates the binding of CR1, Factor H, and factor B," Biochemistry. 31(6):1787-94 (1992).

Bellander et al., "Activation of the complement cascade and increase of clusterin in the brain following a cortical contusion in the adult rat," J Neurosurg. 85(3):468-75 (1996).

Bellander et al., "Complement activation in the human brain after traumatic head injury," J Neurotrauma. 18(12):1295-311 (2001).

Bendayan, "Possibilities of false Immunocytochemical results generated by the use of monoclonal antibodies: The example of the anti-proinsulin antibody," J Histochem Cytochem. 43:881-886 (1995).

Bendig, "Humanization of rodent monoclonal antibodies by CDR grafting," Methods: A Companion to Methods in Enzymology. 8:83-93 (1995).

Beste et al., "Small antibody-like proteins with prescribed ligand specificities derived from the lipocalin fold," Proc Natl Acad Sci USA. 96(5):1898-903 (1999).

Bjornson et al., "Complement is activated in the upper respiratory tract during influenza virus infection," Am Rev Respir Dis. 143(5 Pt 1):1062-6 (1991).

Blease et al., "Chemokines and their role in airway hyper-reactivity," Respir Res. 1(1):54-61 (2000).

Boos et al., "Murine complement C4 Is not required for experimental autoimmune encephalomyelitis," Glia. 49(1):158-60 (2004).

Bost et al., "Antibodies against a peptide sequence within the HIV envelope protein crossreacts with human interleukin-2," Immunol Invest. 17:577-586 (1988).

Brandis, "Acid-Base Physiology," <http://www.anaesthesiamcq.com/AcidBaseBook/ab4_4.php>, retrieved on Sep. 19, 2011 (2 pages).

Caldas et al., "Humanization of the anti-CD18 antibody 6.7: An unexpected effect of a framework residue in binding to antigen," Mol Immunol. 39(15):941-52 (2003).

Casale et al., "Direct evidence of a role for mast cells in the pathogenesis of antigen-induced bronchoconstriction," J Clin Invest. 80(5):1507-11 (1987).

Casarsa et al., "Intracerebroventricular injection of the terminal complement complex causes inflammatory reaction in the rat brain," Eur J Immunol. 33(5):1260-70 (2003).

Chaney, "Corticosteroids and cardiopulmonary bypass: A review of clinical investigations," CHEST. 121(3):921-31 (2002).

Chàrdes et al., "Efficient amplification and direct sequencing of mouse variable regions from any immunoglobulin gene Family," FEBS Lett. 452(3):386-94 (1999).

Chien et al., "Significant structural and functional change of an antigen-binding site by a distant amino acid substitution: proposal of a structural mechanism," Proc Natl Acad Sci USA. 86:5532-5536 (1989).

Choi et al., "Inhalation delivery of proteins from ethanol suspensions," Proc Natl Acad Sci. 98(20):11103-11107 (2001).

Clardy et al., "In vitro inhibition of complement activation using a monoclonal antibody (McAb) directed against human Factor B (FB)," Pediatric Res. Abstract No. 1969 31:331 A (1992).

Clark, "Antibodies for therapeutic applications," <http://www.path.cam.ac.uk/~mrc7/humanisation/antibodies.html>, retrieved Jun. 1, 2002 (5 pages).

Cole et al., "Beyond lysis: how complement influences cell fate," Clin Sci (Lond). 104(5):455-66 (2003).

Cole et al., "Complement regulator loss on apoptotic neuronal cells causes increased complement activation and promotes both phagocytosis and cell lysis," Mol Immunol. 43(12):1953-64 (2006).

Collard et al., "Complement activation following oxidative stress," Mol Immunol. 36(13-14):941-8 (1999).

Roberts et al., "Effect of intravenous corticosteroids on death within 14 days in 10008 adults with clinically significant head injury (MRC CRASH trial): Randomised placebo-controlled trial," Lancet. 364(9442):1321-8 (2004).

Czermak et al., "Complement, cytokines, and adhesion molecule expression in inflammatory reactions," Proc Assoc Am Physicians. 110(5):306-312 (1998).

Daha et al., "Stabilization of the amplification convertase of complement by monoclonal antibodies directed against human factor B," J Immun. 132(5):2538-42 (1984).

De Broe et al., "Pathophysiology of hemodialysis-associated hypoxemia," Adv Nephrol Necker Hosp. 18:297-315, Abstract Only (1989).

Desai et al., "Demonstration of C5 cleaving activity in bronchoalveolar fluids and cells: A mechanism of acute and chronic alveolitis," J Exp Pathol. 1(3):201-216 (1984).

Diaz et al., "Leukocytes and mediators in bronchoalveolar lavage during allergen-induced late-phase asthmatic reactions," Am Rev Respir Dis. 139(6):1383-9 (1989).

Drouin et al., "A protective role for the fifth complement component (C5) in allergic airway disease," Am J Respir Crit Care Med. 173 (8):852-7 (2006).

(56) References Cited

OTHER PUBLICATIONS

Drouin et al., "Expression of the complement anaphylatoxin C3a and C5a receptors on bronchial epithelial and smooth muscle cells in models of sepsis and asthma," J Immunol. 166(3):2025-32 (2001).
Dutton et al., "Traumatic Brain Injury," Curr Opin Crit Care. 9:503-9 (2003).
Eldadah et al., "Caspase pathways, neuronal apoptosis, and CNS injury," J Neurotrauma 17(10):811-29 (2000).
Elf et al., "Prevention of secondary insults in neurointensive care of traumatic brain injury," Eur J of Trauma. 29:74-80 (2003).
Elward et al., "CD46 plays a key role in tailoring innate immune recognition of apoptotic and necrotic cells," J Biol Chem. 280(43):36342-54 (2005).
Farkas et al., "A neuronal C5a receptor and an associated apoptotic signal transduction pathway," J Physiol. 507(Pt 3):679-87 (1998).
Felderhoff-Mueser et al., "Pathways leading to apoptotic neurodegeneration following trauma to the developing rat brain," Neurobiol Dis. 11(2):231-45 (2002).
Figueroa et al., "Infectious diseases associated with complement deficiencies," Clin Microbiol Rev. 4(3):359-95 (1991).
Frank, "Complement: A brief review," J Allergy Clin Immunol. 84 (4 Pt 1):411-20 (1989).
Friedlander, "Apoptosis and caspases in neurodegenerative diseases," N Engl J Med. 348(14):1365-75 (2003).
Gerard et al., "Complement in allergy and asthma," Curr Opin Immunol. 14:705-708 (2002).
German et al., "Systemic complement depletion inhibits experimental cerebral vasospasm," Neurosurgery. 39(1):141-5, discussion 145-6, Abstract Only (1996).
Ghajar, "Traumatic brain injury," Lancet. 356:923-929 (2000).
Gilkeson, "Role of complement factor B in the pathogenesis of SLE, Project No. 5R01 AI047469-05," <http://projectreporter.nih.gov/pr_Prj_info_desc_dtls.cfm?icde=0&aid=6712799&print=yes>, retrieved on Apr. 25, 2011 (2 pages).
Girardi et al., "Complement C5a receptors and neutrophils mediate fetal injury in the Antiphospholipid Syndrome," J Clin Invest. Corrigendum. 113(4):646 (2004).
Giusti, et al. "Somatic diversification of S107 from an antiphosphocholine to an anti-DNA autoantibody is due to a single base change in its heavy chain variable region," Proc Natl Acad Sci USA. 84(9):2926-30 (1987).
Glovsky, et al., "Complement determinations in human disease," Ann Allergy, Asthma Immunol. 93(6):513-523 (2004).
Glovsky et al., "Is complement activation a factor in bronchial asthma?" Int Arch Allergy Immunol. 118(2-4):330-2 (1999).
Gönczi et al., "The severity of clinical symptoms in ragweed-allergic patients is related to the extent of ragweed-induced complement activation in their sera," Allergy. 52(11):1110-4 (1997).
Hall, "Cooperative Interaction of Factor B and other complement components with mononuclear cells in the antibody-independent lysis of xenogeneic erythrocytes," J Exp Med. 156(3):834-43 (1982).
Hawlisch et al., "The anaphylatoxins bridge innate and adaptive immune responses in allergic asthma," Mol Immunol. 41(1-2):123-31 (2004).
Hicks et al., "Vaccinia virus complement control protein enhances functional recovery after traumatic brain injury," J. Neurotrauma. 19(6):705-14 (2002).
Hogaboam et al., "Mannose-binding lectin deficiency alters the development of fungal asthma: Effects on airway response, inflammation, and cytokine profile," J Leukoc Biol. 75(5):805-14 (2004).
Holers et al., "The alternative pathway of complement in disease: Opportunities for therapeutic targeting," Mol. Immunol. 41:147-152 (2004).
Holers, "The complement system as a therapeutic target in autoimmunity," Clin Immunol. 107(3):140-51 (2003).
Holers, "Phenotypes of complement knockouts," Immunopharmacology. 49(1-2):125-31 (2000).
Holgate et al., "The bronchial epithelium as a key regulator of airway inflammation and remodelling in asthma," Clin Exp Allergy. 29 Suppl 2:90-5 (1999).
Holm et al., "Functional mapping and single chain construction of the anti-cytokeratin 8 monoclonal antibody TS1," Mol Immunol. 44(6):1075-1084 (2007).
Höpken et al., "The C5a chemoattractant receptor mediates mucosal defence to infection," Nature. 383(6595):86-9 (1996).
Humbles et al., "A role for the C3a anaphylatoxin receptor in the effector phase of asthma," Nature 406(6799):998-1001 (2000).
Irvin et al., "Airways hyperreactivity and inflammation produced by aerosolization of human C5A des arg," Am Rev Respir Dis. 134(4):777-83 (1986).
Jaeschke et al., "Role of neutrophils in acute inflammatory liver injury," Liver Int. 26(8):912-9 (2006).
Jagels et al., "C3a and C5a enhance granulocyte adhesion to endothelial and epithelial cell monolayers: Epithelial and endothelial priming is required for C3a-induced eosinophil adhesion," Immunopharmacology. 46(3):209-22 (2000).
Kaczorowski et al., "Effect of Soluble Complement Receptor-1 on Neutrophil Accumulation After Traumatic Brain Injury in Rats," J Cereb Blood Flow Metab. 15(5):860-4 (1995).
Kang et al., "A novel anti-human Factor B monoclonal antibody inhibits Factor D-mediated associate and cleavage of Factor B," Abstract No. 191, Immunopharmacology. 49:68 (2000).
Karp et al., "Identification of complement factor 5 as a susceptibility locus for experimental allergic asthma," Nat Immunol. 1(3):221-226 (2000).
Kasamatsu et al., "Experimental acute lung injury in guinea pigs after aerosol challenge with sonicated Pseudomonas aeruginosa whole cells," Arerugi 42(10):1616-1622 (1993) English translation of abstract only.
Kodani et al., "Intratracheal administration of anaphylatoxin C5a potentiates antigen-induced pulmonary reactions through the prolonged production of cysteinyl-leukotrienes," Immunopharmacology. 49(3):263-74 (2000).
Köhl et al., "A regulatory role for the C5a anaphylatoxin in type 2 immunity in asthma," J Clin Invest. 116(3):783-796 (2006).
Kolb et al., "Ba and Bb fragments of factor B activation: Fragment production, biological activities, neoepitope expression and quantitation in clinical samples," Complement Inflamm. 6(3):175-204 (1989).
Kossmann et al., "Elevated levels of the complement components C3 and factor B in ventricular cerebrospinal fluid of patients with traumatic brain injury," J Neuroimmunol. 73(1-2):63-9 (1997).
Krug et al., "Complement factors C3a and C5a are increased in bronchoalveolar lavage fluid after segmental allergen provocation in subjects with asthma," Am J Respir Crit Care Med. 164(10 Pt 1):1841-3 (2001).
Kulik et al., "Pathogenic natural antibodies recognizing Annexin IV are required to develop intestinal ischaemia-reperfusion injury and are selected during development in a CR2/CD21-dependent manner," Mol. Immunology. 45:4110, Abstract 045 (2008).
Kulkarni et al., "Neuroprotection from complement-mediated inflammatory damage," Ann N Y Acad Sci. 1035:147-164 (2004).
Kurucz et al., "Current animal models of bronchial asthma," Curr Pharm Des. 12(25):3175-3194 (2006).
Kuttner-Kondo et al., "Characterization of the active sites in decay-accelerating factor," J Immunol. 167(4):2164-2171 (2001).
Kyrkanides et al., "Enhanced glial activation and expression of specific CNS inflammation-related molecules in aged versus young rats following cortical stab injury," J Neuroimmunol. 119(2):269-77 (2001).
Lambrecht, "An unexpected role for the anaphylatoxin C5a receptor in allergic sensitization," J Clin Invest. 116(3):628-632 (2006).
Larsen et al., "A differential effect of C5a and C5a des Arg in the induction of pulmonary inflammation," Am J Pathol. 100(1):179-92 (1980).
Lederman et al., "A single amino acid substitution in a common African allele of the CD4 molecule ablates binding of the monoclonal antibody, OKT4," Mol Immunol. 28(11):1171-1181 (1991).
Leinhase et al., "Pharmacological complement inhibition at the C3 convertase level promotes neuronal survival, neuroprotective

(56) References Cited

OTHER PUBLICATIONS intracerebral gene expression, and neurological outcome after traumatic brain injury," Exp. Neurol. 199(2):454-64 (2006).
Leinhase et al., "Reduced neuronal cell death after experimental brain injury in mice lacking a functional alternative pathway of complement activation," BMC Neurosci. 7:55 (2006).
Lemanske, "Asthma therapies revisited: what have we learned?" Proc Am Thorac Soc. 6(3):312-5 (2009).
Leslie et al., "Complement Receptors," Encylopedia of Life Sciences, Nature Publishing Group. (2001) (9 pages).
Li et al., "beta-Endorphin omission analogs: Dissociation of immunoreactivity from other biological activities." Proc Natl Acad Sci USA. 77(6):3211-3214 (1980).
Lukacs et al., "Complement-dependent immune complex-induced bronchial inflammation and hyperreactivity," Am J Physiol Lung Cell Mol Physiol. 280(3):L512-8 (2001).
MacCallum et al., "Antibody-antigen interactions: Contact analysis and binding site topography." J Mol Biol. 262(5):732-45 (1996).
Marciano et al., "Neuron-specific mRNA complexity responses during hippocampal apoptosis after traumatic brain injury," J Neurosci. 24(12):2866-76 (2004).
Mariuzza et al., "The structural basis of antigen-antibody recognition," Annu Rev Biophys Chem. 16:139-159 (1987).
Marshall et al., "A new classification of head injury based on computerized tomography," J Neurosurg. 75:S14-S20 (1991).
Maruo et al., "Generation of anaphylatoxins through proteolytic processing of C3 and C5 by house dust mite protease," J Allergy Clin Immunol. 100(2):253-260 (1997).
Matis et al., "Complement-specific antibodies: designing novel anti-inflammatories," Nat Med. 1(8):839-842 (1995).
Matsumoto et al., "Abrogation of the alternative complement pathway by targeted deletion of murine factor B," Proc Natl Acad Sci USA. 94(16):8720-8725 (1997).
Maulik et al., "Molecular biotechnology: therapeutic applications and strategies," Wiley-Liss, Inc., pp. v-viii (Table of Contents Only).
McArthur et al., "Moderate and severe traumatic brain injury: epidemiologic, imaging and neuropathologic perspectives," Brain Pathol. 14(2):185-94 (2004).
Mohamad et al., "Mitochondrial apoptotic pathways," Biocell. 29(2):149-161 (2005).
Morgan et al., "Expression of complement in the brain: Role in health and disease," Immunol Today. 17(10):461-466 (1996).
Morgan, "Regulation of the complement membrane attack pathway," Crit Rev Immunol. 19(3):173-198 (1999).
Mukherjee et al., "Allergic asthma: Influence of genetic and environmental factors," J Biol Chem. 286(38):32883-9 (2011).
Nagata et al., "Activation of human serum complement with allergens," J Allergy Clin Immunol. 80(1):24-32 (1987).
Nagy et al., "The development of asthma in children infected with Chlamydia pneumoniae is dependent on the modifying effect of mannose-binding lectin," J Allergy Clin Immunol. 112(4):729-734 (2003).
Nataf et al., "Attenuation of experimental autoimmune demyelination in complement-deficient mice," J Immunol. 165(10):5867-5873 (2000).
Nataf et al., "Complement anaphylatoxin receptors on neurons: New tricks for old receptors?" Trends Neurosci. 22(9):397-402 (1999).
O'Barr et al., "Neuronal expression of a functional receptor for the C5a complement activation fragment," J Immunol. 166(6):4154-4162 (2001).
Ohlsson et al., "Complement activation after lumbosacral ventral root avulsion injury," Neurosci Lett. 394(3):179-183 (2006).
Ohlsson et al., "Complement activation following optic nerve crush in the adult rat," J Neurotrauma. 20(9):895-904 (2003).
Padlan et al., "Structure of an antibody-antigen complex: crystal structure of the HyHEL-10 Fab-lysozyme complex," Proc Natl Acad Sci USA. 86(15):5938-5942 (1989).
Peng et al.,"Blocking intrapulmonary activation of complement cascade on the development of airway hyperresponsiveness: Utility in sight?" Late-breaking abstracts presented at scientific sessions AAAAI 62nd annual meeting, Mar. 3-7, Abstract LB2:720 (2006).
Peng et al.,"Contribution of complement component C5 in the development of airway inflammation, maintaining airway hyperresponsiveness and sustaining an ongoing asthmatic attack," Mol Immunol. 41:292 Abstract 200 (2004).
Peng et al., "Role of C5 in the development of airway inflammation, airway hyperresponsiveness, and ongoing airway response," J. Clin. Invest. 115(6):1590-1600(2005).
Peters et al., "The Bb fragment of complement factor B acts as a B cell growth factor." J Exp Med. 169(4):1225-1235 (1988).
Pillay et al., "Administration of vaccinia virus complement control protein shows significant cognitive improvement in a mild injury model," Ann N Y Acad Sci. 1056:450-61(2005).
Qiu et al., "Upregulation of the fas receptor death-inducing signaling complex after traumatic brain injury in mice and humans," J Neurosci. 22(9):3504-11(2002).
Rader et al., "A phage display approach for rapid antibody humanization: Designed combinatorial V gene libraries," Proc Natl Sci USA. 95(15):8910-5 (1998).
Ramer et al., "Setting the stage for functional repair of spinal cord injuries: A cast of thousands," Spinal Cord. 43(3):134-61(2005).
Rancan et al., "Central nervous system-targeted complement inhibition mediates neuroprotection after closed head injury in transgenic mice," J Cereb Blood Flow Metab. 23(9):1070-74 (2003).
Raghupathi et al., "BCL-2 overexpression attenuates cortical cell loss after traumatic brain injury in transgenic mice," J Cereb Blood Flow Metab. 18(11):1259-69 (1998).
Raghupathi, "Cell death mechanisms following traumatic brain injury," Brain Pathol. 14(2):215-22 (2004).
Raghupathi et al., "Mild traumatic brain injury induces apoptotic cell death in the cortex that is preceded by decreases in cellular Bcl-2 immunoreactivity," Neuroscience. 110(4):605-616(2002).
Raghupathi et al., "Temporal alterations in cellular bax: Bcl-2 ratio following traumatic brain injury in the rat," J Neurotrauma. 20(5):421-35 (2003).
Rebhun et al., "Proteins of the complement system and acute phase reactants in sera of patients with spinal cord injury," Ann Allergy. 66(4):335-8 (1991).
Reynolds et al., "Vaccinia Virus Complement Control Protein Reduces Inflammation and Improves Spinal Cord Integrity Following Spinal Cord Injury," Ann. NY. Acad Sci. 1035:165-178(2004).
Rink et al., "Evidence of apoptotic cell death after experimental traumatic brain injury in the rat," Am. J. Pathol. 147(6):1575-1583(1995).
Robbins et al., "Complement activation by cigarette smoke," Am J. Physiol. 260(4 Pt 1):L254-9 (1991).
Rood et al., "Reduction of early graft loss after intraportal porcine islet transplantation in monkeys," Transplantation. 83(2):202-210 (2007) Abstract Only.
Roof et al., "Gender differences in acute CNS trauma and stroke: Neuroprotective effects of estrogen and progesterone," J Neurotrauma. 17(5):367-388(2000).
Rounioja et al., "Mechanism of acute fetal cardiovascular depression after maternal inflammatory challenge in mouse," Am J Pathol. 166(6):1585-1592 (2005).
Royo et al., "Pharmacology of traumatic brain injury," Curr Opin Pharmacol. 3(1):27-32 (2003).
Rudikoff et al., "Single amino acid substitution altering antigen-binding specificity," Proc Natl Acad Sci USA. 79(6):1979-1983 (1982).
Sauerland et al., "A CRASH landing in severe head injury," Lancet. 364(9442):1291-1292 (2004).
Sambrook et al., Analysis of genomic DNA by Southern hybridization. *Molecular Cloning: A Laboratory Manual*. Second Edition, Cold Spring Harbor Labs Press: Cold Spring Harbor, NY, pp. 9.31-9.62(1989).
Schmidt et al., "Closed head injury—an inflammatory disease?," Brain Res. Rev. 48(2):388-399(2005).
Schmidt et al., "The role of neuroinflammation in traumatic brain injury," Eur. J. Trauma. 3:135-149(2004).

(56) References Cited

OTHER PUBLICATIONS

Schreiber et al.,"Complement anaphylatoxin C5a and C5a receptor are fundamental to neutrophil activation and glomerulonephritis induced by anti-neutrophil cytoplasmic antibodies," Mol Immunol. 45:4109 Abstract No. 042 (2008).
Shacka et al., "Regulation of neuronal cell death and neurodegeneration by members of the Bcl-2 family: Therapeutic implications," Curr Drug Targets CNS Neurol Disord. 4(1):25-39 (2005).
Sinha et al., "The receptor for complement anaphylatoxin C5a protects against the development of airway hyperresponsiveness in allergic asthma by inhibiting cysteinyl leukotriene pathway," Mol Immunol. 45:4109-4110 Abstract No. 043 (2008).
Skolnick et al., "From genes to protein structure and function: novel applications of computational approaches in the genomic era," Trends Niotechnol. 18(1):34-39 (2000).
Stahel et al., "Experimental closed head injury: Analysis of neurological outcome, blood-brain barrier dysfunction, intracranial neutrophil infiltration, and neuronal cell death in mice deficient in genes for pro-inflammatory cytokines," J Cereb Blood Flow Metab. 20:369-380(2000).
Stahel et al., "Intracerebral complement C5a receptor (CD88) expression is regulated by TNF and lymphotoxin-α following closed head injury in mice," J Neuroimmunol. 109(2):164-72 (2000).
Stahel et al., "Intrathecal levels of complement-derived soluble membrane attack complex (sC5b-9) correlate with blood-brain barrier dysfunction in patients with traumatic brain injury," J. Neurotrauma. 18(8): 773-781(2001).
Strauss et al., "Common patterns of Bcl-2 family gene expression in two traumatic brain injury models," Neurotox. Res. 6(4):333-42 (2004).
Stribling et al., "Aerosol gene delivery in vivo," Proc. Natl. Acad. Sci. USA. 89(23):11277-81(1992).
Takafuji et al., "Degranulation from human eosinophils stimulated with C3a and C5a," Int Arch Allergy Immunol. 104 Suppl 1 (1):27-9 (1994).
Takahashi et al., "Solubilization of antigen-antibody complexes: a new function of complement as a regulator of immune reactions," Prog Allergy. 27:134-166 (1980).
Tanaka et al., "Murine monoclonal anti-Ba antibody that enhances haemolytic activity of Factor B," Immunology. 73(4):383-387(1991).
Tatusova et al., "BLAST 2 Sequences, a new tool for comparing protein and nucleotide sequences," FEMS Microbiol Lett. 174(2):247-250 (1999).
Taube et al., "Factor B of the alternative complement pathway regulates development of airway hyperresponsiveness and inflammation," Proc Natl Acad Sci USA. 103(21):8084-8089 (2006).
Taube et al., "Inhibition of complement activation decreases airway inflammation and hyperresponsiveness," Am J Respir Crit Care Med. 168(11):1333-41 (2003).
Teasdale et al., "Assessment of coma and impaired consciousness," Lancet. 2(7872):81-4 (1974).
Thurman et al., "Acute tubular necrosis is characterized by activation of the alternative pathway of complement," Kidney Int. 67(2):524-30 (2005).
Thurman et al., "The central role of the alternative complement pathway in human disease," J Immunol. 176(3):1305-1310 (2006).
Thurman et al., "Complement activation through the alternative pathway is necessary for the development of airway hyperresponsiveness (AHR) and inflammation in a model of human asthma," Mol Immunol., 41:319, Abstract No. 256.
Thurman et al., "A novel inhibitor of the alternative pathway of complement protects mice from ischemic acute renal failure," American Nephrology Society Meeting, Abstract (1 page).
Thurman et al., "Treatment with an inhibitory monoclonal antibody to mouse factor B protects mice from induction of apoptosis and renal ischemia/reperfusion injury," J Am Soc Nephrol. 17(3):707-715 (2006).
Van Beek et al., "Activation of the complement in the central nervous system: Roles in neurodegeneration and neuroprotection," Ann NY Acad Sci. 992:56-71(2003).
Varsano et al., "Generation of complement C3 and expression of cell membrane complement inhibitory proteins by human bronchial epithelium cell line," Thorax. 55(5):364-369 (2000).
Vos et al., "EFNS guideline on mild traumatic brain injury: report of an EFNS task force," Eur J Neurol. 9(3):207-19(2002).
Wang et al., "Anti-C5 monoclonal antibody therapy prevents collagen-induced arthritis and ameoliorates established disease," Proc Natl Acad Sci USA. 92(19):8955-9 (1995).
Watanabe et al., "Modulation of renal disease in MRL/lpr mice genetically deficient in the alternative complement pathway factor B," J Immunol. 164(2):786-794 (2000).
Williams et al., "In situ DNA fragmentation occurs in white matter up to 12 months after head injury in man," Acta Neuropathol. 102(6):581-90 (2001).
Winkelstein et al., "The role of C3 as an opsonin in the early stages of infection," Proc Soc Exp Biol Med. 149(2):397-401 (1975).
Wong et al., "Apoptosis and traumatic brain injury," Neurocrit Care. 3:177-182 (2005).
Xiong et al., "Formation of complement membrane attack complex in mammalian cerebral cortex evokes seizures and neurodegeneration," J Neurosci. 23(3):955-60 (2003).
Yakovlev et al., "Activation of CPP32-like caspases contributes to neuronal apoptosis and neurological dysfunction after traumatic brain injury," J Neurosci. 17(19):7415-24 (1997).
Yao et al., "Progesterone differentially regulates pro- and anti-apoptotic gene expression in cerebral cortex following traumatic brain injury in rats," J Neurotrauma. 22(6):656-68 (2005).
Yatsiv et al., "Elevated intracranial IL-18 in humans and mice after traumatic brain injury and evidence of neuroprotective effects of IL-18-binding protein after experimental closed head injury," J Cereb Blood Flow Metab. 22(8):971-8 (2002).
Yatsiv et al., "Erythropoietin is neuroprotective, improves functional recovery, and reduces neuronal apoptosis and inflammation in a rodent model of experimental closed head injury," FASEB J. 19(12):1701-3 (2005).
Younger et al., "Detrimental effects of complement activation in hemorrhagic shock," J Appl Physiol. 90(2):441-446 (2001).
Zhang et al., "Bench-to-bedside review: Apoptosis/programmed cell death triggered by traumatic brain injury," Crit Care. 9(1):66-75 (2005).
Declaration of Joshua M. Thurman for U.S. Appl. No. 11/057,047, executed Apr. 16, 2008 (3 pages).
Declaration of Vernon Michael Holers for U.S. Appl. No. 11/057,047, executed Aug. 31, 2009 (68 pages).
Extended European Search Report for European Patent Application No. 10188613.3, dated May 31, 2011 (10 pages).
International Search Report for PCT Application No. PCT/US2008/003381, dated Feb. 11, 2009 (3 pages).
International Search Report for PCT Application No. PCT/US06/020460, dated Aug. 29, 2006 (3 pages).
International Search Report for PCT Application No. PCT/US05/04346, dated Jul. 7, 2005 (2 pages).
Supplementary Partial European Search Report for European Application No. 05722948.6, dated Jun. 24, 2008 (6 pages).
Supplementary European Search Report for European Application No. 06771303, dated Oct. 28, 2011 (5 pages).
Cieslewicz et al., "The late, but not early, asthmatic response is dependent on IL-5 and correlates with eosinophil infiltration," J. Clin Invest. 104(3): 301-8 (1999).
Thurman et al., "A novel inhibitor of the alternative complement pathway prevents antiphospholipid antibody-induced pregnancy loss in mice," Mol Immunol. 42(1):87-97 (2005).
Chen et al., "An experimental model of closed head injury in mice: pathophysiology, histopathology, and cognitive deficits," J Neurotrauma 13(10): 557-68 (1996).
Clardy, "Complement activation by whole endotoxin is blocked by a monoclonal antibody to factor B," Infect Immun. 62(10):4549-4555, 1994.
Gaetz, "The neurophysiology of brain injury," Clin Neurophysiol. 115(1):4-18 (2004).

(56) References Cited

OTHER PUBLICATIONS

Hourcade et al., "Analysis of the short consensus repeats of human complement factor B by site-directed mutagenesis," J. Biol. Chem. 270(34): 19716-19722, 1995.
Hourcade et al., "Mutations of the type A domain of complement factor B that promote high-affinity C3b-binding," J. Immunol. 162(5): 2906-11 (1999).
International Search Report for International Application No. PCT/US06/20460, mailed on Aug. 29, 2006 (3 pages).
Keeling et al., "Local neutrophil influx following lateral fluid-percussion brain injury in rats is associated with accumulation of complement activation fragments of the third component (C3) of the complement system," J Neuroimmunol. 105(1):20-30 (2000).
Langlois et al., "Complement activation occurs through both classical and alternative pathways prior to onset and resolution of adult respiratory distress syndrome," Clin Immunol Immunopathol. 47(2): 152-63 (1988).
Thurman et al., "Lack of functional alternative complement pathway ameliorates ischemic acute renal failure in mice," J Immunol. 170: 1517-1523, 2003.
Ueda et al., "Probing functional sites on complement protein B with monoclonal antibodies,"J Immunol. 138(4): 1143-9 (1987).
Versey et al., "Activation of complement in relation to disease," J Clin Pathol (Assoc Clin Pathol). 6: 38-44 (1975).
Clark, "Antibody humanisation for therapeutic applications," <http://www.path.cam.ac.uk/~mrc7/humanisation/index.html>, printed Jun. 1, 2002 (4 pages).
Sewell et al., "Complement C3 and C5 play critical roles in traumatic brain cryoinjury: blocking effects on neutrophil extravasation by C5a receptor antagonist," J. Neuroimmunol. 155(1-2): 55-63 (2004).
Singhrao et al., "Spontaneous classical pathway activation and deficiency of membrane regulators render human neurons susceptible to complement lysis," Am J Pathol. 157(3): 905-18 (2000).
Stahel et al., "The role of the complement system in traumatic brain injury," Brain Res Rev. 27(3): 243-56 (1998).
International Search Report for International Application No. PCT/US2008/003381, dated on Feb. 11, 2009 (3 pages).
International Search Report for International Application No. PCT/US05/04346, mailed on Jul. 7, 2005 (2 pages).
"Monoclonal antibody to human factor B (Ba), Catalog No. A225," Quidel Corporation Product Catalog, <http://www.quidel.com/products/product_detail.php?group=2&prod=82>, retrieved on Aug. 4, 2008 (2 pages).
Xu et al.,"Contribution of the complement control protein modules of C2 in C4b binding assessed by analysis of C2/factor B chimeras," J Immunol. 158(12): 5958-65 (1997).
Girardi et al.,"Complement C5a receptors and neutrophils mediate fetal injury in the Antiphospholipid Syndrome," J Clin Invest. 112(11):1644-54 (2003).
Pardridge, "The blood-brain barrier and neurotherapeutics," NueroRx. 2(1):1-2 (2005).
May, "The Quest for an Acute Traumatic Brain Injury Treatment: Why Progesterone Could Be on Track to Become the First FDA-Approved Therapy," <www.news-medical.net>, retrieved on Feb. 10, 2014 (7 pages).
International Search Report and Written Opinion for International Patent Applciation No. PCT/US2013/041811, dated Nov. 12, 2013 (8 pages).
Internation Premilimary Report on Patentability for Internation Patent Application No. PCT/US2013/041811, dated Nov. 25, 2014 (6 pages).
Co et al., "Genetically engineered deglycosylation of the variable domain increases the affinity of an anti-CD33 monoclonal antibody," Mol Immunol. 30(15):1361-7 (1993).
Filpula, "Antibody engineering and modification technologies," Biomol Eng. 24(2):201-15 (2007).
Leung et al., "Construction and characterization of a humanized, internalizing, B-cell (CD22)-specific, leukemia/lymphoma antibody, LL2," Mol Immunol. 32(17-18):1413-27 (1995).
Leung et al., "Effect of VK framework-1 glycosylation on the binding affinity of lymphoma-specific murine and chimeric LL2 antibodies and its potential use as a novel conjugation site," Int J Cancer 60(4):534-8 (1995).
Wright et al., "Effect of glycosylation on antibody function: implications for genetic engineering," Trends Biotechnol. 15(1):26-32 (1997).
Israel et al., "Increased clearance of IgG in mice that lack beta 2-microglobulin: possible protective role of FcRn," Immunology. 89(4):573-8 (1996).
Mimura et al., "Role of oligosaccharide residues of IgG1-Fc in Fc gamma RIIb binding," J Biol Chem. 276(49):45539-47 (2001).
Newkirk et al., "Differential clearance of glycoforms of IgG in normal and autoimmune-prone mice," Clin Exp Immunol. 106(2):259-64 (1996).
Raju, "Glycosylation variations with expression systems and their impact on biological activity of therapeutic immunoglobulins," BioProcess International. 1(4):44-53 (2003).
Shields et al., "Lack of fucose on human IgG1 N-linked oligosaccharide improves binding to human Fcgamma RIII and antibody-dependent cellular toxicity," J Biol Chem. 277(30):26733-40 (2002).

\* cited by examiner

SEQUENCE LISTING

<160> NUMBER OF SEQ ID NOS: 15

<210> SEQ ID NO 1
<211> LENGTH: 113
<212> TYPE: PRT
<213> ORGANISM: Artificial Sequence
<220> FEATURE:
<223> OTHER INFORMATION: Synthetic Construct

<400> SEQUENCE: 1

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Ser Thr Ser Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Val Tyr Asn Leu Pro Trp Thr Phe Gly Gln Gly Thr Lys Leu Glu Ile
                100                 105                 110

Lys

<210> SEQ ID NO 2
<211> LENGTH: 113
<212> TYPE: PRT

<213> ORGANISM: Artificial Sequence
<220> FEATURE:
<223> OTHER INFORMATION: Synthetic Construct

<400> SEQUENCE: 2

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Gln Ser
            20                  25                  30

Ser Thr Ser Lys Asn Tyr Leu Ala Trp Tyr Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Val Tyr Asn Leu Pro Trp Thr Phe Gly Gln Gly Thr Lys Leu Glu Ile
            100                 105                 110

Lys

<210> SEQ ID NO 3
<211> LENGTH: 113
<212> TYPE: PRT
<213> ORGANISM: Artificial Sequence
<220> FEATURE:
<223> OTHER INFORMATION: Synthetic Construct

<400> SEQUENCE: 3

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Ala Thr Ser Lys Asn Tyr Leu Ala Trp Tyr Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Val Tyr Asn Leu Pro Trp Thr Phe Gly Gln Gly Thr Lys Leu Glu Ile
            100                 105                 110

Lys

<210> SEQ ID NO 4
<211> LENGTH: 120
<212> TYPE: PRT
<213> ORGANISM: Artificial Sequence
<220> FEATURE:
<223> OTHER INFORMATION: Synthetic Construct

<400> SEQUENCE: 4

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Tyr Met Thr Trp Val Arg Gln Ala Pro Gly Gln Gly Leu Glu Trp Met

```
                35                  40                  45
Gly Trp Ile Asn Pro Asn Ser Gly Gly Thr Lys Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Tyr Tyr Ala Asn Ser Ala Trp Phe Ala Tyr Trp Gly Gln
            100                 105                 110

Gly Thr Leu Val Thr Val Ser Ser
        115                 120

<210> SEQ ID NO 5
<211> LENGTH: 120
<212> TYPE: PRT
<213> ORGANISM: Artificial Sequence
<220> FEATURE:
<223> OTHER INFORMATION: Synthetic Construct

<400> SEQUENCE: 5

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
                20                  25                  30

Tyr Met Thr Trp Val Arg Gln Ala Pro Gly Gln Gly Leu Glu Trp Met
            35                  40                  45

Gly Trp Ile Asn Pro Asn Ser Gly Gly Thr Lys Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Tyr Tyr Ala Asn Ser Ala Trp Phe Ala Tyr Trp Gly Gln
            100                 105                 110

Gly Thr Leu Val Thr Val Ser Ser
        115                 120

<210> SEQ ID NO 6
<211> LENGTH: 220
<212> TYPE: PRT
<213> ORGANISM: Artificial Sequence
<220> FEATURE:
<223> OTHER INFORMATION: Synthetic Construct

<400> SEQUENCE: 6

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
                20                  25                  30

Ser Thr Ser Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95
```

```
Val Tyr Asn Leu Pro Trp Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
        210                 215                 220

<210> SEQ ID NO 7
<211> LENGTH: 220
<212> TYPE: PRT
<213> ORGANISM: Artificial Sequence
<220> FEATURE:
<223> OTHER INFORMATION: Synthetic Construct

<400> SEQUENCE: 7

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Gln Ser
            20                  25                  30

Ser Thr Ser Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Val Tyr Asn Leu Pro Trp Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
        210                 215                 220

<210> SEQ ID NO 8
<211> LENGTH: 220
```

```
<212> TYPE: PRT
<213> ORGANISM: Artificial Sequence
<220> FEATURE:
<223> OTHER INFORMATION: Synthetic Construct

<400> SEQUENCE: 8
```

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Ala Thr Ser Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Val Tyr Asn Leu Pro Trp Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

```
<210> SEQ ID NO 9
<211> LENGTH: 446
<212> TYPE: PRT
<213> ORGANISM: Artificial Sequence
<220> FEATURE:
<223> OTHER INFORMATION: Synthetic Construct

<400> SEQUENCE: 9
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Tyr Met Thr Trp Val Arg Gln Ala Pro Gly Gln Gly Leu Glu Trp Met
        35                  40                  45

Gly Trp Ile Asn Pro Asn Ser Gly Gly Thr Lys Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Tyr Tyr Ala Asn Ser Ala Trp Phe Ala Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
        195                 200                 205

Pro Ser Asn Thr Lys Val Asp Lys Thr Val Glu Arg Lys Cys Cys Val
    210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445

<210> SEQ ID NO 10
<211> LENGTH: 446
<212> TYPE: PRT
<213> ORGANISM: Artificial Sequence
<220> FEATURE:
<223> OTHER INFORMATION: Synthetic Construct

<400> SEQUENCE: 10

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

-continued

Tyr Met Thr Trp Val Arg Gln Ala Pro Gly Gln Gly Leu Glu Trp Met
         35                  40                  45

Gly Trp Ile Asn Pro Asn Ser Gly Gly Thr Lys Tyr Ala Gln Lys Phe
 50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
             85                  90                  95

Ala Arg Gly Tyr Tyr Ala Asn Ser Ala Trp Phe Ala Tyr Trp Gly Gln
                100                 105                 110

Gly Thr Leu Val Thr Val Ser Ser Ala Ser Thr Lys Gly Pro Ser Val
         115                 120                 125

Phe Pro Leu Ala Pro Cys Ser Arg Ser Thr Ser Glu Ser Thr Ala Ala
 130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
         180                 185                 190

Ser Ser Asn Phe Gly Thr Gln Thr Tyr Thr Cys Asn Val Asp His Lys
             195                 200                 205

Pro Ser Asn Thr Lys Val Asp Lys Thr Val Glu Arg Lys Cys Cys Val
 210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
         260                 265                 270

Gln Phe Asn Trp Tyr Val Asp Gly Val Glu Val His Asn Ala Lys Thr
             275                 280                 285

Lys Pro Arg Glu Glu Gln Phe Asn Ser Thr Tyr Arg Val Val Ser Val
 290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
         340                 345                 350

Ser Gln Glu Glu Met Thr Lys Asn Gln Val Ser Leu Thr Cys Leu Val
             355                 360                 365

Lys Gly Phe Tyr Pro Ser Asp Ile Ala Val Glu Trp Glu Ser Asn Gly
 370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
         420                 425                 430

Asn His Tyr Thr Gln Lys Ser Leu Ser Leu Ser Leu Gly Lys
             435                 440                 445

<210> SEQ ID NO 11
<211> LENGTH: 739
<212> TYPE: PRT
<213> ORGANISM: Artificial Sequence
<220> FEATURE:
<223> OTHER INFORMATION: Synthetic Construct

<400> SEQUENCE: 11

```
Thr Pro Trp Ser Leu Ala Arg Pro Gln Gly Ser Cys Ser Leu Glu Gly
  1               5                  10                  15

Val Glu Ile Lys Gly Gly Ser Phe Arg Leu Gln Glu Gly Gln Ala
             20                  25                  30

Leu Glu Tyr Val Cys Pro Ser Gly Phe Tyr Pro Tyr Pro Val Gln Thr
             35                  40                  45

Arg Thr Cys Arg Ser Thr Gly Ser Trp Ser Thr Leu Lys Thr Gln Asp
 50                  55                  60

Gln Lys Thr Val Arg Lys Ala Glu Cys Arg Ala Ile His Cys Pro Arg
 65                  70                  75                  80

Pro His Asp Phe Glu Asn Gly Glu Tyr Trp Pro Arg Ser Pro Tyr Tyr
                 85                  90                  95

Asn Val Ser Asp Glu Ile Ser Phe His Cys Tyr Asp Gly Tyr Thr Leu
                100                 105                 110

Arg Gly Ser Ala Asn Arg Thr Cys Gln Val Asn Gly Arg Trp Ser Gly
            115                 120                 125

Gln Thr Ala Ile Cys Asp Asn Gly Ala Gly Tyr Cys Ser Asn Pro Gly
130                 135                 140

Ile Pro Ile Gly Thr Arg Lys Val Gly Ser Gln Tyr Arg Leu Glu Asp
145                 150                 155                 160

Ser Val Thr Tyr His Cys Ser Arg Gly Leu Thr Leu Arg Gly Ser Gln
                165                 170                 175

Arg Arg Thr Cys Gln Glu Gly Gly Ser Trp Ser Gly Thr Glu Pro Ser
            180                 185                 190

Cys Gln Asp Ser Phe Met Tyr Asp Thr Pro Gln Glu Val Ala Glu Ala
        195                 200                 205

Phe Leu Ser Ser Leu Thr Glu Thr Ile Glu Gly Val Asp Ala Glu Asp
    210                 215                 220

Gly His Gly Pro Gly Glu Gln Gln Lys Arg Lys Ile Val Leu Asp Pro
225                 230                 235                 240

Ser Gly Ser Met Asn Ile Tyr Leu Val Leu Asp Gly Ser Asp Ser Ile
                245                 250                 255

Gly Ala Ser Asn Phe Thr Gly Ala Lys Lys Cys Leu Val Asn Leu Ile
            260                 265                 270

Glu Lys Val Ala Ser Tyr Gly Val Lys Pro Arg Tyr Gly Leu Val Thr
        275                 280                 285

Tyr Ala Thr Tyr Pro Lys Ile Trp Val Lys Val Ser Glu Ala Asp Ser
    290                 295                 300

Ser Asn Ala Asp Trp Val Thr Lys Gln Leu Asn Glu Ile Asn Tyr Glu
305                 310                 315                 320

Asp His Lys Leu Lys Ser Gly Thr Asn Thr Lys Lys Ala Leu Gln Ala
                325                 330                 335

Val Tyr Ser Met Met Ser Trp Pro Asp Asp Val Pro Pro Glu Gly Trp
            340                 345                 350

Asn Arg Thr Arg His Val Ile Ile Leu Met Thr Asp Gly Leu His Asn
        355                 360                 365
```

Met Gly Gly Asp Pro Ile Thr Val Ile Asp Glu Ile Arg Asp Leu Leu
370                 375                 380

Tyr Ile Gly Lys Asp Arg Lys Asn Pro Arg Glu Asp Tyr Leu Asp Val
385                 390                 395                 400

Tyr Val Phe Gly Val Gly Pro Leu Val Asn Gln Val Asn Ile Asn Ala
                405                 410                 415

Leu Ala Ser Lys Lys Asp Asn Glu Gln His Val Phe Lys Val Lys Asp
                420                 425                 430

Met Glu Asn Leu Glu Asp Val Phe Tyr Gln Met Ile Asp Glu Ser Gln
                435                 440                 445

Ser Leu Ser Leu Cys Gly Met Val Trp Glu His Arg Lys Gly Thr Asp
450                 455                 460

Tyr His Lys Gln Pro Trp Gln Ala Lys Ile Ser Val Ile Arg Pro Ser
465                 470                 475                 480

Lys Gly His Glu Ser Cys Met Gly Ala Val Val Ser Glu Tyr Phe Val
                485                 490                 495

Leu Thr Ala Ala His Cys Phe Thr Val Asp Asp Lys Glu His Ser Ile
                500                 505                 510

Lys Val Ser Val Gly Gly Glu Lys Arg Asp Leu Glu Ile Glu Val Val
                515                 520                 525

Leu Phe His Pro Asn Tyr Asn Ile Asn Gly Lys Lys Glu Ala Gly Ile
                530                 535                 540

Pro Glu Phe Tyr Asp Tyr Asp Val Ala Leu Ile Lys Leu Lys Asn Lys
545                 550                 555                 560

Leu Lys Tyr Gly Gln Thr Ile Arg Pro Ile Cys Leu Pro Cys Thr Glu
                565                 570                 575

Gly Thr Thr Arg Ala Leu Arg Leu Pro Pro Thr Thr Thr Cys Gln Gln
                580                 585                 590

Gln Lys Glu Glu Leu Leu Pro Ala Gln Asp Ile Lys Ala Leu Phe Val
                595                 600                 605

Ser Glu Glu Glu Lys Lys Leu Thr Arg Lys Glu Val Tyr Ile Lys Asn
                610                 615                 620

Gly Asp Lys Lys Gly Ser Cys Glu Arg Asp Ala Gln Tyr Ala Pro Gly
625                 630                 635                 640

Tyr Asp Lys Val Lys Asp Ile Ser Glu Val Val Thr Pro Arg Phe Leu
                645                 650                 655

Cys Thr Gly Gly Val Ser Pro Tyr Ala Asp Pro Asn Thr Cys Arg Gly
                660                 665                 670

Asp Ser Gly Gly Pro Leu Ile Val His Lys Arg Ser Arg Phe Ile Gln
                675                 680                 685

Val Gly Val Ile Ser Trp Gly Val Val Asp Val Cys Lys Asn Gln Lys
                690                 695                 700

Arg Gln Lys Gln Val Pro Ala His Ala Arg Asp Phe His Ile Asn Leu
705                 710                 715                 720

Phe Gln Val Leu Pro Trp Leu Lys Glu Lys Leu Gln Asp Glu Asp Leu
                725                 730                 735

Gly Phe Leu

<210> SEQ ID NO 12
<211> LENGTH: 3
<212> TYPE: PRT
<213> ORGANISM: Artificial Sequence
<220> FEATURE:
<223> OTHER INFORMATION: Synthetic Construct
<220> FEATURE:

```
<221> NAME/KEY: MISC_FEATURE
<222> LOCATION: (2)..(2)
<223> OTHER INFORMATION: Xaa is an amino acid other than Pro

<400> SEQUENCE: 12

Asn Xaa Ser
1

<210> SEQ ID NO 13
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa is an amino acid other than Pro

<400> SEQUENCE: 13

Asn Xaa Thr
1

<210> SEQ ID NO 14
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (3)..(3)
<223> OTHER INFORMATION: Xaa is any amino acid

<400> SEQUENCE: 14

Thr Xaa Xaa Pro
1

<210> SEQ ID NO 15
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (3)..(3)
<223> OTHER INFORMATION: Xaa is any amino acid

<400> SEQUENCE: 15

Ser Xaa Xaa Pro
1
```

US 9,803,005 B2

HUMANEERED ANTI-FACTOR B ANTIBODY

CROSS-REFERENCE TO RELATED APPLICATION

This application claims benefit of priority to U.S. Provisional Application No. 61/651,472, filed May 24, 2012, which is hereby incorporated by reference.

FIELD OF THE INVENTION

The present invention relates to novel engineered forms of a monoclonal antibody and antigen-binding fragment thereof that binds complement protein factor B and selectively inhibits the alternative complement pathway. The invention also generally relates to the use of such antibodies and antigen-binding fragments thereof to treat diseases in which the alternative complement pathway plays a role. In particular, the invention relates to the use of such antibodies and antigen-binding fragments thereof to inhibit activation of the alternative complement pathway, and to treat diseases in which activation of the alternative complement pathway is implicated. Such disorders include, but are not limited to, airway hyperresponsiveness and airway inflammation, ischemia-reperfusion injury, and related disorders in animals, including humans.

BACKGROUND OF THE INVENTION

During or after translation, many eukaryotic proteins are further modified in vivo by an enzymatic process, namely, glycosylation, which attaches glycans to the proteins. Glycans serve a variety of structural and functional roles in membrane and secreted proteins. For reviews on protein glycosylation, see, for example, Lis and Sharon, *Eur. J. Biochem.* 218:1-27 (1993). One exemplary function of glycosylation is to increase the solubility of the protein substrate. Glycosylation is often species- and cell-specific, and is determined as well by the structure of the protein backbone and the carbohydrate attachment site. However, during protein expression in eukaryotic cells containing glycosylation machineries, different product species from a single protein template are often inevitably produced, containing various lengths or components of glycan side chains. Thus, there is a need to control glycosylation during protein expression to achieve a product of improved purity. Among well-known technologies, site-directed mutagenesis is often used to remove the glycosylation site of the protein to be expressed, resulting in protein products with less or no glycosylation at the site.

The murine anti-factor B antibody produced by the hybridoma clone 1379 (mAb 1379) and its humaneered antibodies or fragments are disclosed in U.S. Patent Publication No. US 2005/0260198 A1, now U.S. Pat. No. 7,999,082 and U.S. Patent Publication No. US 2008/0299114, now U.S. Pat. No. 7,964,705, which are incorporated herein by reference in their entirety. One of these humaneered anti-factor B antigen-binding fragments, TA106, contains a consensus triplet amino acid residue sequence, which represents thematically a potential glycosylation site, in its light chain CDR1 domain. Thus, for future eukaryotic expression and purification of TA106 or TA106-related antibodies or fragments, there is a need to determine whether the expressed antibodies or fragments are actually glycosylated at this site. If the expressed antibodies or fragments are actually glycosylated at this site, there is a further need to reduce or eliminate the site-specific glycosylation to improve product homogeneity, while at the same time maintaining the binding characteristics of such anti-factor B antibodies or fragments, e.g., the binding specificity, the binding efficacy, etc.

All references cited herein, including patent applications and publications, are hereby incorporated by reference in their entirety.

BRIEF SUMMARY OF THE INVENTION

In one aspect, the present invention provides a humaneered anti-factor B antibody or antigen-binding fragment thereof that selectively binds to factor B within the third short consensus repeat ("SCR") domain and prevents formation of the C3bBb complex, wherein the humaneered antibody or antigen-binding fragment thereof has an equilibrium dissociation constant ("$K_D$") between about $1.0 \times 10^{-8}$ M and about $1.0 \times 10^{-10}$ M, wherein the humaneered antibody or antigen-binding fragment thereof further comprises at least one mutation resulting in a different glycosylation pattern compared to the non-mutated antibody or antigen-binding fragment thereof (such as the TA106 originated antibody or a humaneered antibody of mouse monoclonal antibody mAb1379 (mAb1379)). In one embodiment, the antigen affinity of the mutated antibody or antigen-binding fragment thereof is comparable to that of the non-mutated antibody or antigen-binding fragment thereof. In another embodiment, the nucleotide sequence encoding the antibody or antigen-binding fragment disclosed in this application comprises at least one mutation resulting in at least one mutation of a potential glycosylation site on the antibody or antigen-binding fragment thereof. In still another embodiment, the at least one mutation eliminates at least one existing potential glycosylation site on the antibody or antigen-binding fragment thereof. In one preferred embodiment, the at least one mutation reduces the total glycosylation of the antibody or antigen-binding fragment thereof by at least 50%. In another preferred embodiment, the at least one existing potential glycosylation site comprises:

i) an N-glycosylation site selected from the group consisting of:
-Asn-X-Ser- (SEQ ID NO: 12); and
-Asn-X-Thr- (SEQ ID NO: 13);
wherein X is an amino acid other than Pro; or
ii) an O-glycosylation site selected from the group consisting of:
-Thr-X-X-Pro- (SEQ ID NO: 14); and
-Ser-X-X-Pro- (SEQ ID NO: 15);
wherein X is an amino acid.

In some embodiments, the glycosylation site is -Asn-X-Ser (SEQ ID NO: 12) or Asn-X-Thr (SEQ ID NO: 13) and the at least one mutation replaces the Asn at the N-glycosylation site on the antibody or antigen-binding fragment thereof. In one embodiment, the Asn is replaced by Gln, Glu or Asp. In one preferred embodiment, the Asn is replaced by Gln. In one embodiment, the glycosylation site is -Asn-X-Ser (SEQ ID NO: 12) or Asn-X-Thr (SEQ ID NO: 12) and the at least one mutation replaces the Ser at the N-glycosylation site on the antibody or antigen-binding fragment thereof. In one embodiment, the Ser is replaced by Ala, Gly, or His. In one preferred embodiment, the Ser is replaced by Ala.

In one embodiment, the antibody or antigen-binding fragment thereof comprises the $V_\kappa$ domain sequence SEQ ID NO: 2. In another embodiment, the antibody or antigen-binding fragment thereof comprises the $V_\kappa$ domain sequence SEQ ID NO: 3. In another embodiment, the antibody or antigen-binding fragment thereof comprises the light chain sequence SEQ ID NO: 7. In still another embodiment, the antibody or antigen-binding fragment thereof comprises the light chain sequence SEQ ID NO: 8. In one embodiment, the antibody or antigen-binding fragment thereof comprises a $V_\kappa$ sequence selected from SEQ ID NOs: 2 or 3, and a $V_H$ sequence selected from SEQ ID NOs: 4 or 5. In another embodiment, the antibody or antigen-binding fragment thereof comprises a light chain sequence selected from SEQ ID NOs: 7 or 8, and a heavy chain sequence selected from SEQ ID NOs: 10 or 9.

In another aspect, the present invention provides a nucleic acid comprising a sequence encoding the humaneered anti-factor B antibody or antigen-binding fragment thereof in this disclosure. In another aspect, the present invention provides an expression vector comprising the nucleic acid. In some embodiments, the expression vector further comprises a leader sequence for secretion of the antibody or antigen-binding fragment thereof. In still another aspect, the present invention provides a host cell comprising the expression vector.

In another aspect, the present invention provides a method for producing the humaneered anti-factor B antibody or antigen-binding fragment thereof disclosed herein, the method comprising the steps of:

i) introducing at least one mutation into a polynucleotide sequence encoding the parent humaneered anti-factor B antibody or antigen-binding fragment thereof, wherein the mutation eliminates an existing potential glycosylation site on the parent antibody or antigen-binding fragment thereof; and ii) expressing the mutated polynucleotide from step (i) in a cell capable of glycosylating the antibody or antigen-binding fragment thereof.

In some embodiments, the at least one mutation results in at least one amino acid substitution that eliminates an existing potential glycosylation site on the parent humaneered antibody or antigen-binding fragment thereof. In one embodiment, the parent humaneered antibody or antigen-binding fragment thereof comprises a light chain Complementarity Determining Region 1 (CDR1) sequence comprising residues 24 through 40 of SEQ ID NO: 1, wherein the N-glycosylation site is Asn31Ser32Ser33 in the CDR1 of SEQ ID NO: 1.

In another aspect, the present invention provides a method of treating a disease or disorder involving activation of the alternative complement pathway, comprising administering the humaneered anti-factor B antibody or antigen-binding fragment thereof having decreased glycosylation disclosed herein to a mammal that has, or is at risk of developing, said disease or disorder. In some embodiments, the disease or disorder is airway hyperresponsiveness ("AHR") or airway inflammation. In other embodiments, the humaneered anti-factor B antibody or antigen-binding fragment thereof is administered to the individual in an amount effective to measurably reduce AHR or airway inflammation in the mammal as compared to before administration of the antibody or antigen-binding fragment thereof. In one embodiment, said AHR or airway inflammation is associated with a disease selected from the group consisting of asthma, chronic obstructive pulmonary disease ("COPD"), allergic bronchopulmonary aspergillosis, hypersensitivity pneumonia, eosinophilic pneumonia, emphysema, bronchitis, allergic bronchitis bronchiectasis, cystic fibrosis, tuberculosis, hypersensitivity pneumonitis, occupational asthma, sarcoid disease, reactive airway disease syndrome, interstitial lung disease, hypereosinophilic syndrome, rhinitis, sinusitis, exercise-induced asthma, pollution-induced asthma, cough variant asthma, parasitic lung disease, respiratory syncytial virus ("RSV") infection, parainfluenza virus ("PIV") infection, rhinovirus ("RV") infection, and adenovirus infection. In one preferred embodiment, the AHR or airway inflammation is associated with allergic inflammation. In another preferred embodiment, the AHR or airway inflammation is associated with asthma. In still another preferred embodiment, the AHR or airway inflammation is associated with COPD.

In another aspect, the present invention provides a method of selectively inhibiting activation of the alternative complement pathway in a mammal that has, or is at risk of developing, a condition or disease in which activation of the alternative complement pathway contributes to the condition or disease, exacerbates at least one symptom of the condition or disease, or causes the condition or disease, comprising administering the humaneered anti-factor B antibody or antigen-binding fragment thereof disclosed herein.

In another aspect, the present invention provides a fusion protein comprising the humaneered anti-factor B antibody or antigen-binding fragment thereof and another agent.

In another aspect, the present invention provides a pharmaceutical composition comprising an effective amount of the humaneered anti-factor B antibody or antigen-binding fragment thereof, and a pharmaceutically acceptable carrier.

DETAILED DESCRIPTION OF THE INVENTION

Figure 1:
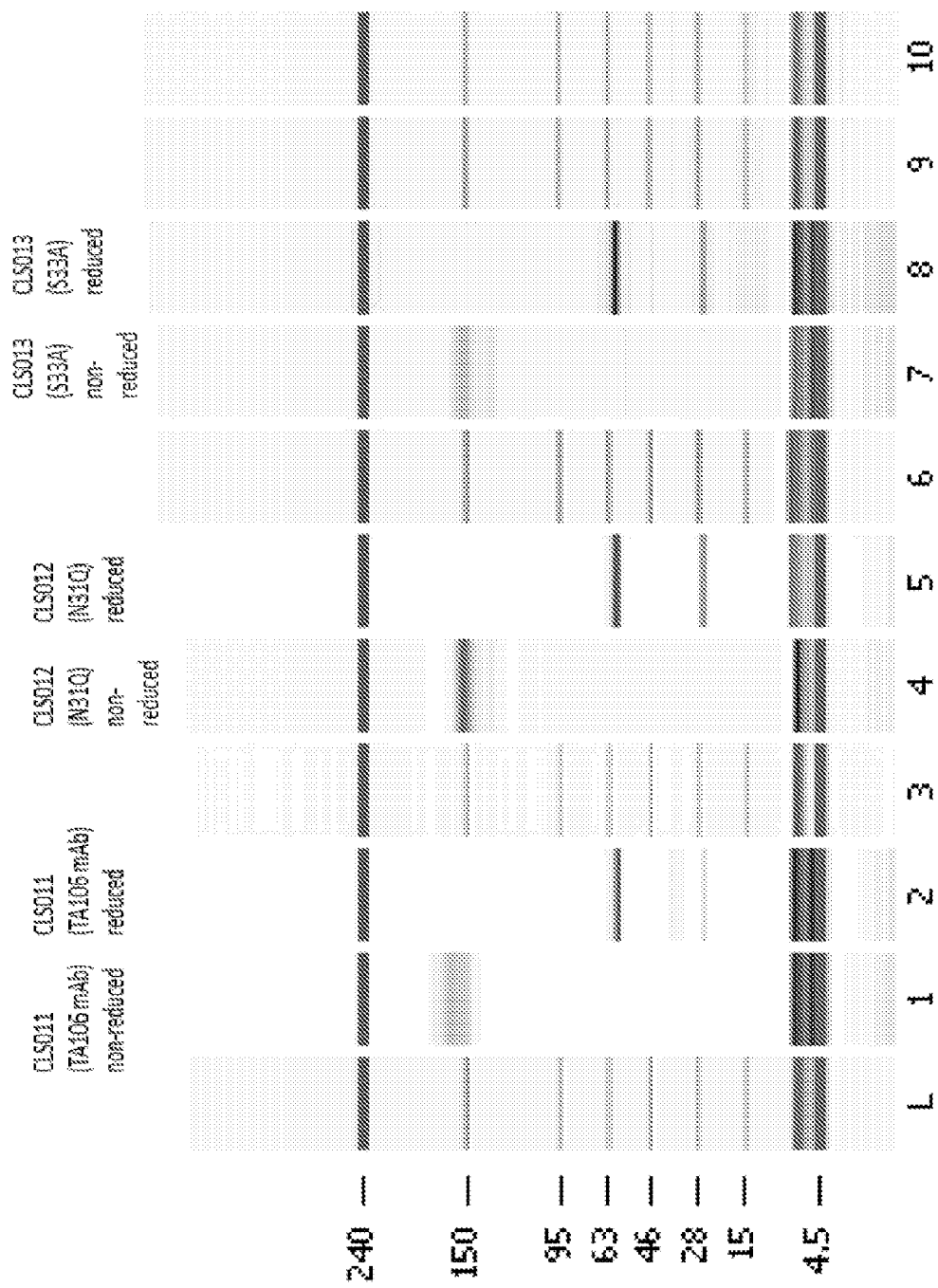
FIG. 1 depicts a SDS-PAGE-like image showing the molecular weights of either the whole antibody of TA106 variants (i.e., CLS011, CLS012, and CLS013 in Lanes 1, 4, and 7, respectively) with non-reduced samples or their heavy and light chains with reduced samples (i.e., heavy/light chains for CLS011, CLS012, and CLS013 in Lanes 2, 5, and 8, respectively). Lanes L, 3, 6, 9, and 10 contain molecular weight standards ("markers"). The image was acquired after capillary electrophoresis using an AGILENT™ protein chip 230 with an AGILENT™ bioanalyzer 2100.

Humaneered anti-factor B antibodies or antigen-binding fragments thereof that selectively bind to complement factor B and selectively inhibit activation of the alternative complement pathway may be used to treat diseases or disorders involving the alternative complement pathway in animals, including humans. In particular, such antibodies or antigen-binding fragments thereof may be used to treat diseases or disorders in animals, including humans, in which activation of the alternative complement pathway plays a role. Such diseases or disorders include, for example, allergic asthma and the accompanying airway inflammation and airway hyperresponsiveness ("AHR"), chronic obstructive pulmonary disease ("COPD"), allergic bronchopulmonary aspergillosis, hypersensitivity pneumonia, eosinophilic pneumonia, emphysema, bronchitis, allergic bronchitis, bronchiectasis, cystic fibrosis, tuberculosis, hypersensitivity pneumonitis, occupational asthma, sarcoid, reactive airway disease syndrome, interstitial lung disease, hyper-eosinophilic syndrome, rhinitis, sinusitis, exercise-induced asthma, pollution-induced asthma, cough variant asthma, parasitic lung disease, respiratory syncytial virus ("RSV") infection, parainfluenza virus ("PIV") infection, rhinovirus ("RV") infection, adenovirus infection, and ischemia-reperfusion injury. See, e.g., U.S. Patent Publication No. US 2005/0260198 A1, which is incorporated herein by reference.

Allergic asthma is a common syndrome associated with airway inflammation and AHR. In patients with allergic asthma, exposure to inhaled allergen leads to an increase in AHR and airway inflammation. Studies have shown increased levels of biologically active fragments derived from the complement C3, C4 and C5 family of proteins, especially C3a and C5a in bronchoalveolar lavage ("BAL") fluid. This suggests that in these patients, activation of the complement pathway through an allergen-induced mechanism occurs in the lung after allergen exposure. Animal models have provided further insight into the role of complement for the development of allergic airway disease. Animals deficient in C3 or C3a receptor appear protected from the development of allergen induced airway disease.

See, e.g., U.S. Patent Publication No. US 2005/0260198 A1, which is incorporated herein by reference.

The variable domains of an antibody are critical for the binding specificity and affinity of the antibody to an antigen. Modification of the variable domains, for example, by modifying the glycosylation pattern of the variable domains, could alter antibody specificity and binding affinity. The present application provides antibodies modified from a parent antibody (the TA106 originated antibody or the corresponding full length antibody, for example) that not only have an altered glycosylation pattern as compared to the parent antibody but also maintain the specificity and affinity of the parent antibody.

Thus, the present application in one aspect provides anti-factor B antibodies having an altered glycosylation pattern as compared to a parent antibody (the TA106 originated antibody or the corresponding full length antibody, for example). In another aspect, there are provided methods of producing anti-factor B antibodies having an altered glycosylation pattern as compared to a parent antibody (the TA106 originated antibody or the corresponding full length antibody, for example). In another aspect, there are provided methods of using such antibodies for treating diseases. Also provided are kits, unit dosages, and articles of manufacture useful for methods described herein.

Definitions

As used herein, the term "antibody" or "immunoglobulin" refers to glycoproteins of the immunoglobulin ("Ig") superfamily of proteins. An antibody or immunoglobulin ("Ig") molecule is tetrameric, comprising two identical light chain polypeptides and two identical heavy chain polypeptides (the terms "light chain polypeptide" and "light chain" or "heavy chain polypeptide" and "heavy chain" are used interchangeably herein to describe the polypeptides of an Ig molecule). The two heavy chains are linked together by disulfide bonds, and each heavy chain is linked to a light chain by a disulfide bond. Each full-length Ig molecule contains at least two binding sites for a specific target or antigen.

The immune system produces several different classes of Ig molecules ("isotypes"), including IgA, IgD, IgE, IgG, and IgM, each distinguished by the particular class of heavy chain polypeptide present: alpha ("α") found in IgA, delta ("δ") found in IgD, epsilon ("ε") found in IgE, gamma ("γ") found in IgG, and mu ("μ") found in IgM. There are at least five different γ heavy chain polypeptides ("isotypes") found in IgG. In contrast, there are only two light chain polypeptide isotypes, referred to as kappa ("κ") and lambda ("λ") chains. The distinctive characteristics of antibody isotypes are defined by sequences of the constant domains of the heavy chain.

An IgG molecule comprises two light chains (either κ or λ form) and two heavy chains (γ form) bound together by disulfide bonds. The κ and λ forms of IgG light chain both contain a domain of relatively variable amino acid sequences, called the variable region (variously referred to as a "$V_L$-," "$V_\kappa$-," or "$V_\lambda$-region") and a domain of relatively conserved amino acid sequences, called the constant region ("$C_L$-region"). Similarly, each IgG heavy chain contains a variable region ("$V_H$-region") and one or more conserved regions: a complete IgG heavy chain contains three constant domains ("$C_H1$-," "$C_H2$-," and "$C_H3$-regions") and a hinge region. Within each $V_L$- or $V_H$-region, hypervariable regions, also known as complementarity-determining regions ("CDR"), are interspersed between relatively conserved framework regions ("FR"). Generally, the variable region of a light or heavy chain polypeptide contains four FR and three CDR arranged in the following order along the polypeptide: NH2-FR1-CDR1-FR2-CDR2-FR3-CDR3-FR4-COOH. Together the CDR and FR determine the three-dimensional structure of the IgG binding site and thus, the specific target protein or antigen to which that IgG molecule binds. Each IgG molecule is dimeric and able to bind two antigen molecules. Cleavage of a dimeric IgG with the protease papain produces two identical antigen-binding fragments ("Fab'") and an "Fc" fragment, so named because it is readily crystallized.

As used herein, the term "antigen-binding fragment" refers to a fragment of an antibody or immunoglobulin molecule that retains the ability to specifically bind its cognate antigen. Antigen-binding fragments generally lack part or all of one or more functional domains present in full-length antibody or Ig molecules, such as those that confer the ability to fix complement and stimulate antibody-dependent cell-mediated cytotoxicity ("ADCC"). Antigen-binding fragments can be prepared from full-length antibody isolates, for example, by digestion with proteases such as papain (which produces two identical monovalent antigen-binding fragments ("Fab'") comprising the variable and constant regions of an antibody light chain and the variable and first constant region of an antibody heavy chain) or pepsin (which produces a single bivalent antigen-binding fragment ("F(ab')$_2$") comprising a pair of Fab' fragments covalently linked near their carboxyl termini).

Other antigen-binding fragments may be produced using standard recombinant DNA methodology, such as "Fv" fragments, single chain Fv antibodies ("scFv"), bi-specific antibodies, diabodies, humanized or humaneered antibodies, and the like. An "Fv" fragment is an antibody fragment that contains a complete antigen recognition and binding site, comprising a dimer of one $V_H$-region and one $V_L$-region. An "scFv" antibody fragment comprises the $V_H$-region and one $V_L$-region of an antibody in a single polypeptide chain. A "diabody" is a small antibody fragment with two antigen-binding sites, comprising a heavy chain variable domain connected to a light chain variable domain in the same polypeptide. By using a linker too short to allow the $V_H$- and $V_L$-regions of the same polypeptide to pair, the domains are forced to pair with complementary domains of a second polypeptide, creating two antigen-binding sites.

As used herein, the term "binding specificity determinant" or "BSD" refers to all or a portion of the amino acid sequence of the third complementarity determining region ("CDR3") and the fourth framework region ("FR4") of an IgG $V_L$ or $V_H$ polypeptide that mediates antigen-binding specificity of a particular Ig molecule. BSDs function in heavy chain and light chain pairs, such that a particular BSD comprises the amino acid sequence of CDR3-FR4 from a $V_L$-region paired with the amino acid sequence of CDR3-FR4 from a cognate $V_H$-region.

As used herein, the term "epitope" refers to a site on a molecule, such as a given protein, polypeptide, or antigen (i.e., factor B), to which an antibody, immunoglobulin, or antigen-binding fragment thereof will bind, and against which an antibody will be produced. The term "epitope" can be used interchangeably with the terms "antigenic determinant," "antibody binding site," or "conserved binding surface" of a given protein, polypeptide, or antigen. More specifically, an epitope can be defined by the amino acid residues or haptens involved in antibody binding and/or by their conformation in three dimensional space (e.g., a conformational epitope or the conserved binding surface). An epitope can be included in peptides as small as about 4-6 amino acid residues, or can be included in larger segments of a protein, and need not be comprised of contiguous amino acid residues when referring to a three dimensional structure of an epitope, particularly with regard to an antibody-binding epitope. Antibody-binding epitopes are frequently conformational epitopes rather than a sequential or linear epitope, or, in other words, an epitope defined by amino acid residues arrayed in three dimensions on the surface of a protein or polypeptide to which an antibody binds. As mentioned above, the conformational epitope is not comprised of a contiguous sequence of amino acid residues, but instead, the residues are perhaps widely separated in the primary protein sequence, and are brought together to form a binding surface by the way the protein folds in its native conformation in three dimensions.

The epitope recognized by the mAb 1379, and shared by the humaneered variants described herein, is a conformational epitope that is not a linear epitope located within the three-dimensional structure of a portion of the third SCR domain of factor B. See, e.g., US 2005/0260198 A1, which is incorporated herein by reference in its entirety. Human factor B is expressed as a 764 amino acid preproprotein containing a twenty-five (25) amino acid signal peptide spanning amino acids 1-25 of its amino terminus. The amino acid sequence for human factor B preproprotein is found in NCBI Database Accession No. P00751. Mature human factor B comprises the amino acid sequence of Accession No. P00751 lacking the twenty-five (25) amino acid signal peptide (i.e., SEQ ID NO: 11). The third SCR domain of mature human factor B extends from about position 137 to about position 195 of SEQ ID NO: 11. The portion that contains the epitope is the three-dimensional structure of factor B that is defined by substantially all of (e.g., at least about 90% of) amino acid positions Ala137-Ser192 of SEQ ID NO: 11, or equivalent positions in a non-human factor B sequence, when such sequence is conformationally arranged as it occurs in the natural full-length factor B sequence.

The murine mAb 1379 and the humaneered variants described herein bind to an epitope or conserved binding surface within or containing a part of the third SCR domain comprising an epitope of human factor B that includes at least a portion of the sequence comprising from about position Tyr139 to about position Ser185 of the mature human factor B protein (SEQ ID NO: 11), to an epitope of human factor B that includes at least a portion of the sequence comprising from about position Tyr139 to about position Ser141 of the mature human factor B protein (SEQ ID NO: 11), to an epitope of human factor B that includes at least a portion of the sequence comprising from about position Glu182 to about position Ser185 with respect to the mature human factor B protein (SEQ ID NO: 11), to an epitope of factor B that includes at least a portion of human factor B (SEQ ID NO: 11) comprising any one or more of the following positions or their equivalent positions in a non-human factor B sequence: Ala137, Tyr139, Cys 140, Ser141, Glu182, Gly184, or Ser185, or to an epitope of factor B that includes at least a portion of the equivalent positions with respect to non-human animal species. In another aspect, the epitope is within or containing a part of portion of the third SCR domain of factor B that includes all or substantially all of (e.g., at least five, six, or seven of) the following amino acid positions of SEQ ID NO: 11, or their equivalent positions in a non-human factor B sequence: Ala137, Tyr139, Ser141, Glu182, Ser185, Thr189, Glu190, and Ser192.

One of skill in the art can readily align the sequence of human factor B with the sequence of factor B from another animal species and determine the positions of the SCR regions and the specific portions of the third SCR regions corresponding to the amino acid positions above. For example, two specific sequences can be aligned to one another using BLAST 2 sequence as described in Tatusova and Madden, (1999), "Blast 2 sequences—a new tool for comparing protein and nucleotide sequences", *FEMS Microbiol. Lett.* 174:247-250, which is incorporated herein by reference in its entirety.

Definitions

As used herein, the term "selectively binds to" refers to the specific binding of one protein to another (e.g., an antibody, antigen-binding fragment thereof, or binding partner to an antigen), wherein the level of binding, as measured by any standard assay (e.g., an immunoassay), is statistically significantly higher than the background control for the assay. For example, when performing an immunoassay, controls typically include a reaction well or tube that contains antibody or antigen binding fragment alone (i.e., in the absence of antigen), wherein an amount of reactivity (e.g., non-specific binding to the well or tube) by the antibody or antigen-binding fragment thereof in the absence of the antigen is considered to be background signal. Binding can be measured using a variety of methods standard in the art, including, but not limited to, Western blot, immunoblot, enzyme-linked immunosorbent assay ("ELISA"), radioimmunoassay ("RIA"), immunoprecipitation, surface plasmon resonance, chemiluminescence, fluorescent polarization, phosphorescence, immunohistochemical analysis, matrix-assisted laser desorption/ionization time-of-flight ("MALDI-TOF") mass spectrometry, microcytometry, microarray, microscopy, fluorescence activated cell sorting ("FACS"), and flow cytometry.

As used herein, "treating" or "to treat" a disease is defined as administering a humaneered variant of mAb 1379 as described above, with the glycosylation site in CDR1 of the light chain variable domain abolished, or antigen-binding fragments thereof, with or without other therapeutic agents, in order to palliate, ameliorate, stabilize, reverse, slow, delay, prevent, reduce, or eliminate either the disease or a symptom of a disease, or to retard or stop the progression of a disease or a symptom of a disease. An "effective amount" of a composition is an amount sufficient to treat a disease.

As used herein, "to inhibit" the alternative complement pathway in an individual refers to inhibiting the expression and/or the biological activity of at least one protein that is part of the alternative complement pathway. Such proteins include, but are not limited to, factor B, factor D or properdin. To "selectively" inhibit the alternative complement pathway means that the method of the present invention preferentially or exclusively inhibits the alternative complement pathway, but does not inhibit or at least does not substantially inhibit other pathways for complement activation, including the classical complement pathway or the lectin pathway. For example, the humaneered factor B antibodies and antigen-binding fragments thereof of the present invention are one example of a reagent that selectively inhibits the alternative complement pathway. This definition applies to other methods described herein wherein the alternative complement pathway is selectively inhibited.

An "individual" is a vertebrate, preferably a mammal, more preferably a human. Mammals include, but are not limited to, farm animals, sport animals, pets, primates, mice and rats. In some embodiments, the individual is human. In some embodiments, the individual is an individual other than a human. In some embodiments, the individual is an animal model for the study of a disease in which the alternative complement pathway is implicated. Individuals amenable to treatment include those who are presently asymptomatic but who are at risk of developing a symptomatic disorder in which the alternative complement pathway plays a role, or in which activation of the alternative complement pathway plays a role.

General reference to "the composition" or "compositions" includes and is applicable to compositions of the invention.

As used herein, the singular forms "a," "an," and "the" include the plural references unless clearly indicated otherwise. For example, the term "a $V_H$-region" includes one or more $V_H$-regions.

Reference to "about" a value or parameter herein includes and describes embodiments that are directed to that value or parameter per se. For example, description referring to "about X" includes description of "X."

It is understood that aspects and embodiments of the invention described herein include "consisting" and/or "consisting essentially of" aspects and embodiments.

Antibodies of the Present Invention

In one aspect, the instant invention provides a humaneered anti-factor B antibody or antigen-binding fragment thereof that selectively binds to factor B within the third short consensus repeat ("SCR") domain and prevents formation of the C3bBb complex, wherein the antibody does not contain a glycosylation site in its light chain CDR1 region. In some embodiments, the antibody does not contain a glycosylation site in its light chain variable region. In some embodiments, the antibody does not contain a glycosylation site in its light chain. In one embodiment, the humaneered antibody or antigen-binding fragment thereof has an equilibrium dissociation constant ("$K_D$") between about $1.0 \times 10^{-8}$ M and about $1.0 \times 10^{-10}$ M. In certain embodiments, the $K_D$ is between about $1.0 \times 10^{-9}$ M and about $9.0 \times 10^{-9}$ M. In certain embodiments, the $K_D$ is between about $3.0 \times 10^{-9}$ M and about $7.0 \times 10^{-9}$ M. In certain embodiments, the $K_D$ is between about $3.0 \times 10^{-9}$ M and about $4.0 \times 10^{-9}$ M. In certain embodiments, the $K_D$ is about $3.7 \times 10^{-9}$ M. In certain embodiments, the $K_D$ is between about $4.0 \times 10^{-9}$ M and about $5.0 \times 10^{-9}$ M. In certain embodiments, the $K_D$ is about $4.5 \times 10^{-9}$ M. In certain embodiments, the $K_D$ is between about $5.0 \times 10^{-9}$ M and about $6.0 \times 10^{-9}$ M. In certain embodiments, the $K_D$ is about $5.4 \times 10^{-9}$ M. In certain embodiments, the $K_D$ is between about $6.0 \times 10^{-9}$ M and about $7.0 \times 10^{-9}$ M. In certain embodiments, the $K_D$ is about $6.5 \times 10^{-9}$ M.

In some embodiments, there is provided a humaneered anti-factor B antibody or antigen binding fragment thereof that selectively binds to factor B within the third SCR domain and prevents formation of the C3bBb complex, wherein the antibody has reduced glycosylation (for example, at least about 10%, 20%, 30%, 40%, or 50% reduced) compared to an antibody comprising a light chain of SEQ ID NO:6 and a heavy chain of SEQ ID NO:9 (the TA106 originated antibody or the corresponding full length antibody, for example). In some embodiments, there is provided a batch (e.g. a commercial batch) of a humaneered anti-factor B antibody or antigen binding fragment thereof that selectively binds to factor B within the third SCR domain and prevents formation of the C3bBb complex, wherein the antibody batch has reduced glycosylation (for example, at least about 10%, 20%, 30%, 40%, or 50% reduced) compared to a batch of an antibody comprising a light chain of SEQ ID NO:6 and a heavy chain of SEQ ID NO:9 (the TA106 originated antibody or the corresponding full length antibody, for example). Antibody glycosylation can be determined, for example, by liquid chromatography-, electrophoresis-, and mass spectroscopy-based methods as described in Chelius et al. (2006) *J. Am. Soc. Mass Spectrom.*, 17: 1590-1598; Rehder et al. (2006) *J. Chromatogr. A.*, 1102: 164-175; Srebalus and Lim (2007) *Mass Spectrom. Rev.*, 36: 370-388; and Wang et al. (2005) *Pharm. Res.*, 22: 1338-1349. Additional techniques to assay antibody glycosylation are described in Beck et al. (2008) *Curr. Pharm. Biotech.* 9: 482-501 and references cited therein. In one embodiment, the humaneered antibody or antigen-binding fragment thereof has an equilibrium dissociation constant ("KD") between about $1.0 \times 10^{-8}$ M and about $1.0 \times 10^{-10}$ M. In certain embodiments, the KD is between about $1.0 \times 10^{-9}$ M and about $9.0 \times 10^{-9}$ M. In certain embodiments, the KD is between about $3.0 \times 10^{-9}$ M and about $7.0 \times 10^{-9}$ M. In certain embodiments, the KD is between about $3.0 \times 10^{-9}$ M and about $4.0 \times 10^{-9}$ M. In certain embodiments, the KD is about $3.7 \times 10^{-9}$ M. In certain embodiments, the KD is between about $4.0 \times 10^{-9}$ M and about $5.0 \times 10^{-9}$ M. In certain embodiments, the KD is about $4.5 \times 10^{-9}$ M. In certain embodiments, the KD is between about $5.0 \times 10^{-9}$ M and about $6.0 \times 10^{-9}$ M. In certain embodiments, the KD is about $5.4 \times 10^{-9}$ M. In certain embodiments, the KD is between about $6.0 \times 10^{-9}$ M and about $7.0 \times 10^{-9}$ M. In certain embodiments, the KD is about $6.5 \times 10^{-9}$ M. In some embodiments, the antibody has an anti-hemolytic activity that is equivalent to that of the TA106 originated antibody or corresponding full length antibody. In some embodiments, the antibody has at least about 80%, 85%, 90%, 95%, 98%, 99%, or 100% binding affinity as that of the TA106 originated antibody or corresponding full length antibody.

In some embodiments, there is provided a humaneered anti-factor B antibody or antigen binding fragment thereof that selectively binds to factor B within the third SCR domain and prevents formation of the C3bBb complex, wherein the antibody has increased homogeneity (for example at least about 10%, 20%, 30%, 40%, or 50% increased) compared to an antibody comprising a light chain of SEQ ID NO:6 and a heavy chain of SEQ ID NO:9 (the TA106 originated antibody or the corresponding full length antibody, for example). In some embodiments, there is provided a batch (such as a commercial batch) humaneered anti-factor B antibody or antigen binding fragment thereof that selectively binds to factor B within the third SCR domain and prevents formation of the C3bBb complex, wherein the antibody batch has increased homogeneity (for example at least about 10%, 20%, 30%, 40%, or 50% increased) compared to an antibody batch comprising a light chain of SEQ ID NO:6 and a heavy chain of SEQ ID NO:9 (the TA106 originated antibody or corresponding full length antibody, for example). Antibody homogeneity can be determined, for example, by liquid chromatography-, electrophoresis-, and mass spectroscopy-based methods described above, and by SDS polyacrylamide gel electrophoresis, CE-SES (capillary electrophoresis-sodium dodecyl sulfate), isoelectric focusing, cIEF (capillary isoelectric focusing), imaged cIEF, normal and reverse phase HPLC (high-performance liquid chromatography), fluorophore-assisted carbohydrate electrophoresis, mass spectrometry, sialic acids of released glycans analyses, capillary electrophoresis of released glycans, x-ray diffraction, NMR (nuclear magnetic resonance), and high-throughput glycoanalysis as described in Royle et al. (2006) *Methods Mol Biol.* 347: 125-143 and Sheridan, C. (2007) *Nat. Biotechnol.* 25: 145-146. Additional techniques to assay the homogeneity of antibody glycosylation variants are described in Beck et al. (2008) *Curr. Pharm. Biotech.* 9: 482-501 and references cited therein. In one embodiment, the humaneered antibody or antigen-binding fragment thereof has an equilibrium dissociation constant ("KD") between about $1.0 \times 10^{-8}$ M and about $1.0 \times 10^{-10}$ M. In certain embodiments, the KD is between about $1.0 \times 10^{-9}$ M and about $9.0 \times 10^{-9}$ M. In certain embodiments, the KD is between about $3.0 \times 10^{-9}$ M and about $7.0 \times 10^{-9}$ M. In certain embodiments, the KD is between about $3.0 \times 10^{-9}$ M and about $4.0 \times 10^{-9}$ M. In certain embodiments, the KD is about $3.7 \times 10^{-9}$ M. In certain embodiments, the KD is between about $4.0 \times 10^{-9}$ M and about $5.0 \times 10^{-9}$ M. In certain embodiments, the KD is about $4.5 \times 10^{-9}$ M. In certain embodiments, the KD is between about $5.0 \times 10^{-9}$ M and about $6.0 \times 10^{-9}$ M. In certain embodiments, the KD is about $5.4 \times 10^{-9}$ M. In certain embodiments, the KD is between about $6.0 \times 10^{-9}$ M and about $7.0 \times 10^{-9}$ M. In certain embodiments, the KD is about $6.5 \times 10^{-9}$ M. In some embodiments, the antibody has an anti-hemolytic activity that is equivalent of that of the TA106 originated antibody or corresponding full length antibody. In some embodiments, the antibody has at least about 80%, 85%, 90%, 95%, 98%, 99%, or 100% binding affinity as that of the TA106 originated antibody or corresponding full length antibody.

In some embodiments, there is provided a humaneered anti-factor B antibody or antigen binding fragment thereof that selectively binds to factor B within the third SCR domain and prevents formation of the C3bBb complex, wherein the antibody has an apparent molecular weight of no greater than about any of 50, 45, 40, or 35 kD. In one embodiment, the humaneered antibody or antigen-binding fragment thereof has an equilibrium dissociation constant ("KD") between about $1.0 \times 10^{-8}$ M and about $1.0 \times 10^{-10}$ M. In certain embodiments, the KD is between about $1.0 \times 10^{-9}$ M and about $9.0 \times 10^{-9}$ M. In certain embodiments, the KD is between about $3.0 \times 10^{-9}$ M and about $7.0 \times 10^{-9}$ M. In certain embodiments, the KD is between about $3.0 \times 10^{-9}$ M and about $4.0 \times 10^{-9}$ M. In certain embodiments, the KD is about $3.7 \times 10^{-9}$ M. In certain embodiments, the KD is between about $4.0 \times 10^{-9}$ M and about $5.0 \times 10^{-9}$ M. In certain embodiments, the KD is about $4.5 \times 10^{-9}$ M. In certain embodiments, the KD is between about $5.0 \times 10^{-9}$ M and about $6.0 \times 10^{-9}$ M. In certain embodiments, the KD is about $5.4 \times 10^{-9}$ M. In certain embodiments, the KD is between about $6.0 \times 10^{-9}$ M and about $7.0 \times 10^{-9}$ M. In certain embodiments, the KD is about $6.5 \times 10^{-9}$ M. In some embodiments, the antibody has an anti-hemolytic activity that is equivalent of that of the TA106 originated antibody or corresponding full length antibody. In some embodiments, the antibody has at least about 80%, 85%, 90%, 95%, 98%, 99%, or 100% binding affinity as that of the TA106 originated antibody or corresponding full length antibody.

In some embodiments, there is provided a humaneered anti-factor B antibody or antigen binding fragment thereof that selectively binds to factor B within the third SCR domain and prevents formation of the C3bBb complex, wherein the antibody has a mutation in the light chain at position 31 with respect to SEQ ID NO:6 (for example, the amino acid sequence of the light chain of the TA106 originated antibody or corresponding full length antibody). In some embodiments, the mutation is an Asn to Gln, Glu, or Asp mutation. In some embodiments the mutation is an Asn to Gln mutation. In some embodiments, there is provided a humaneered anti-factor B antibody or antigen binding fragment thereof that selectively binds to factor B within the third SCR domain and prevents formation of the C3bBb complex, wherein the antibody has a mutation in the light chain at position 33 with respect to SEQ ID NO:6 (for example, the amino acid sequence of the light chain of the TA106 originated antibody or corresponding full length antibody). In some embodiments, the mutation is a Ser to Ala, Gly, or His mutation. In some embodiments, the mutation is a Ser to Ala mutation. In some embodiments, there is provided a humaneered anti-factor B antibody or antigen binding fragment thereof that selectively binds to factor B within the third SCR domain and prevents formation of the C3bBb complex, wherein the antibody has a mutation in the heavy chain at position 1 with respect to SEQ ID NO:9 (for example, the amino acid sequence of the heavy chain of the TA106 originated antibody or corresponding full length antibody).

In some embodiments, there is provided a humaneered anti-factor B antibody or antigen binding fragment thereof that selectively binds to factor B within the third SCR domain and prevents formation of the C3bBb complex, wherein the antibody has a mutation in the light chain at position 31 with respect to SEQ ID NO:6 and a mutation in the heavy chain at position 1 with respect to SEQ ID NO:9 (for example, the amino acid sequences of the light and heavy chains of the TA106 originated antibody or corresponding full length antibody). In some embodiments, there is provided a humaneered anti-factor B antibody or antigen binding fragment thereof that selectively binds to factor B within the third SCR domain and prevents formation of the C3bBb complex, wherein the antibody has a mutation in the light chain at position 33 with respect to SEQ ID NO:6 (for example, the amino acid sequence of the light chain of the TA106 originated antibody or corresponding full length antibody). and a mutation in the heavy chain at position 1 with respect to SEQ ID NO:9 (for example, the amino acid sequence of the heavy chain of the TA106 originated antibody or corresponding full length antibody).

In some embodiments, there is provided a humaneered anti-factor B antibody or antigen binding fragment thereof that selectively binds to factor B within the third SCR domain and prevents formation of the C3bBb complex, wherein the antibody comprises a light chain CDR1 of the sequence comprising residues 24-40 of SEQ ID NO:2 (or SEQ ID NO:3). In some embodiments, there is provided a humaneered anti-factor B antibody or antigen binding fragment thereof that selectively binds to factor B within the third SCR domain and prevents formation of the C3bBb complex, wherein the antibody comprises a light chain CDR1 of the sequence comprising residues 24-40 of SEQ ID NO:2 (or SEQ ID NO:3), a light chain CDR2 of the sequence comprising residues 56-63 of SEQ ID NO:2 (or SEQ ID NO:3), and a light chain CDR3 of the sequence comprising residues 95-103 of SEQ ID NO:2 (or SEQ ID NO:3). In some embodiments, there is provided a humaneered anti-factor B antibody or antigen binding fragment thereof that selectively binds to factor B within the third SCR domain and prevents formation of the C3bBb complex, wherein the antibody comprises a light chain variable domain of the sequence of SEQ ID NO:2 (or SEQ ID NO:3). In some embodiments, there is provided a humaneered anti-factor B antibody or antigen binding fragment thereof that selectively binds to factor B within the third SCR domain and prevents formation of the C3bBb complex, wherein the antibody comprises a light chain of the sequence of SEQ ID NO:7 (or SEQ ID NO:8). In some embodiments, there is provided a humaneered anti-factor B antibody or antigen binding fragment thereof that selectively binds to factor B within the third SCR domain and prevents formation of the C3bBb complex, wherein the antibody comprises a light chain CDR1 of the sequence comprising residues 24-40 of SEQ ID NO:2. In some embodiments, there is provided a humaneered anti-factor B antibody or antigen binding fragment thereof that selectively binds to factor B within the third SCR domain and prevents formation of the C3bBb complex, wherein the antibody comprises a light chain CDR1 of the sequence comprising residues 24-40 of SEQ ID NO:2, a light chain CDR2 of the sequence comprising residues 56-63 of SEQ ID NO:2, and a light chain CDR3 of the sequence comprising residues 95-103 of SEQ ID NO:2. In some embodiments, there is provided a humaneered anti-factor B antibody or antigen binding fragment thereof that selectively binds to factor B within the third SCR domain and prevents formation of the C3bBb complex, wherein the antibody comprises a light chain variable domain of the sequence of SEQ ID NO:2.

In some embodiments, the disclosed antibody comprises a light chain polypeptide comprising an amino acid sequence as depicted in SEQ ID NOs: 7 or 8. In some embodiments, the disclosed antibody comprises a heavy chain polypeptide comprising an amino acid sequence as depicted in SEQ ID NOs: 10 or 9. In a preferred embodiment, the disclosed antibody comprises a light chain polypeptide comprising an amino acid sequence as depicted in SEQ ID NOs: 7 or 8, and a heavy chain polypeptide comprising an amino acid sequence as depicted in SEQ ID NOs: 10 or 9.

In one embodiment, the instantly disclosed antibody or antigen-binding fragment thereof comprises a light chain Complementarity Determining Region 1 (CDR1) sequence comprising residues 24 through 40 of SEQ ID NOs: 2 or 3. In one embodiment, the instant antibody or antigen-binding fragment thereof comprises a light chain CDR2 sequence comprising residues 56 through 62 of SEQ ID NOs: 2 or 3. In one embodiment, the instant antibody or antigen-binding fragment thereof comprises a light chain CDR3 sequence comprising residues 95 through 103 of SEQ ID NOs: 2 or 3.

In one embodiment, the instant antibody or antigen-binding fragment thereof comprises a heavy chain CDR1 sequence comprising residues 31 through 35 of SEQ ID NO: 5. In one embodiment, the instant antibody or antigen-binding fragment thereof comprises a heavy chain CDR2 sequence comprising residues 50 through 66 of SEQ ID NO: 5. In one embodiment, the instant antibody or antigen-binding fragment thereof comprises a heavy chain CDR3 sequence comprising residues 99 through 109 of SEQ ID NO: 5. In some embodiments, the antibody or antigen-binding fragment thereof comprises a heavy chain CDR1 sequence of residues 31 through 35 of SEQ ID NO: 5, a heavy chain CDR2 sequence comprising residues 50 through 66 of SEQ ID NO: 5, and a heavy chain CDR3 sequence comprising residues 99 through 109 of SEQ ID NO: 5.

In some embodiments, the instant antibody or antigen-binding fragment thereof comprises: 1) a light chain Complementarity Determining Region 1 (CDR1) sequence comprising residues 24 through 40 of SEQ ID NOs: 2 or 3; 2) a light chain CDR2 sequence comprising residues 56 through 62 of SEQ ID NOs: 2 or 3; 3) a light chain CDR3 sequence comprising residues 95 through 103 of SEQ ID NOs: 2 or 3; 4) a heavy chain CDR1 sequence comprising residues 31 through 35 of SEQ ID NO: 5; 5) a heavy chain CDR2 sequence comprising residues 50 through 66 of SEQ ID NO: 5; and 6) a heavy chain CDR3 sequence comprising residues 99 through 109 of SEQ ID NO: 5.

In some embodiments, the antibody or antigen-binding fragment thereof comprises 1) a light chain variable domain having the sequence of SEQ ID NO:2 (or SEQ ID NO:3) and 2) a heavy chain variable domain having the sequence of SEQ ID NO:4. In some embodiments, the antibody or antigen-binding fragment thereof comprises 1) a light chain variable domain having the sequence of SEQ ID NO:2 (or SEQ ID NO:3) and 2) a heavy chain variable domain having the sequence of SEQ ID NO:5.

In some embodiments, the antibody or antigen-binding fragment thereof comprises 1) a light chain having the sequence of SEQ ID NO:7 (or SEQ ID NO:8) and 2) a heavy chain having the sequence of SEQ ID NO:9 (such as the heavy chain of the TA106 originated antibody or corresponding full length antibody). In some embodiments, the antibody or antigen-binding fragment thereof comprises 1) a light chain variable domain having the sequence of SEQ ID NO:7 (or SEQ ID NO:8) and 2) a heavy chain having the sequence of SEQ ID NO:10.

In some embodiments, the antibody or antigen-binding fragment thereof comprises 1) a light chain variable domain having the sequence of SEQ ID NO:1 and 2) a heavy chain variable domain having the sequence of SEQ ID NO:5. In some embodiments, the antibody or antigen-binding fragment thereof comprises 1) a light chain having the sequence of SEQ ID NO:6; and 2) a heavy chain having the sequence of SEQ ID NO:10.

In some embodiments, the disclosed antibody or antigen-binding fragment thereof is glycosylated in vivo or in vitro before or after isolation or purification.

Glycosylation, which attaches glycans to the proteins, is an enzyme-directed site-specific process, as opposed to the non-enzymatic chemical reaction of glycation. The majority of proteins synthesized in the rough endoplasmic reticulum (ER) undergo glycosylation. Glycosylation is also present in the cytoplasm and nucleus as the O-GlcNAc modification. Glycans serve a variety of structural and functional roles in membrane and secreted proteins. Five classes of glycans are produced: 1) N-linked glycans attached to a nitrogen of asparagine or arginine side-chains; 2) O-linked glycans attached to the hydroxyl oxygen of serine, threonine, tyrosine, hydroxylysine, or hydroxyproline side-chains, or to oxygens on lipids such as ceramide; 3) phospho-glycans linked through the phosphate of a phospho-serine; 4) C-linked glycans, a rare form of glycosylation where a sugar is added to a carbon on a tryptophan side-chain; and 5) glypiation, which is the addition of a GPI anchor that links proteins to lipids through glycan linkages. For reviews on protein glycosylation, see, for example, Lis and Sharon, *Eur. J. Biochem.* 218:1-27 (1993).

It is generally accepted that N-linked glycosylation in the IgG CH2 domain is required for functional engagement of activating FcγR receptors. For example, Mimura et al. reported that "[o]ne of the most intriguing issues is that glycosylation of IgG-Fc is essential for the recognition by FcγRs although the carbohydrate moieties are on the periphery of the FcγRIII-Fc interface" (Mimura et al., *J. Biol. Chem.* 2001, 276:45539). A recent review by Raju further discusses modulating effector function of antibodies by changes in glycosylation and summarizes the proposed importance of the oligosaccharides found on human IgGs with their degree of effector function (Raju, *BioProcess International* 2003, 44-53). According to Wright and Morrison, the microheterogeneity of human IgG oligosaccharides can affect biological functions such as CDC and ADCC, binding to various Fc receptors, and binding to C1q protein (Wright and Morrison, *Trends Biotechnol.* 1997, 15(1):26-32). It is well documented that glycosylation patterns of antibodies can differ depending on the producing cell and the cell culture conditions (Raju, *BioProcess International* 2003, 44-53). Such differences can lead to changes in both effector function and pharmacokinetics (Israel et al., *Immunology* 1996, 89(4):573-578; Newkirk et al., *Clin Exp*

*Immunol* 1996, 106(2):259-64). In addition, the presence or absence of fucose in the oligosaccharide component of an IgG can improve binding and ADCC (Shields et al., *J. Biol. Chem.* 2002; 277(30):26733-40). An IgG that lacked a fucosylated carbohydrate linked to Asn$^{297}$ exhibited normal receptor binding to the FcγR1. In contrast, binding to the FcγRIIIA receptor was improved up to 50-fold and accompanied by enhanced ADCC, especially at lower antibody concentrations.

Glycosylation is often species- and cell-specific, and is determined as well by the structure of the protein backbone and the carbohydrate attachment site. Work by Shinkawa et al. demonstrated that an antibody to the human IL-5 receptor produced in a rat hybridoma showed more than 50-fold higher ADCC when compared to the antibody produced in Chinese hamster ovary cells (CHO) (Shinkawa et al., *J Biol Chem.* 2003, 278(5):3466-73). Monosaccharide composition and oligosaccharide profiling showed that the rat hybridoma-produced IgG had a lower content of fucose than the CHO-produced protein. The authors concluded that the lack of fucosylation of an IgG1 has a critical role in enhancement of ADCC activity.

One aspect of the present invention provides antibodies which are modified in their glycosylation patterns. The altered glycosylation may include, for example, a decrease in the number of glycosylated amino acid residues or a change in the pattern or location of glycosylated residues. In some embodiments, the glycosylation in the variable region is altered.

The modification of the glycosylation of native antibodies can be obtained through different methods known in the art. Modification of the glycosylation pattern in the antigen binding site of the antibodies of the present invention can be achieved by enzymatic treatment of purified antibodies. Alternatively, modification of the glycans of the antibodies of the present invention can be achieved by producing the antibodies in cell lines with suitable glycosylation enzymes or by modifying the cell culture conditions to modify the activity of the glycosylation enzymes of the cell line producing the antibodies. Alternatively, the antibodies of the present invention can also be produced by genetically modifying the antigen binding site of the antibody in order to remove glycosylation sites.

Many carbohydrate cleaving or transferring enzymes can be applied in order to modify the glycosylation pattern of a native antibody. The glycosylation can be decreased completely or partially. In a particular embodiment, the modification is obtained in the antigen binding region of the antibody. Enzymes can be applied on a native antibody in a different order and under variable circumstances (concentrations, time, temperature, buffer, etc.) in order to obtain antibodies with different glycosylation patterns.

Enzymes such as peptide N-4(N-acetyl-beta-glucosaminyl)asparagine amidase F (PNGase F), also called N-glycosidase F, are exemplary enzymes capable of modifying protein glycosylation. This enzyme has a broad specificity, and it releases nearly all known N-linked oligosaccharide chains from proteins (Plummer et al. (1984) *J Biol Chem.* 259, 10700-10704). This enzyme releases tetra- and penta-antennary chains. It is noteworthy that the activity of the enzyme can only be predicted when the glycoprotein is fully denatured. Accordingly, the activity of the enzyme on an intact antibody must be controlled in each case. Methods to control the deglycosylation of the antibody are described in *Current Protocols in Protein Science*, Ed. G. Taylor, Unit 12.4; John Wiley & Sons, Inc.

Truncated glycoforms of IgG can be generated by sequential enzymatic treatment as described in Mimura et al. (2001) *J Biol Chem.* 276, 45539-45547.

Sialic acids are the terminal sugars on many N- and O-linked oligosaccharides. As an example, sialic acid molecules can be removed from IgG proteins in an acetate buffer, pH 5.0, by sialidase enzymes (such as the sialidase from *Arthrobacter ureafaciens*, Roche Molecular Diagnostics, East Sussex, UK) at 37° C. for 24 hours. Removal of sialic acids results in an increase in the isoelectric point of the protein. Isoelectrofocusing (IEF) can therefore be used to control removal of sialic acids.

Galactose can be removed by treatment with beta-galactosidase in an acetate buffer at 37° C. for 24 hours. N-acetyl-glucosamine can be cleaved by treatment with N-acetyl-beta-D-glucosaminidase (*D. pneumoniae*, Roche, Molecular Biochemicals) at 37° C. for 24 hours. Mannose residues can then be removed by treatment with alpha-mannosidase at 37° C. for 48 hours (Mimura et al., cited supra).

An alternative method for modifying the glycosylation of recombinant antibodies or antigen-binding fragments thereof is to produce said antibodies or fragments in cell lines having a repertoire of glycosylation enzymes. Chinese Hamster Ovary cells (CHO) are a well-known example of such cell lines.

Although CHO cells have most of the human repertoire of glycosylation enzymes, they are deficient in particular glycosyltransferases. In particular, the alpha 2,6-sialyl-transferase gene is not expressed endogenously in CHO cells. This enzyme adds terminal galactose sugars with sialic acid in the alpha 2, 6 positions on the Gal β1-4GlcNAc-R sequence. However, CHO cells express a functional alpha-2,3-sialyl-transferase so that the terminal sialic acids are in alpha 2,3 linkage to galactose. Alpha-3/4 fucosyltransferase is also not synthesized by these cells (Grabenhorst et al. (1999) *Glycoconj. J.* 16:81).

Another method to produce recombinant antibody or fragment thereof with a modified glycosylation pattern is to use a cell line genetically modified to express glycosylation enzymes from other strains. In particular, a CHO-K1 cell line transfected with an alpha-2,6-sialyltransferase gene cloned from another strain can be used (cited supra).

Expression systems potentially suitable for generation of recombinant antibody or fragment thereof with a modified glycosylation pattern include, for example, yeast (e.g., *Saccharomyces, Pichia, Hansenula*), insect cells (baculovirus expression), plant cells or plants, and mammalian cells. For expression of fragments of an antibody, yeast expression provides an alternative for insect or mammalian cell expression. If no glycosylation is needed, the expression in bacteria is considered.

The repertoire of glycosylating enzymes differs among cell types. In order to obtain a desired glycosylation pattern, one or more glycosylating enzymes can be temporarily (for example by antisense or siRNA technology) or permanently inhibited (gene inactivation). In certain embodiments yeast cells have a limited repertoire of enzymes involved in glycosylation.

Glycosylation often improves protein solubility. In certain embodiments, it is advantageous to express a recombinant protein with an extensive glycosylation (and good solubility) and to treat the recombinant protein afterwards with deglycosylating enzymes.

Cell culture conditions can also be exploited to modify the glycosylation of the recombinant antibody or fragment thereof. The concentration of dissolved oxygen at steady state in serum-free culture has an effect on protein glycosylation. For example, the extent of galactosylation is reduced under decreased concentrations of dissolved oxygen (Kunkel et al. (1998). *J Biotechnol.* 62:55-71). Supplementing the medium with more than 20 mM N-acetylglucosamine can also induce new antibody glycoforms (Tachibana et al. (1992). *Biochem Biophys Res Commun.* 189:625-32; Tachibana et al. (1996) *In Vitro Cell Dev Biol Anion.* 32:178-183). Glucocorticoid hormones and interleukin 6 are involved in the modulation of protein glycosylation (Canellada and Margni (2002) *Hybrid Hybridomics* 21:203). Other factors which influence glycosylation include, for example, changes in the pH of culture medium and the availability of precursors and nutrients.

Therefore, selection of the cell line and cell culture conditions can have a big influence on the glycosylation pattern.

Besides enzymatic modifications and recombinant productions, mutagenesis, especially site-directed mutagenesis, of the target protein can be applied to modify its glycosylation pattern. Existing glycosylation sites can be removed with this technique. Mutations can be introduced to single amino acid residues to minimize the effect of the substitution on the conformation of the antibody or fragment, which may lead to a reduction of antigen affinity or other unwanted characteristic changes of the antibody or fragment (e.g., an increase of immunogenicity or a decrease of solubility). The methods for site-directed mutagenesis are well-known to a person skilled in the art, including the Zoller and Smith method (Zoller and Smith (1987) *Methods Enzymol.* 154: 329-50).

In some embodiments, the antibody or antigen-binding fragment thereof having an altered glycosylation pattern produces beneficial results. In some embodiments, the beneficial result may include, for example, an increased purity or homogeneity of the isolated or purified antibodies or antigen-binding fragments thereof. In a preferred embodiment, the glycosylation of an antibody or antigen-binding fragment thereof is decreased as compared to an unmodified antibody (such as the TA106 originated antibody or corresponding full length antibody) or fragment thereof. In some embodiments, the glycosylation of the target antibody or antigen-binding fragment thereof is decreased to 90, 80, 70, 60, 50, 40, 30, 20, 10, or 0% of the original glycosylation. In a preferred embodiment, the glycosylation of the target antibody or antigen-binding fragment thereof is decreased to at least 50%, i.e., to at least 50, 45, 40, 35, 30, 25, 20, 15, 10, 5, or 0% of the glycosylation in an unmodified antibody (such as the TA106 originated antibody or corresponding full length antibody) or fragment thereof. In a preferred embodiment, the glycosylation of the target antibody or antigen-binding fragment thereof is completely eliminated after the modification.

In some embodiments, the modification of the glycosylation pattern of the instant antibody or antigen-binding fragment thereof is achieved by introducing at least one mutation to the polynucleotide encoding the instant antibody or antigen-binding fragment thereof. In one embodiment, the at least one mutation is achieved by site-specific mutagenesis or other methods known in the art. In one embodiment, the at least one mutation changes at least one existing potential glycosylation site. The at least one mutation may, for example, be a mutation to the polynucleotide sequence encoding the existing potential glycosylation site, or a polynucleotide sequence encoding a polypeptide outside of the existing potential glycosylation site. In the former case, such a mutation may, for example, directly destroy the potential glycosylation pattern, resulting in a decrease or loss of glycosylation. In the latter case, such a mutation may, for example, change the local protein conformation (e.g., disrupt the accessibility to required glycosylation enzymes), resulting in a decrease or inhibition of glycosylation. In one embodiment, the at least one mutation eliminates at least one existing potential glycosylation site. In some embodiments, the existing glycosylation site is an N-glycosylation site. In one embodiment, the N-glycosylation site comprises a linear amino acid sequence of Asn-X-Ser (SEQ ID NO: 12), wherein X is any amino acid other than Pro. In another embodiment, the N-glycosylation site comprises a linear amino acid sequence of Asn-X-Thr (SEQ ID NO: 13), wherein X is any amino acid other than Pro. In some embodiments, the existing glycosylation site is an O-glycosylation site. In one embodiment, the O-glycosylation site comprises a linear amino acid sequence of Thr-X-X-Pro (SEQ ID NO: 14), wherein X is any amino acid. In another embodiment, the O-glycosylation site comprises a linear amino acid sequence of Ser-X-X-Pro (SEQ ID NO: 15), wherein X is any amino acid.

In some embodiments, the instant TA106-originated antibody, corresponding full length antibody, or antigen-binding fragment thereof is mutated to change its glycosylation pattern. In one embodiment, the antibody or fragment thereof has at least one potential glycosylation site on its light chain. In another embodiment, the antibody or fragment thereof has at least one potential glycosylation site on its heavy chain. In yet another embodiment, the antibody or fragment thereof has at least two potential glycosylation sites on both light chain and heavy chain. In one preferred embodiment, the potential glycosylation sites include $Asn^{31}Ser^{32}Ser^{33}$ in the CDR1 region of the light chain sequence as depicted in SEQ ID NO: 1. In one embodiment, the $Asn^{31}$ is replaced by another amino acid. In one preferred embodiment, the $Asn^{31}$ is replaced by at least one amino acid of Gln, Glu, or Asp. In another preferred embodiment, the $Asn^{31}$ is replaced by at least one amino acid of Gln. In another embodiment, the $Ser^{33}$ is replaced by another amino acid. In one preferred embodiment, the $Ser^{33}$ is replaced by at least one amino acid of Ala, Gly or His. In another preferred embodiment, the $Ser^{33}$ is replaced by at least one amino acid of Ala.

In one aspect, the instant disclosure provides a modified humaneered antibody (for example, modified based on the TA106 originated antibody or corresponding full length antibody) or antigen-binding fragment thereof. In one embodiment, the humaneered antibody or antigen-binding fragment thereof is modified to change its glycosylation pattern. In one preferred embodiment, at least one potential glycosylation site on the antibody or fragment is eliminated. In some preferred embodiments, the modified antibody or fragment maintains an equivalent or compatible antigen-binding activity as the original antibody or fragment. In one preferred embodiment, the antigen is factor B. In one embodiment, the modified antibody or antigen-binding fragment thereof has an affinity to factor B at least 50% of the affinity of the unmodified antibody (for example, the TA106 originated antibody or corresponding full length antibody) or antigen-binding fragment thereof. In one preferred embodiment, the modified antibody or antigen-binding fragment thereof has an affinity to factor B at least 50, 55, 60, 65, 70, 75, 80, 85, 90, 95, 100, 105, 110, 115, 120, 125, 130, 135, 140, 145, 150% or even higher of the affinity of the unmodified antibody or antigen-binding fragment thereof. The affinity can be measured, for example, by competition binding assay, function assay (e.g., hemolytic assay), or other assays described in the instant disclosure or known in the art.

In another aspect, the instant invention provides a nucleic acid comprising a sequence encoding the disclosed antibody or antigen-binding fragment thereof.

In another aspect, the instant invention provides an expression vector comprising a nucleic acid comprising a sequence encoding the disclosed antibody or antigen-binding fragment thereof. The expression vector can be any vector known in the art, e.g., plasmids. In one embodiment, the expression vector further comprises a leader sequence.

In another aspect, the instant invention provides a host cell (e.g., a recombinant host cell) comprising an expression vector comprising a nucleic acid comprising a sequence encoding the disclosed antibody or antigen-binding fragment thereof. The host cell can be any cell known in the art, e.g., bacterial cells, yeast cells, insect cells, mammalian cells, etc.

In another aspect, the instant invention provides a method for producing the disclosed antibody or antigen-binding fragment thereof, wherein the method comprises the steps of:

i) introducing at least one mutation into the polynucleotide sequence encoding the parent humaneered antibody or antigen-binding fragment thereof, wherein the mutation eliminates an existing potential glycosylation site on the parent antibody or antigen-binding fragment thereof; and ii) expressing the mutated polynucleotide in a cell to produce the antibody or antigen-binding fragment thereof.

In one embodiment, the method comprises a mutation resulting in an amino acid substitution that eliminates an existing potential glycosylation site on the parent antibody or antigen-binding fragment thereof. In another embodiment, the parent antibody or antigen-binding fragment thereof comprises a light chain Complementarity Determining Region 1 (CDR1) sequence comprising residues 24 through 40 of SEQ ID NO: 1, wherein the N-glycosylation site is $Asn^{31}Ser^{32}Ser^{33}$ in the CDR1 of SEQ ID NO: 1.

In another aspect, the instant disclosure provides a method of treating a disease or disorder in which activation of the alternative complement pathway plays a role, wherein the method comprises administering the instant humaneered anti-factor B antibody or antigen-binding fragment thereof with a modified glycosylation pattern to an animal that has, or is at risk of developing, said disease or disorder. In one embodiment, the disease or disorder is airway hyperresponsiveness ("AHR") or airway inflammation. In another embodiment, the instant humaneered anti-factor B antibody or antigen-binding fragment thereof is administered to the animal in an amount effective to reduce AHR or airway inflammation in the animal as compared to before administration of the antibody or antigen-binding fragment thereof. In another embodiment, the AHR or airway inflammation is associated with a disease selected from the group consisting of: asthma, chronic obstructive pulmonary disease ("COPD"), allergic bronchopulmonary aspergillosis, hypersensitivity pneumonia, eosinophilic pneumonia, emphysema, bronchitis, allergic bronchitis bronchiectasis, cystic fibrosis, tuberculosis, hypersensitivity pneumonitis, occupational asthma, sarcoid, reactive airway disease syndrome, interstitial lung disease, hyper-eosinophilic syndrome, rhinitis, sinusitis, exercise-induced asthma, pollution-induced asthma, cough variant asthma, parasitic lung disease, respiratory syncytial virus ("RSV") infection, parainfluenza virus ("PIV") infection, rhinovirus ("RV") infection, and adenovirus infection. In a preferred embodiment, the AHR or airway inflammation is associated with allergic inflammation. In another preferred embodiment, the AHR or airway inflammation is associated with asthma. In another preferred embodiment, the AHR or airway inflammation is associated with COPD. In some embodiments, the animal receiving the treatment is a non-human mammal. In other embodiments, the animal receiving the treatment is a human.

In another aspect, the instant disclosure further provides a method of selectively inhibiting activation of the alternative complement pathway in an animal that has, or is at risk of developing, a condition or disease in which activation of the alternative complement pathway contributes to the condition or disease, exacerbates at least one symptom of the condition or disease, or causes the condition or disease, wherein the method comprises administering the humaneered anti-factor B antibody or antigen-binding fragment thereof with a modified glycosylation pattern, to an animal in need thereof. In some embodiments, the animal receiving the treatment is a non-human mammal. In other embodiments, the animal receiving the treatment is a human.

In another aspect, the instant disclosure further provides a pharmaceutical composition comprising an effective amount of the instant humaneered anti-factor B antibody or antigen-binding fragment thereof with a modified glycosylation pattern, and a pharmaceutically acceptable carrier.

Methods Relating to Certain Embodiments of the Invention

Certain embodiments of the present invention relate to methods of treating diseases or disorders in which activation of the alternative complement pathway plays a role. Such methods involve administering a humaneered variant of mAb 1379 as described above, wherein the glycosylation site on the light chain has been varied and optionally further wherein the N-terminal amino acid residue of the heavy chain is a glutamic acid residue instead of a glutamine residue, or antigen-binding fragments thereof, to a human. The variation of the glycosylation site is preferably N31Q or S33A. These antibodies are for administration to an individual that has, or is at risk of developing, a disease in which activation of the alternative complement pathway plays a role. In one aspect, the humaneered antibody variants, and antigen-binding fragments thereof, are administered by a route selected from the group consisting of oral, nasal, topical, inhaled, intratracheal, transdermal, rectal and parenteral routes. In another aspect, the humaneered antibody variants, and antigen-binding fragments thereof, are administered with a pharmaceutically acceptable carrier selected from the group consisting of: a dry, dispersible powder; anhydrous ethanol; small capsules; liposomes; a nebulized spray; and an injectable excipient. In another aspect, the humaneered variants, and antigen-binding fragments thereof, are administered in a carrier or device selected from the group consisting of: anhydrous ethanol; a dry powder inhalation system; ultrasonic inhalation system; a pressurized metered dose inhaler; and a metered solution device. In another aspect, the humaneered antibody variants, and antigen-binding fragments thereof, are administered in an amount effective to treat the disease or disorder in which activation of the alternative complement pathway plays a role. In still other aspects, the humaneered antibody variants, and antigen-binding fragments thereof, are administered alone or in combination with another agent selected from the group consisting of: corticosteroids, β-agonists (long or short acting), leukotriene modifiers, antihistamines, phosphodiesterase inhibitors, sodium cromoglycate, nedocromil, theophylline, cytokine antagonists, cytokine receptor antagonists, anti-IgE, and inhibitors of T cell function.

Still other embodiments of the present invention relate to a method to reduce or prevent airway hyperresponsiveness (AHR) or airway inflammation in an individual. The method includes the step of administering a humaneered variant of mAb 1379 as described above, or mutated version thereof wherein the N-terminal amino acid residue of the heavy chain is a glutamic acid residue instead of a glutamine residue, or antigen-binding fragments thereof, wherein the variant humaneered antibody has an N31Q or S33A mutation, or antigen-binding fragment thereof, to an individual that has, or is at risk of developing, airway hyperresponsiveness associated with inflammation or airway inflammation. In one aspect, the humaneered variant of mAb 1379, or antigen-binding fragment thereof, or the mutated antibody or antigen-binding fragment thereof, is administered by a route selected from the group consisting of oral, nasal, topical, inhaled, intratracheal, transdermal, rectal and parenteral routes. In another aspect, the humaneered variant of mAb 1379, or antigen-binding fragment thereof, or the mutated antibody or antigen-binding fragment thereof, is administered to the animal in an amount effective to measurably reduce airway hyperresponsiveness in the individual as compared to prior to administration of the antibody or antigen binding fragment. In another aspect, the humaneered variant of mAb 1379 or antigen-binding fragment thereof, or the mutated antibody or antigen-binding fragment thereof, is administered to the individual in an amount effective to measurably reduce airway hyperresponsiveness in the individual as compared to a level of airway hyperresponsiveness in a population of individuals having inflammation wherein the antibody or antigen binding fragment was not administered. In another aspect, the humaneered variant of mAb 1379 or antigen-binding fragment thereof, or the mutated antibody or antigen-binding fragment thereof, is administered with a pharmaceutically acceptable carrier selected from the group consisting of: a dry, dispersible powder; anhydrous ethanol; small capsules; liposomes; a nebulized spray; and an injectable excipient. In another aspect, the humaneered variant of mAb 1379 or antigen-binding fragment thereof, or the mutated antibody or antigen-binding fragment thereof, is administered in a carrier or device selected from the group consisting of: anhydrous ethanol; a dry powder inhalation system; ultrasonic inhalation system; a pressurized metered dose inhaler; and a metered solution device.

In yet another aspect, the humaneered variant of mAb 1379 or antigen-binding fragment thereof, or the mutated antibody or antigen-binding fragment thereof, is administered to an individual in conjunction with an agent selected from the group consisting of: corticosteroids, β-agonists (long or short acting), leukotriene modifiers, antihistamines, phosphodiesterase inhibitors, sodium cromoglycate, nedocromil, theophylline, cytokine antagonists, cytokine receptor antagonists, anti-IgE, and inhibitors of T cell function. In yet another aspect, the airway hyperresponsiveness or airway inflammation is associated with a disease selected from the group consisting of asthma, chronic obstructive pulmonary disease (COPD), allergic bronchopulmonary aspergillosis, hypersensitivity pneumonia, eosinophilic pneumonia, emphysema, bronchitis, allergic bronchitis bronchiectasis, cystic fibrosis, tuberculosis, hypersensitivity pneumonitis, occupational asthma, sarcoid, reactive airway disease syndrome, interstitial lung disease, hyper-eosinophilic syndrome, rhinitis, sinusitis, exercise-induced asthma, pollution-induced asthma, cough variant asthma, parasitic lung disease, respiratory syncytial virus (RSV) infection, parainfluenza virus (PIV) infection, rhinovirus (RV) infection and adenovirus infection. In one aspect, the airway hyperresponsiveness is associated with allergic inflammation. The method of the present invention can be administered, in a preferred embodiment, to mammals and, more preferably, to humans.

Another embodiment of the present invention relates to a method to reduce or prevent airway hyperresponsiveness (AHR) or airway inflammation in an individual. The method includes the step of administering a reagent that selectively inhibits the alternative complement pathway to an individual that has, or is at risk of developing, airway hyperresponsiveness associated with inflammation or airway inflammation. In certain aspects, that reagent is a humaneered variant of mAb 1379, or mutated version thereof wherein the N-terminal amino acid residue of the heavy chain is a glutamic acid residue instead of a glutamine residue, or antigen-binding fragments thereof. In some aspects, that reagent is a mutated humaneered anti-factor B antibody, such as TA106 N31Q or TA106 S33A, corresponding full length antibody, or antigen-binding fragment thereof.

Formulations or Compositions Relating to Certain Embodiments of the Invention

Certain embodiments of the humaneered anti-factor B antibody variants of the present invention include a formulation or composition comprising an inhibitor of the alternative complement pathway and, particularly, a selective inhibitor of the alternative complement pathway as described herein. The formulations or compositions can be used in any of the methods described herein and with any of the reagents described herein (e.g., the humaneered factor B antibody variants N31Q or S33A, or mutated versions thereof wherein the N-terminal amino acid residue of the heavy chain is a glutamic acid residue instead of a glutamine residue, or antigen-binding fragment thereof as described herein). In one embodiment, the composition is useful for reducing or preventing airway hyperresponsiveness in an animal. In another embodiment, the composition is useful for reducing or preventing ischemia-reperfusion injury in an animal. In yet another embodiment, the composition is useful for treating or preventing a condition or disease by selective inhibition of the alternative complement pathway. The formulation comprises: (a) an inhibitor of the alternative complement pathway as described herein; and (b) a pharmaceutically acceptable carrier.

In one embodiment, the formulation or composition can include one or more additional agents, such as an anti-inflammatory agent suitable for reducing inflammation in an animal that has, or is at risk of developing, airway hyperresponsiveness, and particularly, airway hyperresponsiveness associated with inflammation. The anti-inflammatory agent can be any anti-inflammatory agent suitable for use in reducing inflammation in a patient that has an inflammatory condition associated with airway hyperresponsiveness, including, but not limited to: corticosteroids (oral, inhaled and injected), β-agonists (long or short acting), leukotriene modifiers (inhibitors or receptor antagonists), cytokine or cytokine receptor antagonists, anti-IgE antibodies, phosphodiesterase inhibitors, sodium cromoglycate, nedocromil, theophylline, and inhibitors of T cell function. Particularly preferred anti-inflammatory agents for use in the present formulation include corticosteroids, leukotriene modifiers, and cytokine or cytokine receptor antagonists.

In another embodiment, the formulation or composition can include one or more additional agents, such as an additional agent suitable for preventing or reducing ischemia-reperfusion injury in an animal. Such agents include, but are not limited to, anti-inflammatory agents; or inhibitors of oxidation and free radical damage.

In another embodiment, the formulation or composition can include one or more additional agents, such as an additional agent suitable for treatment of another disease or condition associated with activation of the alternative complement pathway.

According to the present invention, a "pharmaceutically acceptable carrier" includes pharmaceutically acceptable excipients and/or pharmaceutically acceptable delivery vehicles, which are suitable for use in the administration of a formulation or composition to a suitable in vivo site. A suitable in vivo site is preferably any site wherein the alternative complement pathway can be inhibited. In one preferred embodiment, when the patient has or is at risk of developing airway hyperresponsiveness and/or airway inflammation, a suitable in vivo site is preferably in the lung tissue or airways. Other preferred in vivo sites include other tissues or organs where conditions associated with the alternative complement pathway may be centered. In another preferred embodiment, a suitable in vivo site is any site where ischemia-reperfusion injury occurs, such as in the heart or pulmonary system, central nervous system, limbs or digits, internal organs (e.g., lung, liver or intestine), or in any transplanted organ or tissue. Preferred pharmaceutically acceptable carriers are capable of maintaining an agent used in a formulation of the invention in a form that, upon arrival of the agent at the target site in a patient, the agent is capable of acting on its target (e.g., a protein that is a component of the alternative complement pathway), preferably resulting in a therapeutic benefit to the patient.

Suitable excipients for use in the present invention include excipients or formularies that transport or help transport, but do not specifically target a composition to a cell or tissue (also referred to herein as non-targeting carriers). Examples of pharmaceutically acceptable excipients include, but are not limited to, water, phosphate buffered saline ("PBS"), Ringer's solution, dextrose solution, serum-containing solutions, Hank's Balanced Salt Solution ("HBSS"), and other aqueous physiologically balanced solutions, oils, esters and glycols. Aqueous carriers can contain suitable auxiliary substances required to approximate the physiological conditions of the recipient, for example, by enhancing chemical stability and isotonicity. Suitable auxiliary substances include, for example, sodium acetate, sodium chloride, sodium lactate, potassium chloride, calcium chloride, and other substances used to produce phosphate buffer, Tris buffer, and bicarbonate buffer. Auxiliary substances can also include preservatives, such as thimerosal, m- or o-cresol, formalin and benzyl alcohol. Formulations of the present invention can be sterilized by conventional methods and/or lyophilized.

One type of pharmaceutically acceptable carrier includes a controlled-release formulation that is capable of slowly releasing a composition of the present invention into an animal. As used herein, a controlled-release formulation comprises an agent of the present invention in a controlled-release vehicle. Suitable controlled-release vehicles include, but are not limited to, biocompatible polymers, other polymeric matrices, capsules, microcapsules, microparticles, bolus preparations, osmotic pumps, diffusion devices, liposomes, liposheres, and transdermal delivery systems. Other suitable carriers include any carrier that can be bound to or incorporated with the agent that extends the half-life of the agent to be delivered. Such a carrier can include any suitable protein carrier or even a fusion segment that extends the half-life of a protein when delivered in vivo. Suitable delivery vehicles have been previously described herein, and include, but are not limited to liposomes, viral vectors or other delivery vehicles, including ribozymes. Natural lipid-containing delivery vehicles include cells and cellular membranes. Artificial lipid-containing delivery vehicles include liposomes and micelles. As discussed above, a delivery vehicle of the present invention can be modified to target to a particular site in a patient, thereby targeting and making use of an inhibitory agent at that site. Suitable modifications include manipulating the chemical formula of the lipid portion of the delivery vehicle and/or introducing into the vehicle a targeting agent capable of specifically targeting a delivery vehicle to a preferred site, for example, a preferred cell type. Other suitable delivery vehicles include gold particles, poly-L-lysine/DNA-molecular conjugates, and artificial chromosomes.

In one embodiment, an agent useful in the present methods is administered in a formulation suitable for pulmonary or nasal delivery, and particularly, aerosol delivery, also referred to herein as an aerosolized formulation. Such a route of delivery is particularly useful in the method to prevent or inhibit AHR and/or airway inflammation in a patient, but can be used in other conditions when delivery to the lung or airways is desired. In addition, these formulations are particularly useful for the delivery of antibodies. Such a formulation generally includes a carrier, and preferably, a pharmaceutically acceptable carrier. Carriers that are particularly useful for aerosol delivery according to the present invention include, but are not limited to: anhydrous ethanol; dry, dispersible powders; small capsules (e.g., microcapsules or microparticles); liposomes; injectable excipients; and nebulized sprays. Anhydrous ethanol for the delivery of proteins and peptides is described, for example, in Choi et al., Proc. Nat'l Acad. Sci. USA 98(20):11103-11107 (2001). Dry, dispersible powders suitable for aerosolized delivery of agents are described in detail, for example, in U.S. Pat. No. 6,165,463, incorporated herein by reference in its entirety (See also products from Inhale Therapeutic Systems, Inc., now Nektar, and Quadrant Technology). Suitable liposomes for use in aerosols include any liposome, and particularly, any liposome that is sufficiently small to be delivered by aerosol in the method of the invention. Microcapsules and microparticles are known in the art. For example, Alliance Pharmaceutical Corporation has a particle engineering technology called PulmoSphere, in which microparticles are prepared by a proprietary spray-drying process and are designed to be both hollow and porous. A product by Ventolin consists of micronized albuterol (free base) particles suspended in a mixture of CFC-based propellants. Proventil HFA contains micronized albuterol sulfate and a small percentage of an ethanol co-solvent to solubilize the stabilizing oleic acid surfactant. Incorporation of drugs into liposomes has several advantages for aerosol delivery. Because liposomes are relatively insoluble, the retention time of some drugs in the lung can be prolonged for increased efficacy. Liposomes are also taken up primarily by phagocytic cells which make them particularly suitable for delivery of certain drugs. Devices for delivery of aerosolized formulations include, but are not limited to, pressurized metered dose inhalers ("MDI"), dry powder inhalers ("DPI"), metered solution devices ("MSI"), and ultrasonic inhalers, and include devices that are nebulizers and inhalers. Various agents can be used in formulations delivered by such devices as suspension aids and solubilizers that are particularly useful for the delivery of proteins (e.g., oligolactic acid, acyl-amide acids, and mono-functionalized M-PEGS; see, e.g., McKenzie and Oliver;

2000, Formulating Therapeutic Proteins and Peptides in Pressurized Metered Dose Inhalers For Pulmonary Delivery, 3M Health Care Ltd., Morley Street, Loughborough, Leicestershire LE11 1EP, UK).

A pharmaceutically acceptable carrier which is capable of targeting is herein referred to as a "targeting delivery vehicle." Targeting delivery vehicles of the present invention are capable of delivering a formulation, including an inhibitory agent, to a target site in a patient. A "target site" refers to a site in a patient to which one desires to deliver a therapeutic formulation. For example, a target site can be any cell or tissue which is targeted by an antibody of the present invention, or by direct injection or delivery using liposomes, viral vectors or other delivery vehicles, including ribozymes. A delivery vehicle or antibody of the present invention can be modified to target a particular site in an animal, thereby targeting and making use of a particular compound, antibody, protein, or nucleic acid molecule at that site. Suitable modifications include manipulating the chemical formula of the lipid portion of a delivery vehicle and/or introducing into the vehicle a compound capable of specifically targeting a delivery vehicle to a preferred site, for example, a preferred cell or tissue type. Specifically, targeting refers to causing a delivery vehicle to bind to a particular cell by the interaction of the compound in the vehicle to a molecule on the surface of the cell. Suitable targeting compounds include ligands capable of selectively (i.e., specifically) binding another molecule at a particular site. Examples of such ligands include antibodies, antigens, receptors and receptor ligands. Particularly useful examples include any ligands associated with the complement pathway (e.g., CR2, C3, C3d, C3dg, iC3b, C3b) or any ligands associated with the cell type, tissue type, or site in the animal to be treated. Manipulating the chemical formula of the lipid portion of the delivery vehicle can modulate the extracellular or intracellular targeting of the delivery vehicle. For example, a chemical can be added to the lipid formula of a liposome that alters the charge of the lipid bilayer of the liposome so that the liposome fuses with cells having particular charge characteristics.

One delivery vehicle useful for a variety of administration routes and agents is a liposome. A liposome is capable of remaining stable in an animal for a sufficient amount of time to deliver a nucleic acid molecule, or even a protein or antibody as described in the present invention, to a preferred site in the animal. According to the present invention, a liposome comprises a lipid composition that is capable of delivering a nucleic acid molecule, protein, or antibody as described in the present invention to a particular, or selected, site in an animal. A liposome according to the present invention comprises a lipid composition that is capable of fusing with the plasma membrane of the targeted cell to deliver its contents into a cell. Suitable liposomes for use with the present invention include any liposome. Preferred liposomes of the present invention include those liposomes typically used in, for example, gene delivery methods known to those of skill in the art. More preferred liposomes comprise liposomes having a polycationic lipid composition and/or liposomes having a cholesterol backbone conjugated to polyethylene glycol. Complexing a liposome with a nucleic acid molecule, protein or antibody of the present invention can be achieved using methods standard in the art.

In accordance with the present invention, determination of acceptable protocols to administer an agent, composition or formulation, including the route of administration and the effective amount of an agent to be administered to an animal, can be accomplished by those skilled in the art. An agent of the present invention can be administered in vivo or ex vivo. Suitable in vivo routes of administration can include, but are not limited to, oral, nasal, inhaled, topical, intratracheal, transdermal, rectal, and parenteral routes. Preferred parenteral routes can include, but are not limited to, subcutaneous, intradermal, intravenous, intramuscular, and intraperitoneal routes. Preferred topical routes include inhalation by aerosol (i.e., spraying) or topical surface administration to the skin of an animal. Preferably, an agent is administered by nasal, inhaled, intratracheal, topical, or systemic routes (e.g., intraperitoneal, intravenous). The term "ex vivo" refers to performing part of the administration step outside of the patient. Preferred routes of administration for antibodies include parenteral routes and aerosol/nasal/inhaled routes.

Intravenous, intraperitoneal, and intramuscular administrations can be performed using methods standard in the art. Aerosol (inhalation) delivery can be performed using methods standard in the art (see, e.g., Stribling et al., Proc. Nat'l Acad. Sci. USA 189:11277-11281 (1992), which is incorporated herein by reference in its entirety). Carriers suitable for aerosol delivery are described above. Devices for delivery of aerosolized formulations include, but are not limited to, pressurized metered dose inhalers ("MDI"), dry powder inhalers ("DPI"), and metered solution inhalers ("MSI"), and include devices that are nebulizers and inhalers. Oral delivery can be performed by complexing a therapeutic composition of the present invention to a carrier capable of withstanding degradation by digestive enzymes in the gut of an animal. Examples of such carriers include plastic capsules or tablets, such as those known in the art. Direct injection techniques are particularly useful for administering a recombinant nucleic acid molecule to a cell or tissue that is accessible by surgery, and particularly, on or near the surface of the body. Administration of a composition locally within the area of a target cell refers to injecting the composition centimeters and preferably, millimeters from the target cell or tissue.

A preferred single dose of an agent, including proteins, small molecules and antibodies, for use in any method described herein, comprises between about 0.01 µg/kg and about 100 mg/kg body weight of an animal. A more preferred single dose of an agent comprises between about 1 µg/kg and about 100 mg/kg body weight of an animal. An even more preferred single dose of an agent comprises between about 5 µg/kg and about 70 mg/kg body weight of an animal. An even more preferred single dose of an agent comprises between about 10 µg/kg and about 50 mg/kg body weight of an animal. A particularly preferred single dose of an agent comprises between about 0.01 mg/kg and about 10 mg/kg body weight of an animal, if the agent is delivered by aerosol. Another particularly preferred single dose of an agent comprises between about 1 mg/kg and about 100 mg/kg body weight of an animal, if the agent is delivered parenterally.

In one embodiment a suitable dose of an agent of the present invention for use in any method described herein is a dose effective to inhibit the expression or activity of at least one protein in the alternative complement pathway as described herein (e.g., factor B, factor D or properdin), as compared to in the absence of the administration of the agent. Methods of measuring the expression or biological activity of a protein are known in the art and include, for example, Northern blotting, Western blotting, real time RT-PCR, and the like. In another embodiment, a suitable dose of an agent of the present invention is a dose that measurably inhibits the alternative complement pathway of the invention. Activation of complement and inhibition thereof can be measured using techniques/assays that are well-known in the art. For example, one can perform an in vitro analysis of C3 deposition on zymosan A particles as described in the examples of co-pending U.S Patent Application Publication No. US-2005/0260198 A1, which is incorporated herein by reference. One can also test the ability of the agent to inhibit lysis of unsensitized erythrocytes by human serum. Extrapolation of in vitro results to in vivo dosages based on these assays is within the ability of those of skill in the art.

In humans, it is known in the art that, using conventional methods for aerosol delivery, only about 10% of the delivered solution typically enters the deep airways, even using an inhaler. If the aerosolized delivery is by direct inhalation, one may assume a dosage of about 10% of that administered by nebulization methods. Finally, one of skill in the art will readily be capable of converting a mouse dosage to a human dosage using allometric scaling. Essentially, a scale of dosage from mouse to human is based on the clearance ratio of a compound and the body surface of the mouse. The conversion for mg/kg is one twelfth of the "no observed adverse event level" ("NOAEL") to obtain the concentration for human dosage. This calculation assumes that the elimination between mouse and human is the same, which is believed to be the case for antibodies.

Accordingly, a single dose of an antibody comprises between about 1 ng/kg and about 100 mg/kg body weight of an animal. In some embodiments, a preferred single dose of an antibody comprises between about 1 ng/kg and about less than 10 mg/kg body weight of an animal. A more preferred single dose of an antibody comprises between about 20 ng/kg and about 6 mg/kg body weight of the animal. An even more preferred single dose of an antibody, particularly when the antibody formulation is delivered by nebulization, comprises between about 20 ng/kg and about 6 mg/kg body weight of the animal, and more preferably, between about 20 ng/kg and about 5 mg/kg, and more preferably, between about 20 ng/kg and about 4 mg/kg, and more preferably, between about 20 ng/kg and about 3 mg/kg, and more preferably, between about 20 ng/kg and about 2 mg/kg, and more preferably, between about 20 ng/kg and about 1 mg/kg, and more preferably, between about 20 ng/kg and about 500 μg/kg body weight of the animal.

Another preferred single dose of an antibody, particularly when the antibody formulation is delivered by nebulization, comprises between about 200 ng/kg and about 100 mg/kg body weight of the animal, and more preferably, comprises between about 200 ng/kg and about 60 mg/kg body weight of the animal, and more preferably, comprises between about 200 ng/kg and about 10 mg/kg body weight of the animal, and more preferably, comprises between about 200 ng/kg and about 6 mg/kg body weight of the animal, and more preferably, between about 200 ng/kg and about 5 mg/kg, and more preferably, between about 200 ng/kg and about 4 mg/kg, and more preferably, between about 200 ng/kg and about 3 mg/kg, and more preferably, between about 200 ng/kg and about 2 mg/kg, and more preferably, between about 200 ng/kg and about 1 mg/kg, and more preferably, between about 200 ng/kg and about 500 μg/kg body weight of the animal.

Another preferred single dose of an antibody, particularly when the antibody formulation is delivered by direct inhalation from an inhaler, comprises between about 2 ng/kg and about 1 mg/kg body weight of the animal, and more preferably, between about 2 ng/kg and about 500 μg/kg, and more preferably, between about 2 ng/kg and about 100 μg/kg, and more preferably, between about 2 ng/kg and about 50 μg/kg, and more preferably, between about 2 ng/kg and about 10 μg/kg, and more preferably, between about 2 ng/kg and about 5 μg/kg, and more preferably, between about 2 ng/kg and about 2.5 μg/kg, and more preferably, between about 2 ng/kg and about 1 μg/kg body weight of the animal.

In another embodiment, the antibody is administered at a dose of less than about 5 mg antibody per milliliter of formulation, and preferably, less than about 2.5 mg antibody per milliliter of formulation, and more preferably, less than about 1 mg antibody per milliliter of formulation, and more preferably, less than about 500 μg antibody per milliliter of formulation, and more preferably, less than about 400 μg antibody per milliliter of formulation, and more preferably, less than about 300 μg antibody per milliliter of formulation, and more preferably, less than about 200 μg antibody per milliliter of formulation, and more preferably, less than about 100 μg antibody per milliliter of formulation, and even more preferably, between about 50 μg antibody and about 100 μg antibody per milliliter of formulation.

With more particular regard to the method of reducing or preventing airway hyperresponsiveness and/or airway inflammation or a condition or disease related thereto, a suitable single dose of an inhibitory agent to administer to an animal is a dose that is capable of reducing or preventing airway hyperresponsiveness and/or airway inflammation, or reducing at least one other symptom of a disease to be treated (e.g., asthma), in an animal when administered one or more times over a suitable time period. When the patient has or is at risk of developing AHR, a suitable single dose of an agent comprises a dose that improves AHR by a doubling dose of a provoking agent or improves the static respiratory function of an animal.

According to the method of the present invention, an effective amount of an agent that inhibits AHR (for example, the humaneered anti-factor B antibody variants alone or in combination with an additional agent) for administration to an animal comprises an amount that is capable of reducing airway hyperresponsiveness (AHR) or airway inflammation without being toxic to the animal. An amount that is toxic to an animal comprises any amount that causes damage to the structure or function of an animal (i.e., poisonous).

In one embodiment of the present invention, in an animal that has AHR, an effective amount of an agent (for example, the humaneered anti-factor B antibody variants alone or in combination with an additional agent) for administration to an animal is an amount that measurably reduces AHR in the animal as compared to prior to administration of the agent. In another embodiment, an effective amount of an agent for administration to an animal is an amount that measurably reduces AHR in the animal as compared to a level of airway AHR in a population of animals with inflammation that is associated with AHR wherein the agent was not administered. The agent is preferably capable of reducing AHR in an animal, even when the agent is administered after the onset of the physical symptoms of AHR (i.e., after acute onset AHR). Most preferably, an effective amount of the agent is an amount that reduces the symptoms of AHR to the point where AHR is no longer detected in the patient. In another embodiment, an effective amount of the agent is an amount that prevents, or substantially inhibits the onset of AHR when the agent is administered prior to exposure of the patient to an AHR-provoking stimulus, such as an allergen, in a manner sufficient to induce AHR in the absence of the agent.

One of skill in the art will be able to determine that the number of doses of an agent (for example, the humaneered anti-factor B antibody variants alone or in combination with an additional agent) to be administered to an animal is dependent upon the extent of the airway hyperresponsiveness and the underlying condition of which AHR is a symptom, and the response of an individual patient to the treatment. In addition, the clinician will be able to determine the appropriate timing for delivery of the agent in a manner effective to reduce AHR in the animal. Preferably, the agent is delivered within 48 hours prior to exposure of the patient to an amount of an AHR provoking stimulus effective to induce AHR, and more preferably, within 36 hours, and more preferably within 24 hours, and more preferably within 12 hours, and more preferably within 6 hours, 5 hours, 4 hours, 3 hours, 2 hours, or 1 hour prior to exposure of the patient to an amount of AHR provoking stimulus effective to induce AHR. In one embodiment, the agent is administered as soon as it is recognized (i.e., immediately) by the patient or clinician that the patient has been exposed or is about to be exposed to an AHR provoking stimulus, and especially an AHR provoking stimulus to which the patient is sensitized (i.e., an allergen). In another embodiment, the agent is administered upon the first sign of development of AHR (i.e., acute onset AHR), and preferably, within at least 2 hours of the development of symptoms of AHR, and more preferably, within at least 1 hour, and more preferably within at least 30 minutes, and more preferably within at least 10 minutes, and more preferably within at least 5 minutes of development of symptoms of AHR. Symptoms of AHR and methods for measuring or detecting such symptoms have been described in detail above. Preferably, such administrations are given until signs of reduction of AHR appear, and then as needed until the symptoms of AHR are gone.

With particular regard to the method of inhibiting or preventing ischemia-reperfusion injury, an effective amount of an agent, and particularly an anti-factor B antibody or antigen binding fragment thereof (or antigen binding polypeptide), or a mutated anti-factor B antibody or antigen-binding fragment thereof, to administer to an animal is an amount that measurably inhibits histological damage, including oxidative damage or cell death, in the animal as compared to in the absence of administration of the agent. In the case of renal ischemia-reperfusion injury, an effective amount of an agent to administer to an animal is an amount that measurably inhibits increases in serum urea nitrogen or measurably decreases histologic injury to the tissues of the kidney of the animal as compared to in the absence of administration of the agent. A suitable single dose of an inhibitory agent to administer to an animal is a dose that is capable of reducing or preventing at least one symptom, type of injury, or resulting damage, from ischemia-reperfusion injury in an animal when administered one or more times over a suitable time period. Suitable doses of antibodies, including for various routes of administration, are described in detail above. In one aspect, an effective amount of an agent that inhibits ischemia-reperfusion injury to administer to an animal comprises an amount that is capable of inhibiting at least one symptom or damage caused by ischemia-reperfusion injury without being toxic to the animal.

EXAMPLES

The present invention will now be described with reference to the following specific, non-limiting examples.

Example 1

Mutagenesis of Humaneered Antibodies

The preparation and humaneering processes of the mouse anti-factor B antibody mAb 1379, as well as the amino acid sequences of and the functional analyses for the resulting humaneered anti-factor B antibodies or antigen-binding fragments thereof (e.g., TA106) originated from mAb 1379, are disclosed in U.S. patent application Ser. No. 12/049,233, filed Mar. 14, 2008, now U.S. Pat. No. 7,964,705, which is hereby incorporated by reference in its entirety. The following example illustrates a method to modulate the glycosylation pattern of the humaneered anti-factor B Fabs and monoclonal antibodies (TA106-originated). Specifically, a potential N-glycosylation site in the CDR1 region of the light chain of TA106 was eliminated by site-directed mutagenesis.

In certain embodiments, the $V_H$-region sequences are modified to replace an amino terminal glutamine (Q) residue (e.g., see SEQ ID NO: 9) with a glutamic acid (E) residue (e.g., see SEQ ID NO: 10). This change prevents cyclization of the glutamine (Q) residue and promotes a more uniform final product in manufacturing.

Specifically, TA106 has a putative N-linked glycosylation site (i.e., $N^{31}S^{32}S^{33}$) in its light chain CDR1 region (see SEQ ID NO: 6). To analyze the glycosylation pattern of TA106-derivative mAbs in CHO or other cell lines, two alternative TA106 light chains were prepared by standard site-directed mutagenesis methods known to a person of skill in the art, resulting in an N (asparagine)-to-Q (glutamine) mutation at residue 31 or an S (serine)-to-A (alanine) mutation at residue 33. Coding sequences (based on human germline gene sequences) for variant and wild type TA106 light chains were designed and synthesized for expression in CHO cells using the LONZA GS SELECTION SYSTEM® (Lonza, Basel, Switzerland). Full length human $IgG_{2/4}$mAb and $IgG_1$ Fab sequences were created by standard methods known to a person of skill in the art. For TA106, the $IgG_{2/4}$ full-length mAb and $IgG_1$ Fab were named as CLS011 and CLS014, respectively. For the TA106-derivative N31Q variant, the corresponding $IgG_{2/4}$ full-length mAb and $IgG_1$ Fab were named as CLS012 and CLS015, respectively. For the TA106-derivative S33A variant, the corresponding $IgG_{2/4}$ full-length mAb and $IgG_1$ Fab were named as CLS013 and CLS016, respectively.

For cell transfection and transient expression, plasmids containing $V_H$ and $V_L$ chains of different mAbs (i.e., pCLS011, pCLS012, pCLS013) were transiently transfected into CHO-K1 cells (Lonza) using several different transfection reagents and methods. As an exemplary transfection protocol with LIPOFECTAMINE™2000 (INVITROGEN™, Carlsbad, Calif.), CHO cells were seeded at 4.5× $10^5$ viable cell density (VCD) per mL in 35 mL DMEM (containing 10% heat inactivated FBS and 6 mM glutamine, CELLGRO® 25-005-CI, Lot#25005233, Manassas, Va.) two days before transfection. At the day of transfection, cell culture media were changed to 24 mL fresh DMEM (containing 10% heat inactivated FBS and 6 mM glutamine). About 23.8 µg of each of plasmid DNAs containing $V_H$ and $V_L$ sequences were mixed with about 2.947 mL DMEM (CELLGRO® Cat #: 15-013-CV, Lot#15013267) and incubated for 5 minutes. In addition, about 0.12 mL of LIPOFECTAMINE™ 2000 (INVITROGEN™ #11668-019) were mixed with about 2.88 mL DMEM (CELLGRO® Cat #: 15-013-CV, Lot#15013267) and incubated for 5 minutes. Then DNA solution and LIPOFECTAMINE™ solution were mixed and incubated for 25 minutes. The resulting 6 mL solution was added to CHO cells in 24 mL fresh DMEM in T175 flasks. The next day of transfection, cell culture media were changed to 35 mL CD CHO media (INVITROGEN™ #10743-029, Lot#883026) containing 6 mM glutamine. As an exemplary transfection protocol by electroporation, the same amount of plasmid DNAs were resuspended in 1 mL CD CHO media plus 6 mM glutamine and mixed with about 1×10⁷ CHOK1SV cells. The mixture was then transferred to a cuvette for electroporation with standard settings known to a person of skill in the art. The resulting cell suspension was mixed with about 200 mL CD CHO media with 6 mM glutamine and distributed among four T-15 flasks (50 mL per flask). As an exemplary transfection protocol by FREESTYLE™-Max reagent (INVITROGEN™ 16447-100), CHO cells were seeded at 4.5×10⁵ viable cell density (VCD) per mL in 30 mL FREESTYLE™ CHO media (containing 8 mM glutamine) or CD CHO media (containing 6 mM glutamine) two days before transfection. At the day of transfection, cells (VCD should be about 1.2-1.5×10⁶ cells/mL) were diluted to 1×10⁶ cells/mL in FREESTYLE™ CHO media (containing 8 mM glutamine) or CD CHO media (containing 6 mM glutamine). The same amount of plasmid DNAs containing $V_H$ and $V_L$ sequences was mixed with OPTI-PRO™ SFM media (INVITROGEN™, 12309-050, Lot#896719) and incubated for 10 minutes. The DNA solution was then mixed with FREESTYLE™ Max reagent (pre-incubated with OPTI-PRO™ SFM media for 10 minutes) and incubated further for 10 minutes. The total volume of 1.2 mL mixture was added to flasks and the cell culture media remained unchanged in the next day after transfection.

CHO cell culture media containing the expressed mAbs (i.e., CLS011, CLS012, and CLS013) were harvested 7-8 days post transfection. Antibodies were purified from cell culture supernatant with MABSELECT XTRA™ resin (GE Healthcare, Piscataway, N.J.) or HITRAP™ Protein A HP column (GE Healthcare). The purification protocol was adopted according to the manufacturer's recommendation and is also well known to a person of skill in the art. In one exemplary experiment, approximately 250-350 mL cell culture media supernatant for each mAb were collected and applied to one HITRAP™ Protein A HP column (GE Healthcare), according to the manufacturer's recommendation. The equilibration buffer contained 250 mM NaCl, 50 mM Glycine, pH 8. The elution buffer contained 150 mM NaCl, 100 mM Glycine, pH 3.2. Each mAb was purified using a unique column in a process as follows: 1 mL HITRAP™ column was washed with 10 column volumes (CV) H₂O to remove storage solution and then equilibrated with a minimum of 10 CV of equilibration buffer. Sample was then loaded at a flow rate of 1 mL/min. Following loading, the column was washed to baseline and then with a further 10 CV of equilibration buffer. Samples were eluted from the column with elution buffer and 0.5 mL fractions were collected. Following fractionation the column was washed with H₂O and stored in 20% ethanol at 4° C. Fractions were confirmed by UV Spectrophotometry at 280 nm and pooled, neutralized with 1 M Tris Base, and dialyzed against PBS. Note that since these mAbs all have an IgG₂/G₄ Fc region, they are very amenable to protein A purification. Following dialysis, elution fractions were filtered through a 0.22 μm filter and a sample was prepared for endotoxin testing. As the result, these samples were negative for endotoxin. Then the elution samples were quantified by UV Spectrophotometry at 280 nm, using extinction coefficients as determined by the Expasy Prot Param algorithm (see Gasteiger et al., Protein Identification and Analysis Tools on the ExPASy Server; in John M. Walker (ed.): The Proteomics Protocols Handbook, Humana Press (2005), pp. 571-607).

Figure 2:
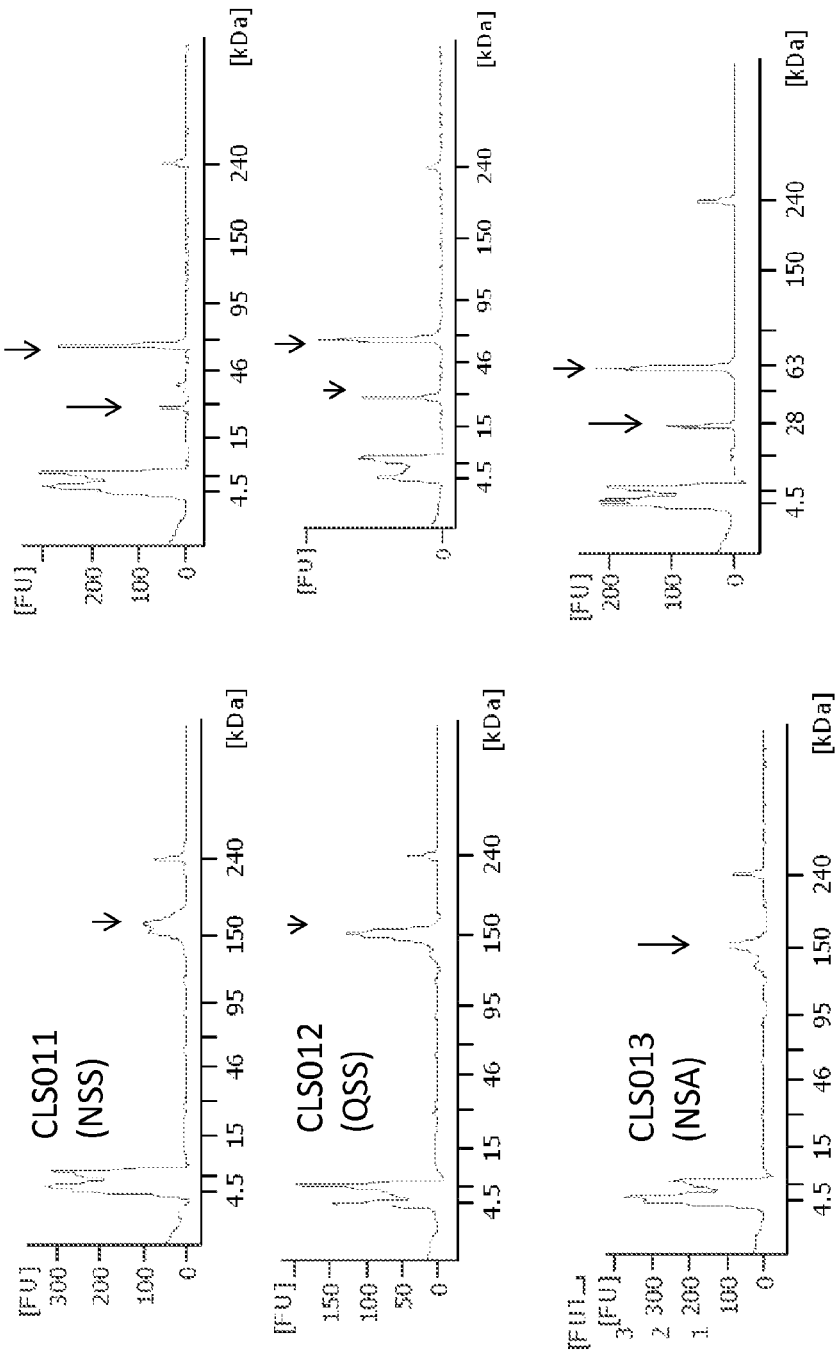
FIG. 2 depicts chromatographic traces of the same capillary electrophoresis result as in FIG. 1. The Y-axis represents the fluorescence units. The X-axis represents protein molecular weight in kDa. The left panels represent TA106 variant mAbs loaded as non-reduced samples and the arrows designate the full-length antibody. The right panels represent TA106 variant mAbs loaded as reduced samples and the arrows designate the heavy and light chains of the corresponding antibody.

The purified mAbs were further analyzed on an AGILENT™ protein chip 230 with an AGILENT™ bioanalyzer 2100 (AGILENT™ Technologies, Santa Clara, Calif.), according to the manufacturer's recommended protocol (e.g., as shown in the Protein 230 Kit, Part Number: G2938-90055, and in the AGILENT™ Protein 230 Kit Guide, Part Number: G2938-90054, AGILENT™ Technology). By using AGILENT™ protein chips, proteins in a sample can be separated by their sizes by means of electrophoresis in an interconnected set of microchannels. In this Example, mAbs were loaded and analyzed as reduced or non-reduced samples. The molecular weights of the whole mAbs (non-reduced) or heavy and light chains of mAbs (reduced) were then calculated based on their different retention times. As shown in FIGS. 1 and 2, CLS011 mAb, with a theoretical molecular weight of 149,403 Da, has a heavy chain of about 59 kDa and a light chain of about 26 kDa. CLS012 mAb, with a theoretical molecular weight of 149,431 Da, has a heavy chain of about 60 kDa and a light chain of about 26 kDa. CLS013 mAb, with a theoretical molecular weight of 149,371 Da, has a heavy chain of about 60 kDa and a light chain of about 27 kDa.

Liquid Chromatography Electrospray Ionization Time-of-Flight Mass Spectrometry (HPLC-ESI-ToF-MS) was used to acquire the glycosylation patterns and molecular weight data of TA106 and its variants expressed in CHO cells. In one exemplary experiment, AGILENT™ (Hewlett Packard) 1100 HPLC system and AGILENT™ LC/MSD ToF-MS system were used with the manufacturer's recommended protocol, e.g., with the flow rate of 50 μL per minute, column temperature at 60° C., UV reading at 215 nm, and m/z range at 750-5600. The injection volume can be calculated by:

$$\text{Injection Volume } (\mu L) = \frac{10 \ \mu g}{\text{protein concentration (mg/mL} = \mu g/\mu L)}$$

Figure 3:
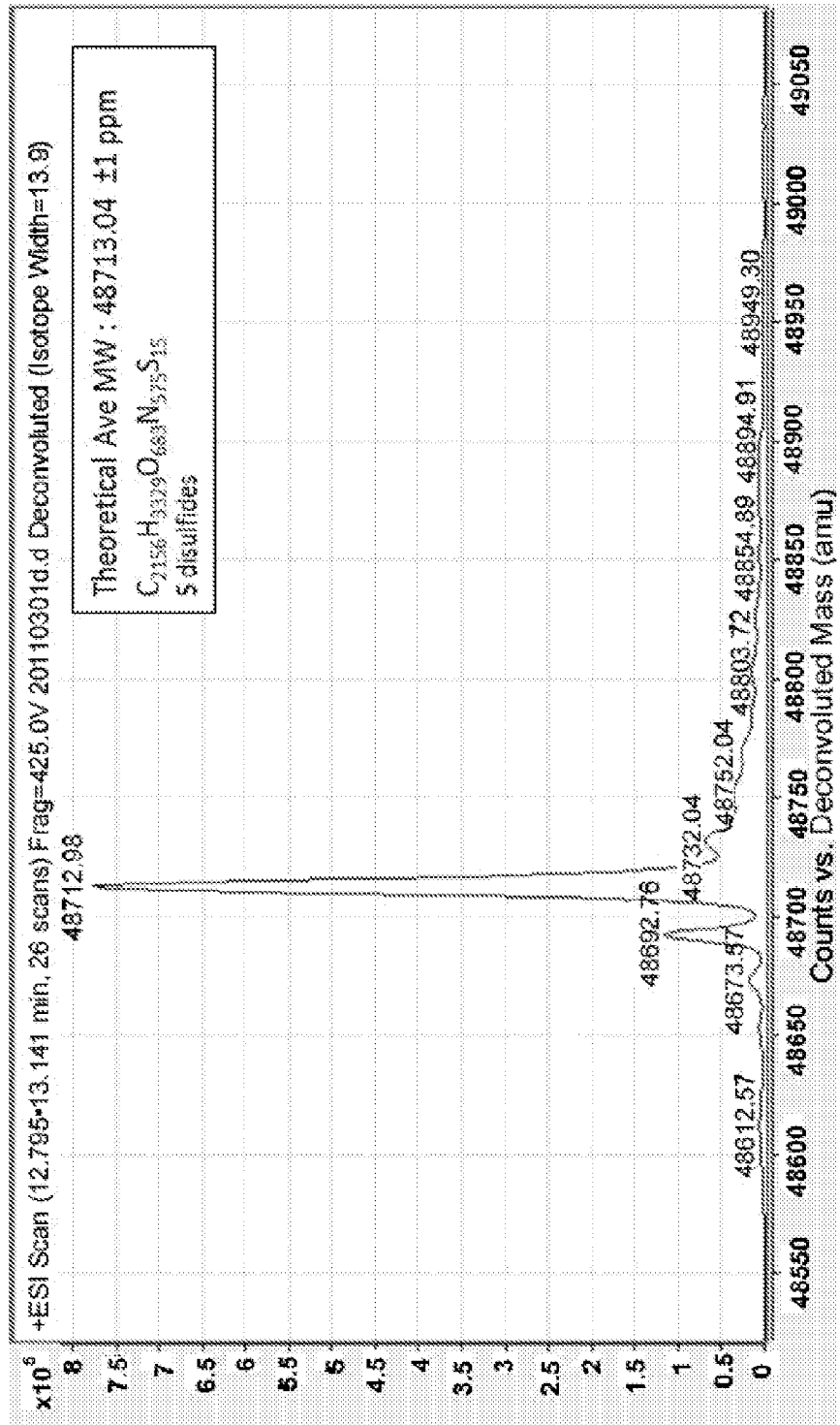
FIG. 3 depicts the mass spectrometry analysis of the molecular weight of TA106 Fab expressed in *E. coli*.
Figure 4:
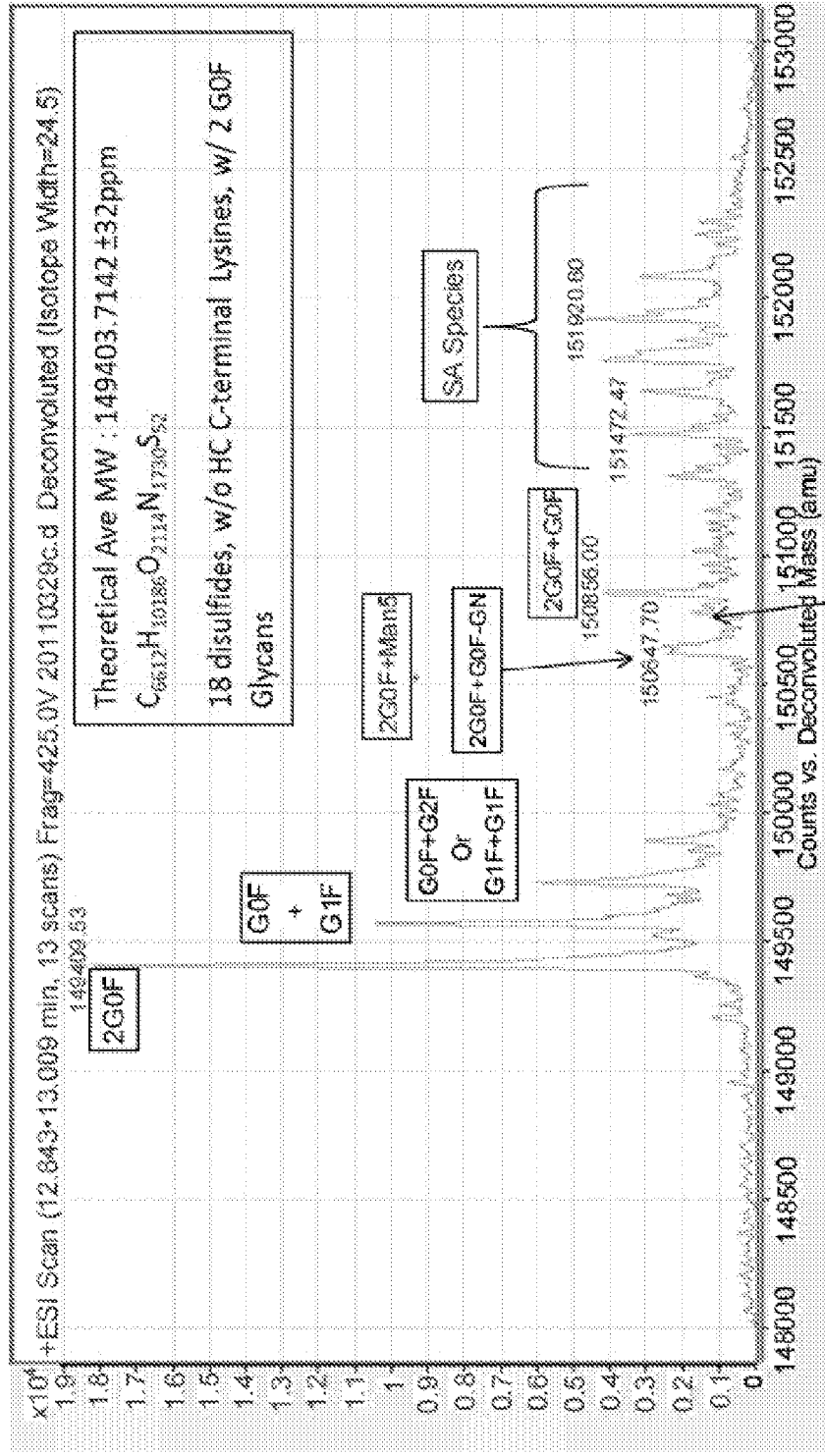
FIG. 4 depicts the mass spectrometry analysis of the molecular weight of the full-length TA106-derivative mAb (CLS011) expressed in CHO cells. Protein species modified with glycans of different types and/or lengths are identified.
Figure 5:
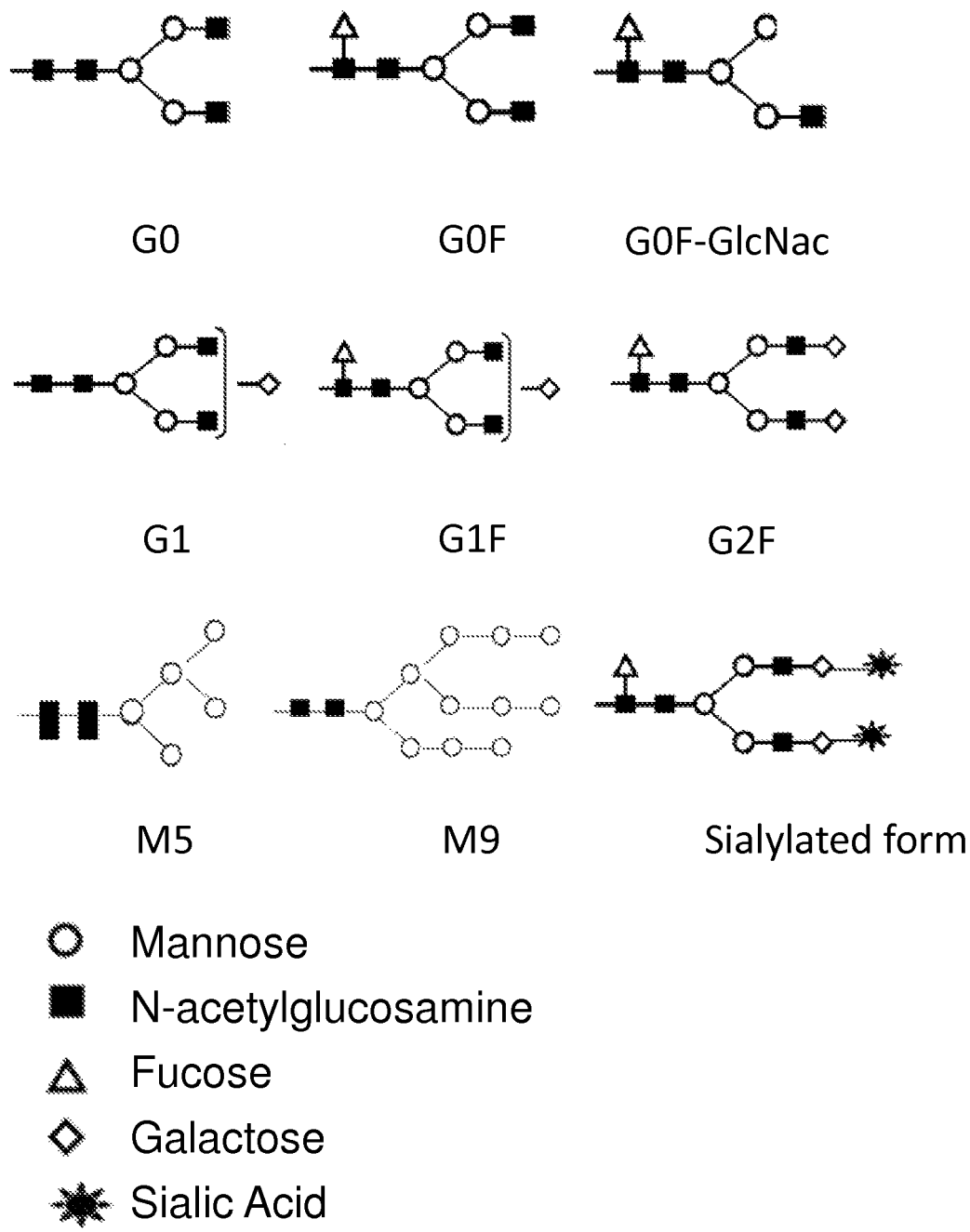
FIG. 5 depicts the structures of common glycans for protein glycosylation.

The volume was set so that about 10 μg or about 65 pmol of protein sample was loaded on the column. As shown in FIG. 3, the detected molecular weight of TA106 Fab fragment (48,712.98 Da) was consistent with its theoretical average molecular weight of 48,713.04 Da. The detected molecular weight of TA106-derivative mAb (CLS011, 149,408.53 Da) was consistent with its theoretical average molecular weight of 149,403.7142 Da and a profile of expressed mAb species modified with different patterns of glycans was identified (see FIG. 4). The patterns include varying amounts of terminal galactose (e.g., G2F, G1F and G0F), mannose-5 (e.g., ManS), N-acetylneuraminic acid (NANA), or sialic acid (SA) added to the mAb proteins. The structures of common glycans are illustrated in FIG. 5.

Figure 6:
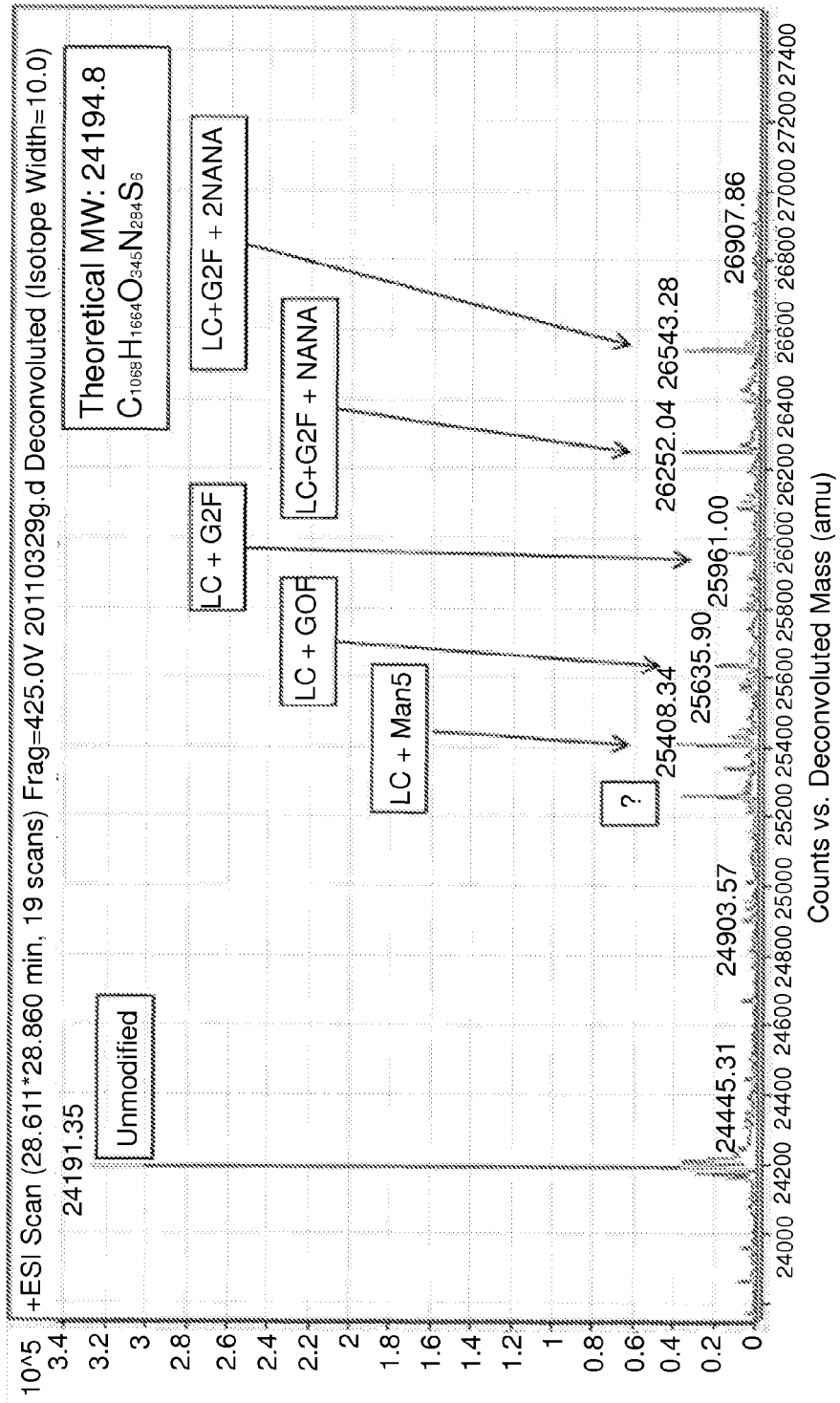
FIG. 6 depicts the mass spectrometry analysis of the molecular weight of the reduced light chain of TA106-derivative mAb (CLS011) expressed in CHO cells. Protein species modified with glycans of different types and/or lengths are identified.
Figure 7:
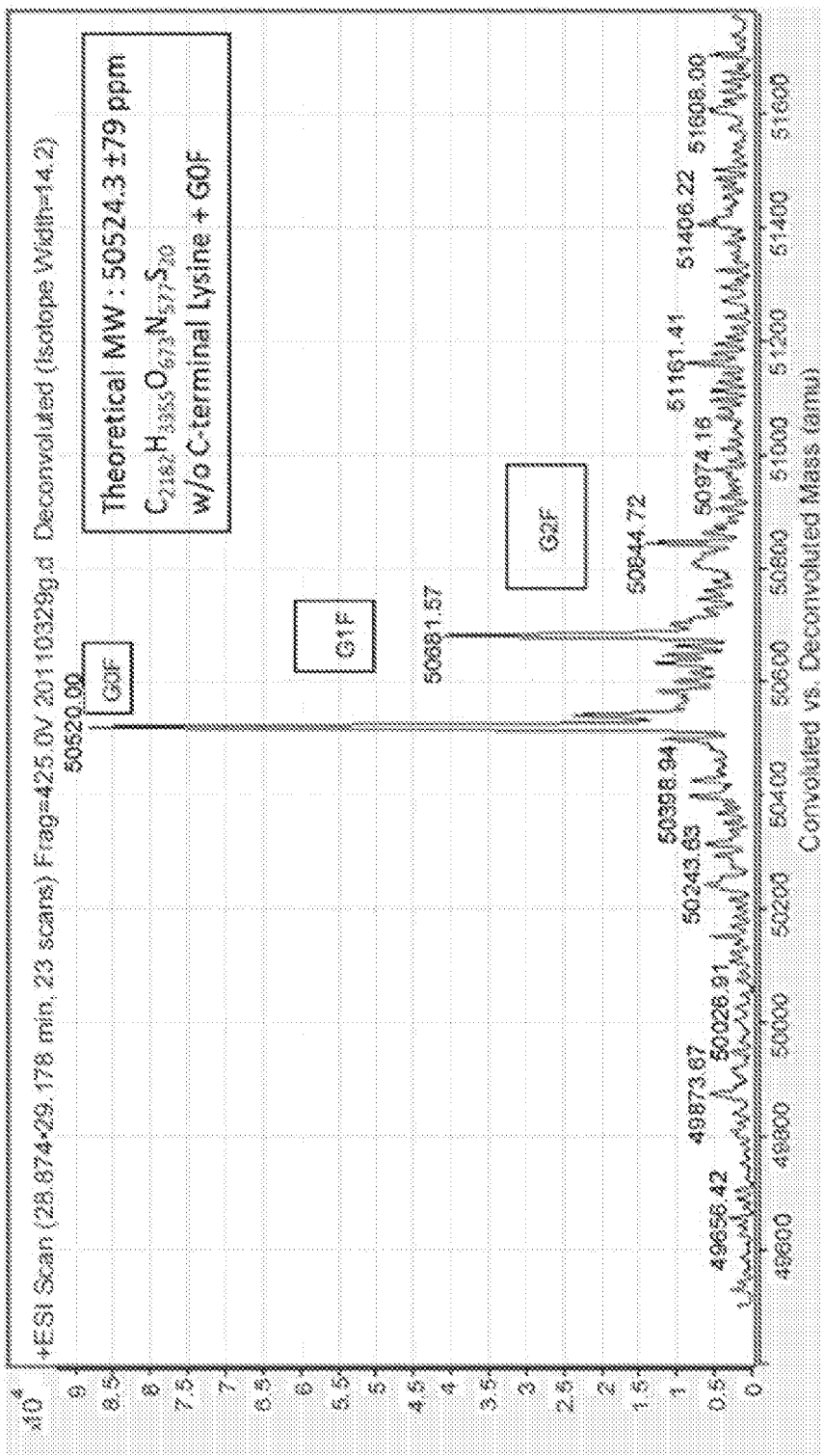
FIG. 7 depicts the mass spectrometry analysis of the molecular weight of the reduced heavy chain of TA106-derivative mAb (CLS011) expressed in CHO cells. Variant protein species modified with glycans of different types and/or lengths are identified.
Figure 8:
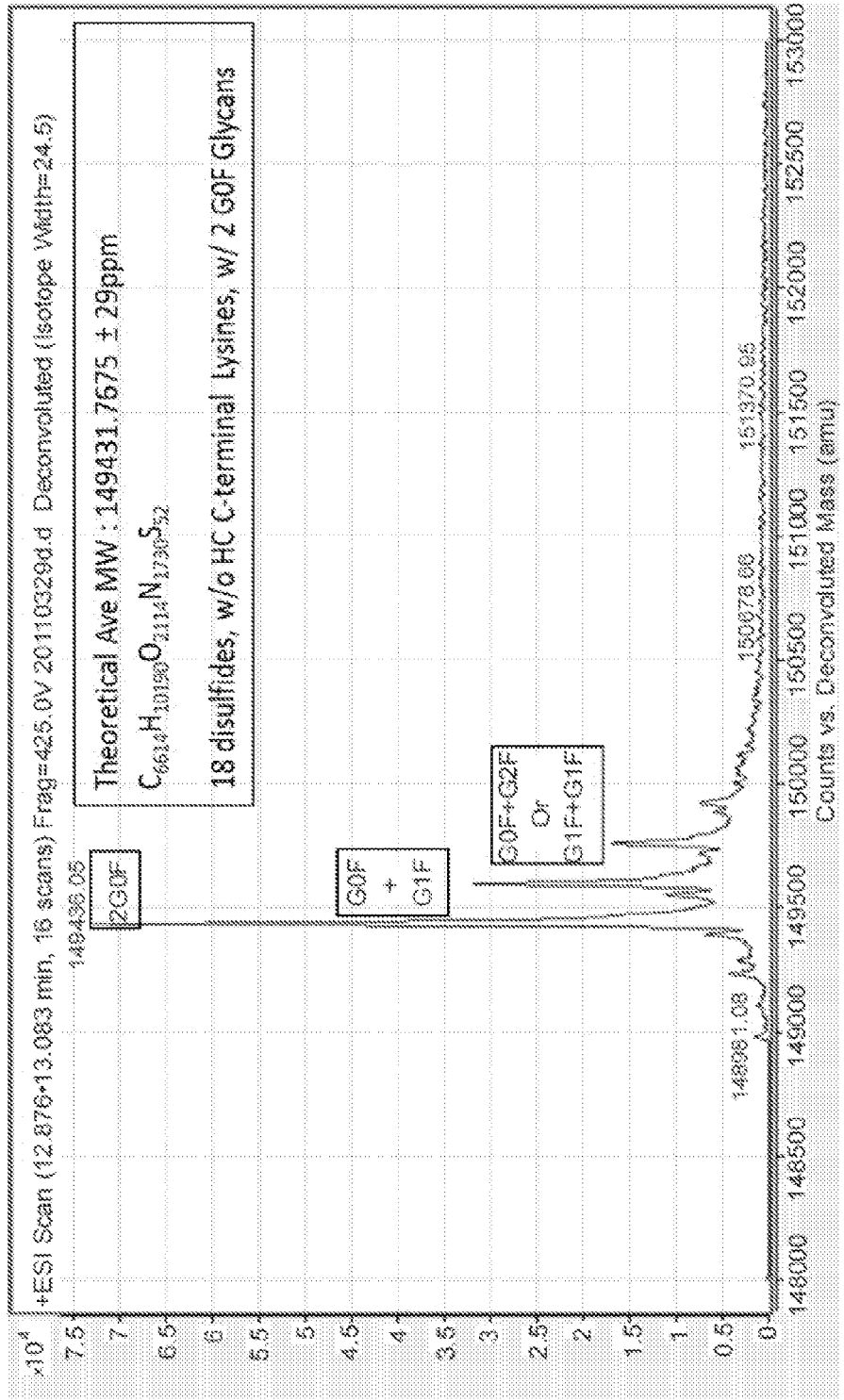
FIG. 8 depicts the mass spectrometry analysis of the molecular weight of the full-length TA106 variant N31Q (CLS012) expressed in CHO cells.
Figure 9:
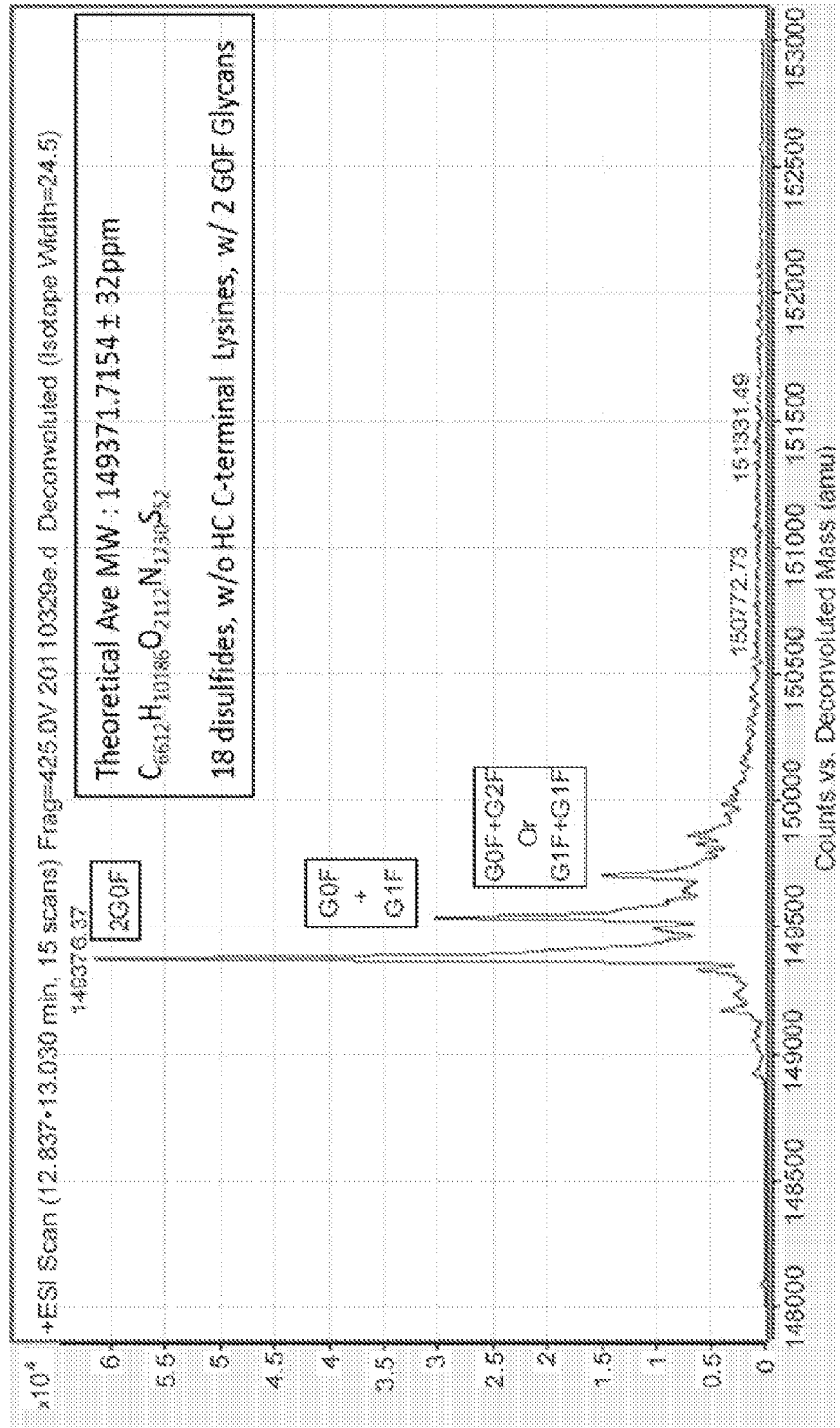
FIG. 9 depicts the mass spectrometry analysis of the molecular weight of the full-length TA106 variant S33A (CLS013) expressed in CHO cells.

The detected molecular weight of TA106 mAb light chain (24,191.35 Da) was consistent with its theoretical molecular weight of 24,194.8 Da and a profile of expressed light chain species modified with different lengths of glycans was identified (see FIG. 6). The detected molecular weight of TA106 mAb heavy chain (50,520.00 Da) was consistent with its theoretical molecular weight of 50,524.3 Da and variants of heavy chains modified with glycans were identified (FIG. 7). This glycosylation may be through the potential N-linked oligosaccharide site of $N^{296}S^{297}T^{298}$ (as in SEQ ID NO: 10) or other sites on the TA106-derivative mAb heavy chain. The detected molecular weight of TA106-derivative N31Q mAb (CLS012, 149,436.05 Da) was consistent with its theoretical average molecular weight of 149,431.7675 Da (FIG. 8) and its glycosylation was significantly reduced compared to wild type mAb CLS011 in FIG. 4. Specifically, purified CLS012 contains only protein species modified with one or two fucose moieties, which represents the glycosylation on the constant region of its heavy chain but not long glycan chains on the light chain previously seen in CLS011. Similarly, the detected molecular weight of TA106-derivative S33A mAb (CLS013, 149,376.37 Da) was consistent with its theoretical average molecular weight of 149,371.7154 Da (FIG. 9) and the mAb was significantly reduced in its glycosylation.

Therefore, the MassSpec analysis confirmed that: 1) TA106-originated mAbs (CLS011, 012, and 013) had expected N-linked glycosylation associated with their heavy chains; 2) CLS011 was further glycosylated on an N-linked motif in its light chain; and 3) CLS012 and CLS013 abolished light chain glycosylation.

Figure 10:
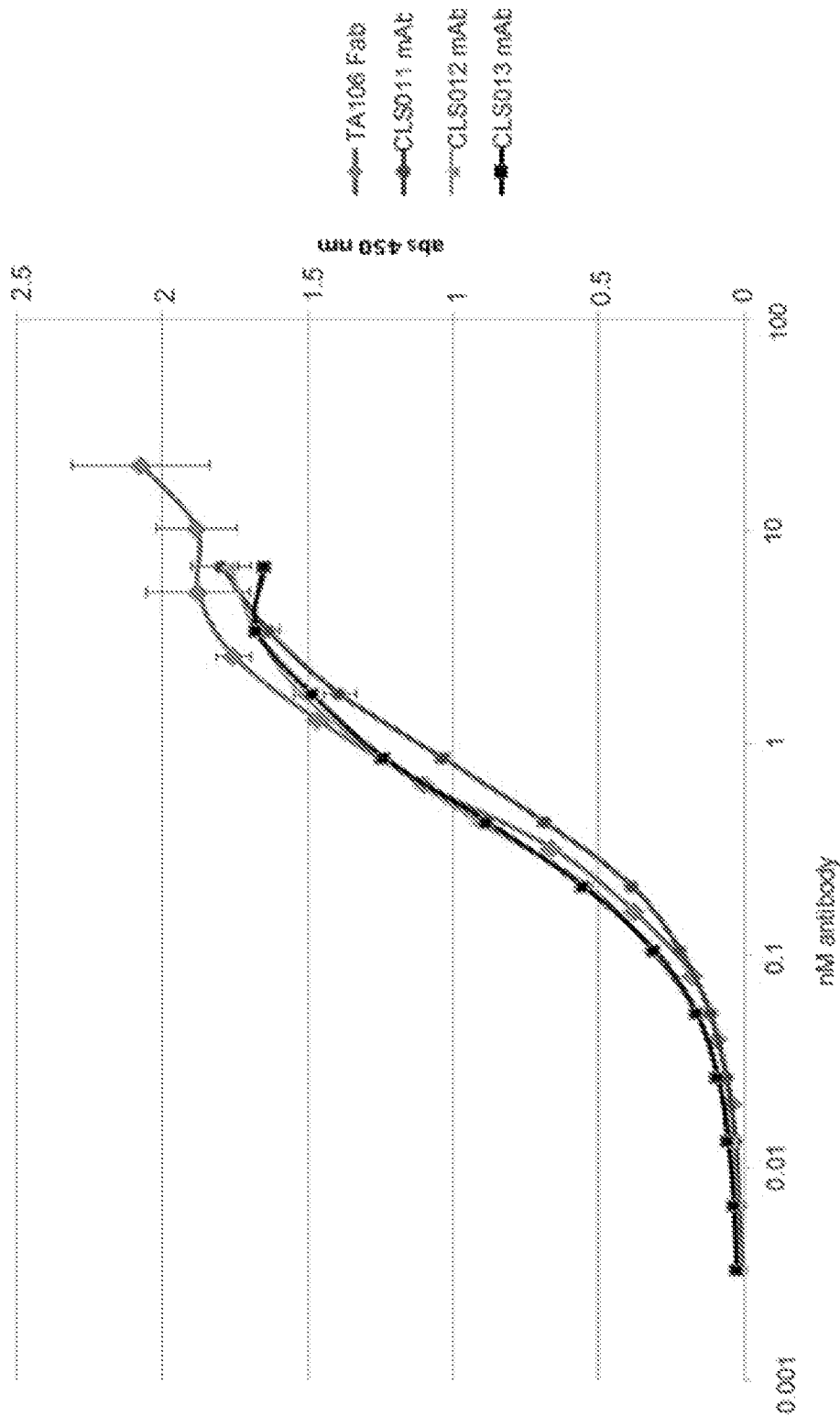
FIG. 10 depicts the ELISA analysis of the factor B binding activity of TA106 Fab (expressed in *E. coli*) and full-length TA106-derivative mAbs (expressed in CHO cells).

The binding activities of these mAbs towards factor B were analyzed by ELISA using standard protocols. In one exemplary experiment, MAXISORP™ ELISA plates (Nunc, #439454, Rochester, N.Y.) were coated with 50 μL of human factor B (Complement Technology, A135, 1 mg/mL, lot 14c) at a concentration of 0.5 μg/mL in carbonate coating buffer (0.795 g carbonate+1.46 g bicarbonate+1 mL 1% $NaN_3$ (final concentration of 0.002%) in 500 mL water, pH 9.6 (lot 2 Aug. 10)). Plates then were covered with plate sealers and incubated at 37±1° C. for one hour. Following coating, wells were emptied of reagent and washed in a BIOTEK® ELx405 plate washer (BIOTEK®, Winooski, Vt.) for three times with 200 μL wash solution (PBS/0.05% Tween 20) per well. Following washes, wells were blocked with 100 μL of BSA (1% w/v) and incubated for one hour at room temperature. Wells were then washed again as described above. Fifty microliter samples (i.e., TA106 Fab, CLS011 mAb, CLS012 mAb, and CLS013 mAb) were then added to wells and incubated for one hour at room temperature. In some instances, standards were prepared from TA106 stocks (20 mg/mL, Alexion Pharmaceuticals, Inc., Cheshire, Conn.). After sample incubation, the plate was washed as described above. Fifty microliters of secondary antibody (sheep-anti-human Kappa Light Chain HRP, 1 mg/mL, AP015, lot 274993B, The Binding Site, San Diego, Calif.) were added at a dilution (with PBS/0.02% Tween 20 as the diluent) of 1/10,000 of stock. The plate was then incubated for one hour at room temperature. Wells were further washed as described. Fifty microliters of Thermo Scientific (Pierce Biotechnology) 1-STEP® Ultra TMB (Cat.#34028, lot#1292304) were added to each well and incubated for color development at room temperature for approximately 40 minutes. The reaction was then stopped after adding 50 μL/well of 2N $H_2SO_4$. The plate was read on a BENCHMARK™ microplate reader (Bio-Rad Laboratories, Hercules, Calif.) at 450 nm. Standard curves were plotted with 4 parameter fit with DELTASOFT® 1.6 software, and sample concentrations were determined from the standard curves. As shown in FIG. 10, wild type (i.e., CLS011) and mutated (i.e., CLS012 and CLS013) mAbs have equivalent factor B-binding affinities (EC50=0.57 nM, as shown in FIG. 10) as that of TA106 Fab.

Binding kinetics of TA106-originated mAbs were analyzed using a FORTÉBIO® OCTET® biosensor (FORTÉBIO®, Inc.) in a similar protocol as described previously. In one exemplary experiment, wild type (CLS011) and the variant S33A (CLS013) mAbs were captured on anti-human Fc biosensors at a concentration of 5 μg/mL, diluted in 1× kinetics buffer (KB, a proprietary formulation containing PBS/Tween). Capture (loading) was carried out for 400 seconds, followed by briefly dipping the biosensors in 1× KB as a wash for 30 seconds. Associations with a titration series of purified human Factor B (Complement Technology, Tyler, Tex.), which concentrations range from 50 to 3 nM (diluted in 1× KB), were carried out for 300 seconds. For the dissociation process, the biosensors were immersed in 1× KB for 10 minutes to release Factor B. The detailed $K_D$, $K_{on}$ and $K_{dis}$ data are further listed in the following Table 1:

TABLE 1

Binding kinetics of anti-factor B mAbs, TA106-derivative mAb and TA106 variant S33A

| Sensor Info | Conc. (nM) | Response | $K_D$ (M) | $k_{on}$ (1/M s) | $k_{dis}$ (1/s) |
|---|---|---|---|---|---|
| CLS011 | 50 | 1.4047 | 2.49E−08 | 1.68E+05 | 4.18E−03 |
| CLS011 | 25 | 1.2371 | 1.73E−08 | 1.71E+05 | 2.97E−03 |
| CLS011 | 12.5 | 1.2637 | 1.11E−08 | 2.61E+05 | 2.89E−03 |
| CLS011 | 0 | 1.2395 | | | |
| CLS013 | 50 | 1.4393 | 3.21E−08 | 1.57E+05 | 5.04E−03 |
| CLS013 | 25 | 1.2873 | 5.22E−08 | 9.03E+04 | 4.72E−03 |
| CLS013 | 12.5 | 1.2849 | 3.77E−08 | 1.14E+05 | 4.28E−03 |
| CLS013 | 0 | 1.1898 | | | |

Figure 11:
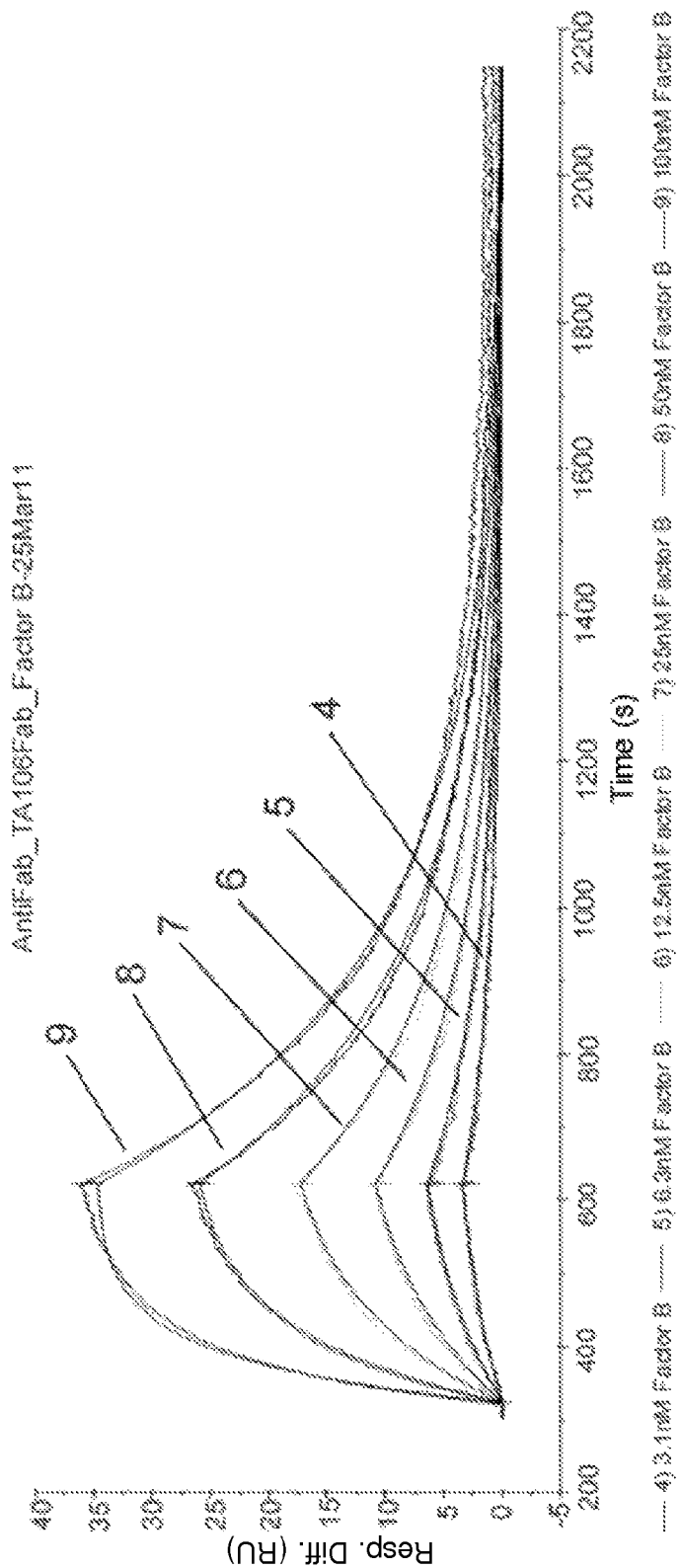
FIG. 11 shows the kinetics of captured TA106 Fab binding to soluble factor B using the Surface Plasmon Resonance (SPR) analysis. Four to nine represent different experimental data with factor B concentrations of 3.1, 6.3, 12.5, 25, 50, and 100 nM, respectively.
Figure 12:
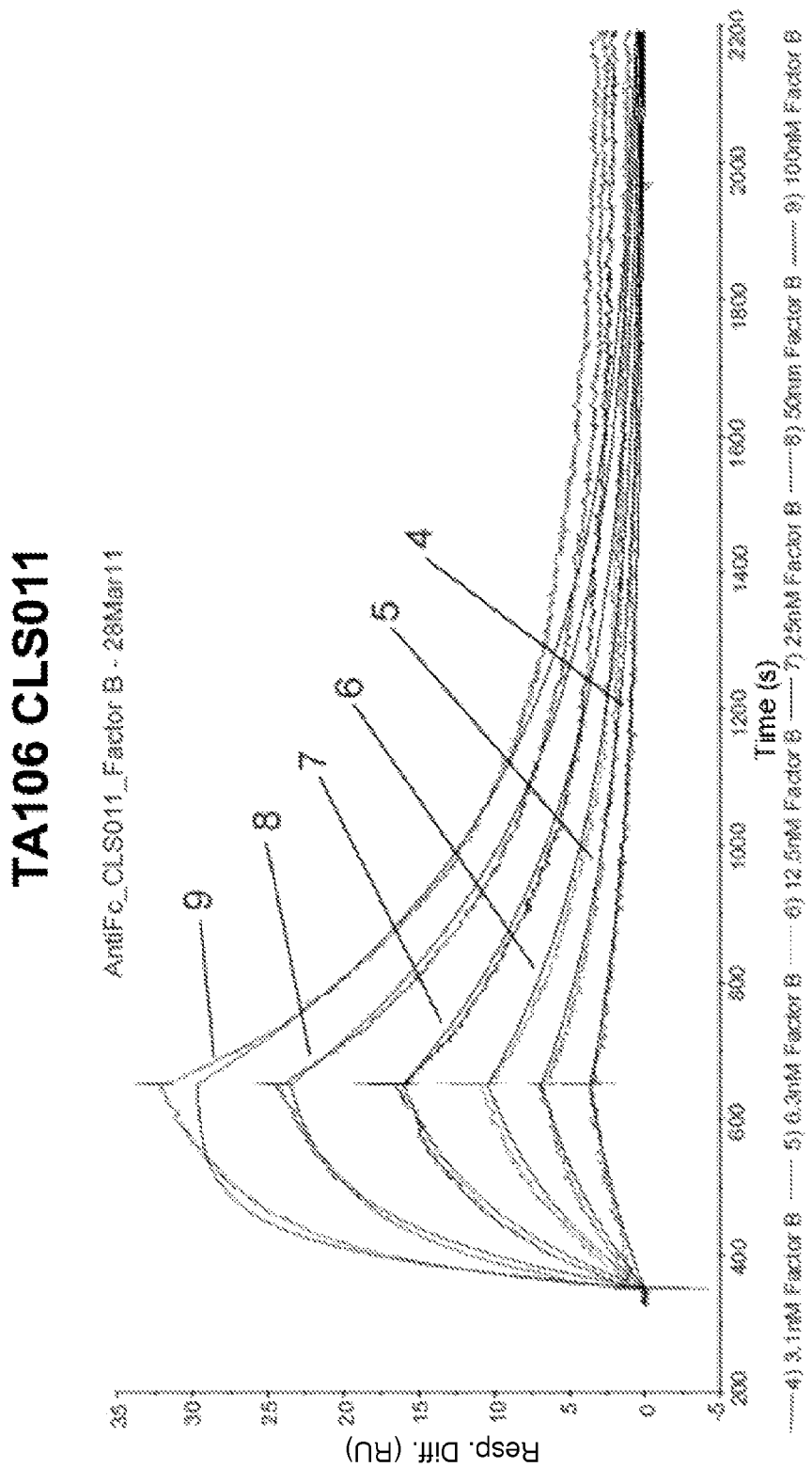
FIG. 12 shows the kinetics of captured TA106-derivative mAb (CLS011) binding to soluble factor B using the Surface Plasmon Resonance (SPR) analysis. Four to nine represent different experimental data with factor B concentrations of 3.1, 6.3, 12.5, 25, 50, and 100 nM, respectively.
Figure 13:
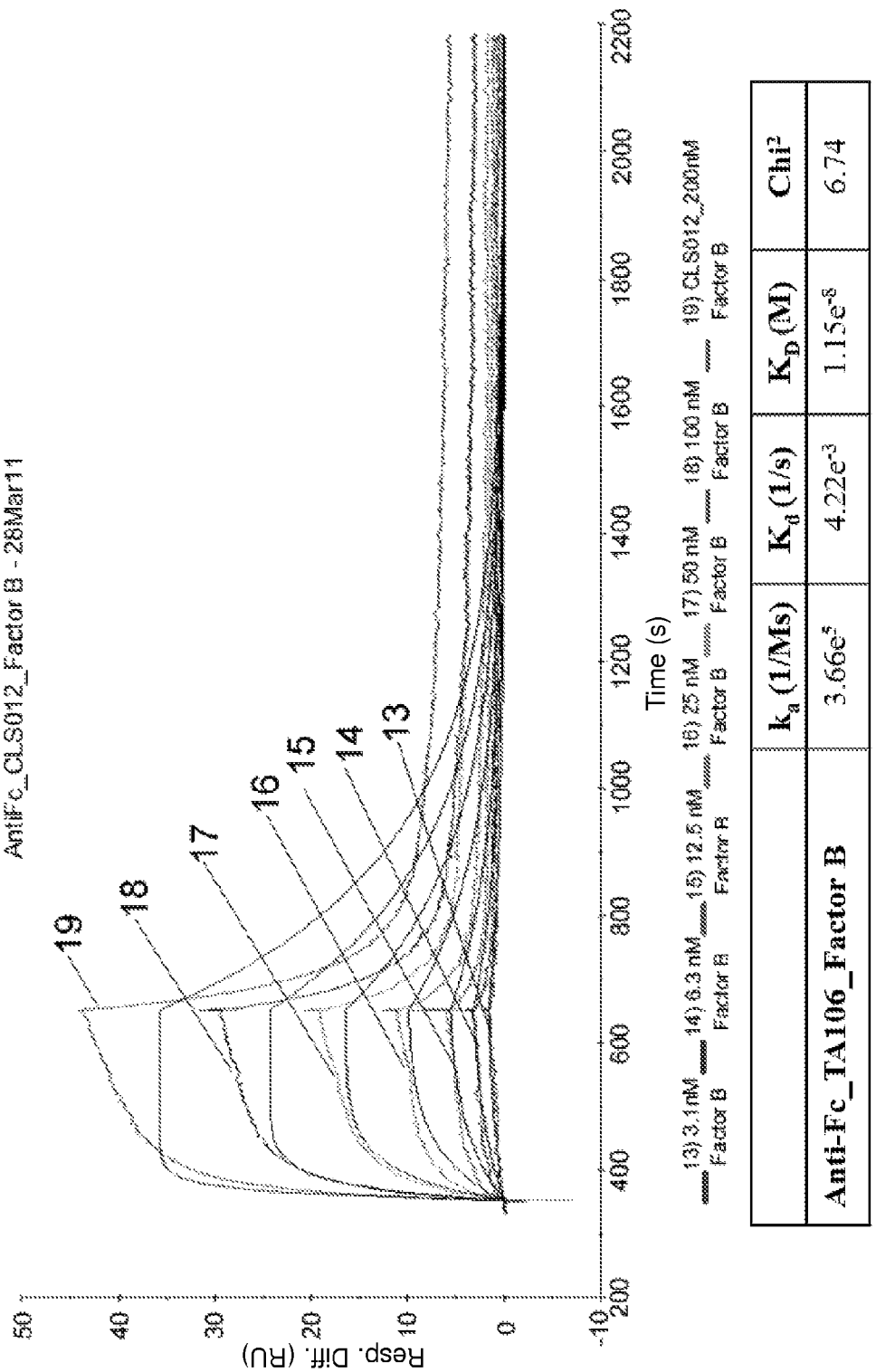
FIG. 13 shows the kinetics of captured TA106-derivative mAb variant N31Q (CLS012) binding to soluble factor B using the Surface Plasmon Resonance (SPR) analysis. Thirteen to nineteen represent different experimental data with factor B concentrations of 3.1, 6.3, 12.5, 25, 50, 100, and 200 nM, respectively.
Figure 14:
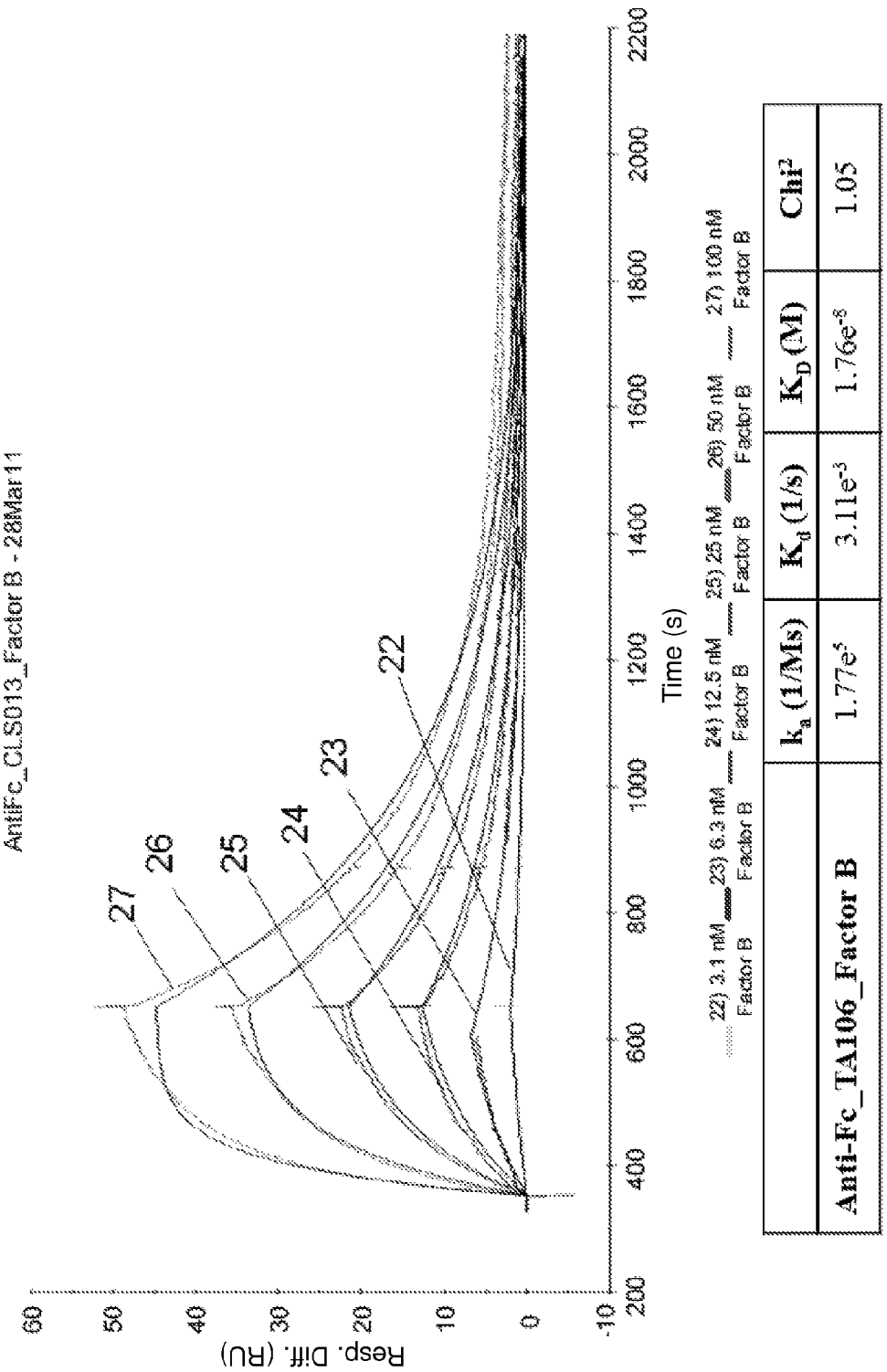
FIG. 14 shows the kinetics of captured TA106-derivative mAb variant S33A (CLS013) binding to soluble factor B using the Surface Plasmon Resonance (SPR) analysis. Twenty-two to twenty-seven represent different experimental data with factor B concentrations of 3.1, 6.3, 12.5, 25, 50, and 100 nM, respectively.
Figure 15:
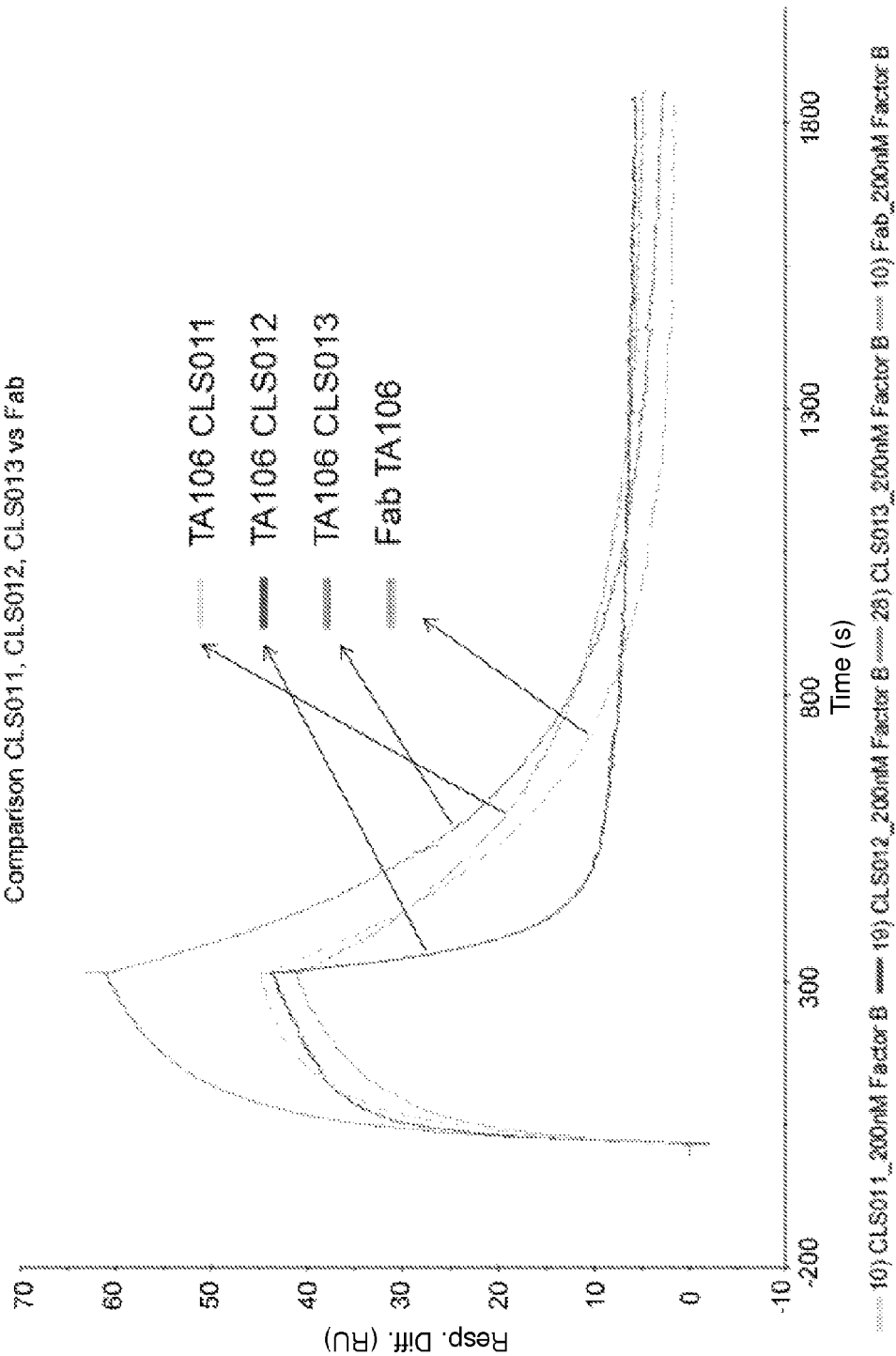
FIG. 15 shows the comparison of kinetics of captured TA106 Fab and variant mAbs binding to 200 nM soluble factor B using the Surface Plasmon Resonance (SPR) analysis.

Binding kinetics of mAbs were further characterized using BIACORE™ Surface Plasmon Resonance (SPR) technology (GE Healthcare, Piscataway, N.J.). For a detailed description of SPR and its applications in affinity measurement, please see Karlsson and Larsson, Antibody Engineering: Methods and Protocols, Methods in Molecular Biology (2003), 248: 389-415. In one exemplary experiment, TA106 Fab and derivative mAbs were captured on chips of a BIACORE™ 3000 analyzer and samples of human factor B of different concentrations were flowed as the antigen over the surface to model soluble human factor B binding, using protocols recommended by the manufacturer (e.g., in the product brochure #BR-9003-31). All these referenced publications are hereby incorporated by reference in their entirety. For the TA-106 Fab experiment, human Fab binder was amine coupled to two flow cells of a CM5 chip. Fab TA106 (Xoma, Lot# TTA1007, 20 mg/mL) was then flowed over one flow cell, followed by injections of human factor B on both flow cells. Concentrations (factor B) between 3.1-200 nM were run. The surface was regenerated between each cycle. As depicted in FIG. 11, $K_D$ of TA106 Fab was determined to be approximately 24.9 nM. The affinities of mAbs, i.e., CLS011, CLS012, and CLS013, were determined using a similar capture approach. In one exemplary experiment, human anti-Fc antibody was amine coupled to two flow cells of a CM5 chip. Each of the TA106-originated mAbs was then flowed over one flow cell, followed by injecting human factor B (3.1-200 nM) on both flow cells. As depicted in FIGS. 12-14, the affinities of CLS011, CLS012, and CLS013 were approximately 15.4 nM, 11.5 nM, and 17.6 nM, respectively. The binding kinetics of TA106 Fab and mAbs (CLS011, CLS012, and CLS013) to 200 nM soluble factor B were compared in FIG. 15. The affinities of CLS011 and CLS013 were determined to be approximately 15-20 nM with reasonable fits. Due to poor fits the affinity of CLS012 was not reliable. A sensorgram plot of TA106 Fab, CLS011, CLS012 and CLS013 showed that the dissociation rate of CLS012 was faster than other Fab or mAbs (data not shown). Due to this quick release of CLS012 from factor B, Applicants' later development work was focused on TA106-derivative S33A mAb and Fab (CLS013 and CLS016).

Figure 16:
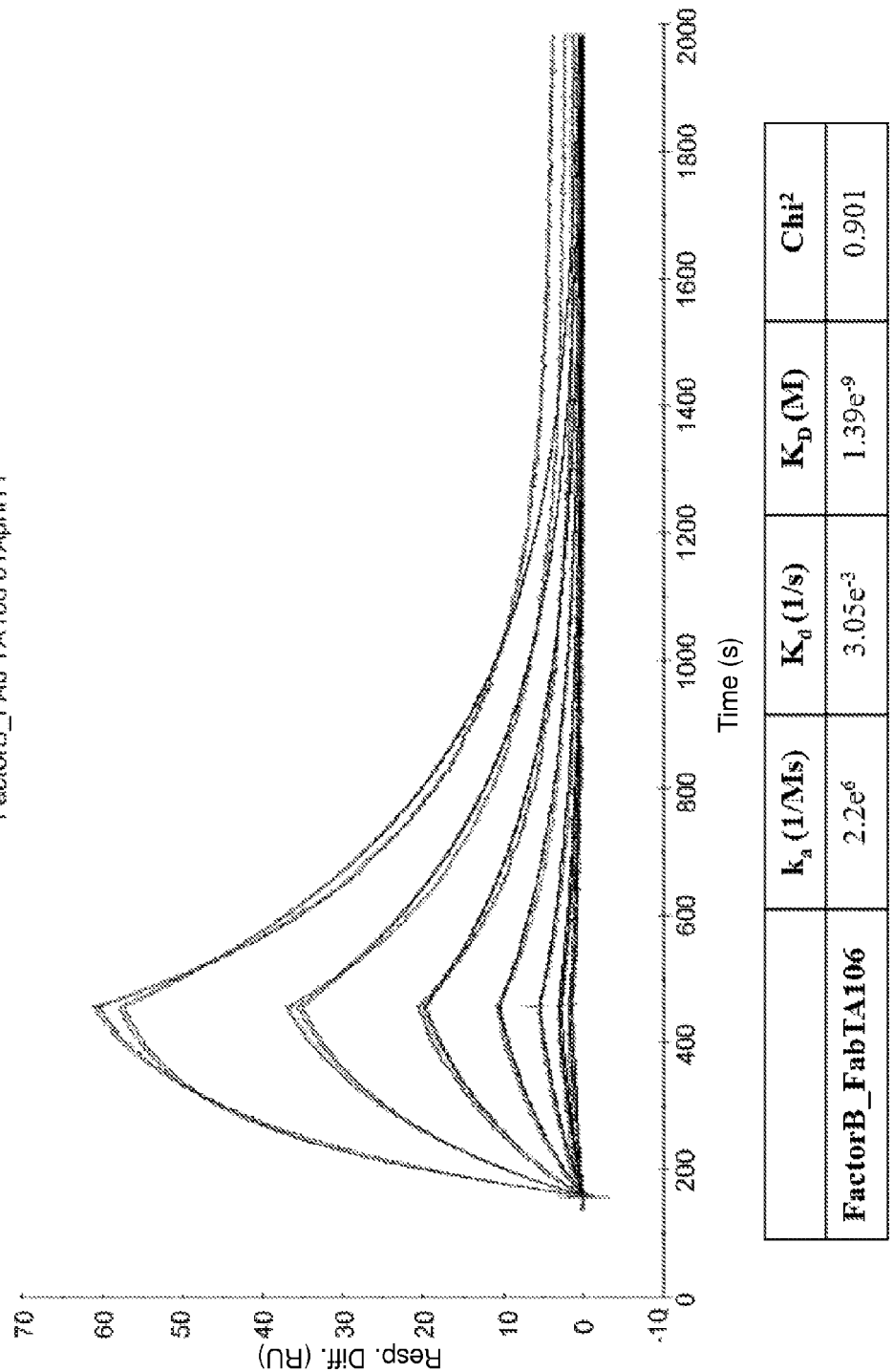
FIG. 16 shows the kinetics of free TA106 Fab binding to captured factor B using the Surface Plasmon Resonance (SPR) analysis.

Further, to resolve the discrepancy in TA106 Fab's affinity to factor B in this experiment (24.9 nM) and in the previous ELISA result (EC50=0.57 nM), an additional SPR experiment was carried out, in which factor B was directly bound to the BIACORE™ chip with low coverage and TA106 Fab was flowed over the surface. As depicted in FIG. 16, the affinity for this configuration ($K_D$=1.4 nM) was consistent with the ELISA result. The difference in the two BIACORE™ data sets could be explained as either that the conformation of factor B changes when binding to the surface or that not all commercial factor B is active. This later BIACORE™ experiment (with a fixed concentration of factor B bound to the chip) removed the factor B concentration from the calculation.

A summary of characterizations of TA106-originated Fab and mAbs is listed in the following Table 2:

TABLE 2

Summary of characterization of TA106 Fab and variant mAbs

| Name | Modification | Heavy chain MW | Light chain MW | Binding to fB by ELISA | SPR $K_D$ | Theoretical mAb MW |
|---|---|---|---|---|---|---|
| Fab TA106 | None (*E. coli*) | — | — | Yes | 25 nM | 48,713 +/− 1 |
| CLS011 mAb | None | 59 kDa | 26 kDa | Yes | 15 nM | 149,403 +/− 32 |
| CLS012 mAb | N to Q | 60 kDa | 26 kDa | Yes | Not calculated (poor fits) | 149,431 +/− 29 |
| CLS013 mAb | S to A | 60 kDa | 27 kDa | Yes | 18 nM | 149,371 +/− 32 |

Figure 17:
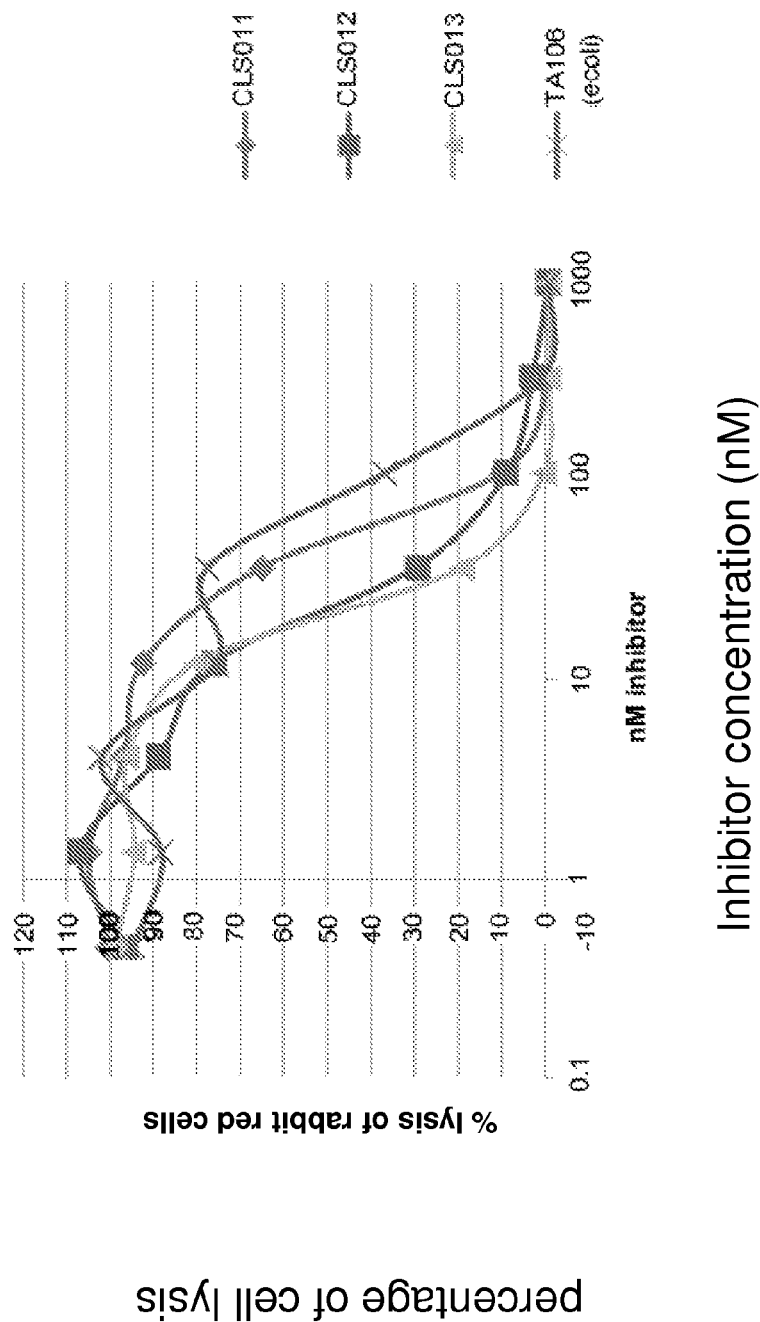
FIG. 17 shows antagonism of hemolysis of rabbit red blood cells in 10% normal human serum of TA106 Fab and variant mAbs.

The TA106-originated mAbs were further tested for their inhibitory activities in a rabbit red blood cell hemolysis assay, using 10% normal human serum. The method of this hemolysis assay is well-known to a person of skill in the art. In one exemplary experiment, 10% (final concentration) normal human serum was incubated with different concentrations of mAbs (2-fold titrations). Four hundred microliters of rabbit red blood cells (Lampire Biological Laboratories, Pipersville, Pa.) were washed with GVB buffer (Gelatin Veronal-Buffered Saline, containing 2 mM $MgCl_2$, 1.6 mM EGTA to promote the complement alternative pathway and inhibit the complement classical pathway) 4 times and then resuspended in GVB buffer. About $5 \times 10^6$ cells were then added to each plate well and incubated at 37° C. for 10 minutes. The plate was then centrifuged at 3,000 rpm for 1 minute. Eighty-five microliters of the supernatant were transferred out for optical density determination by a microplate reader with standard methods at a wavelength of 415 nm. As depicted in FIG. 17, CLS011 (wild type mAb), CLS012 (N31Q), and CLS013 (S33A) had anti-hemolytic activities equivalent to that of TA106 Fab.

Figure 18:
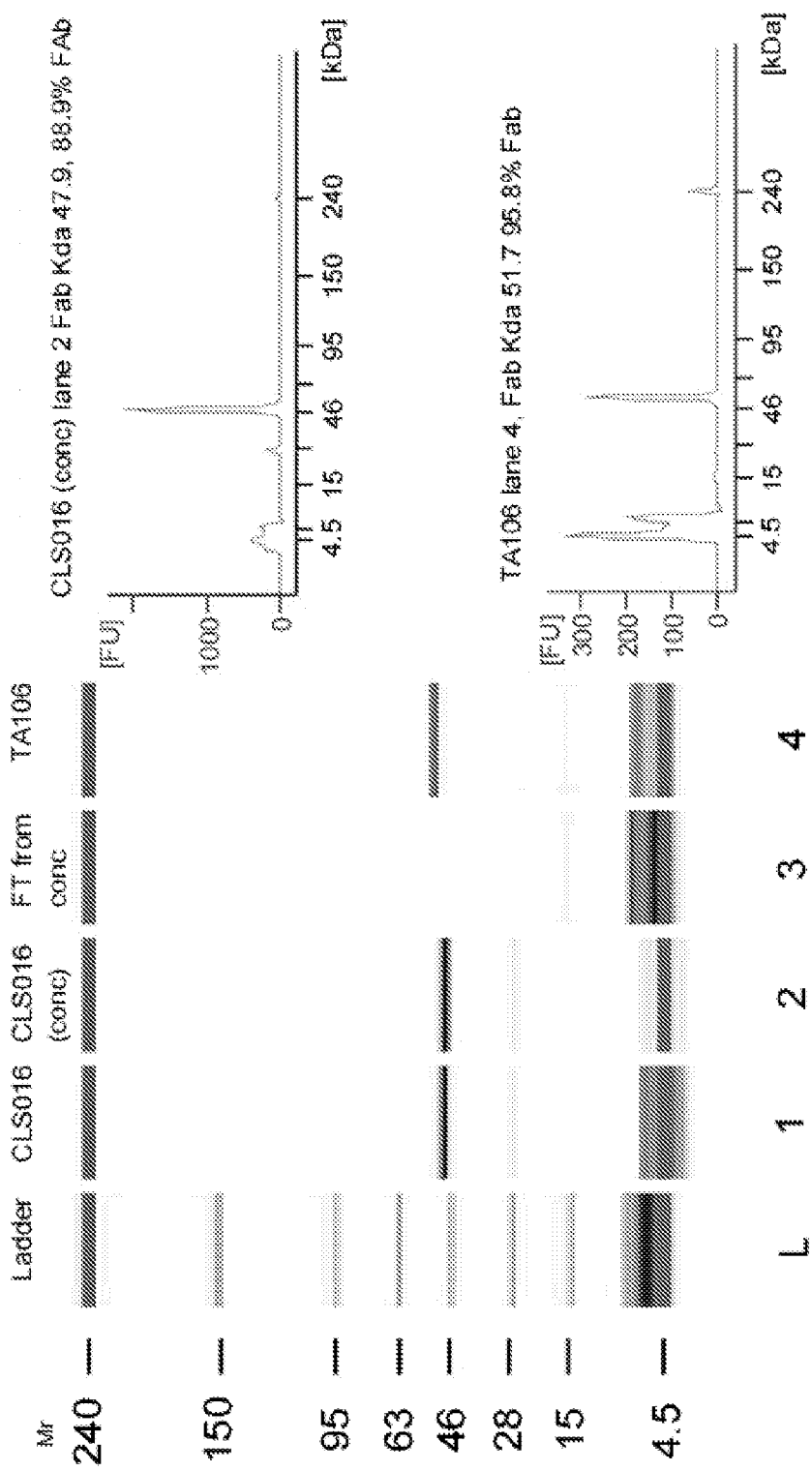
FIG. 18 depicts a non-reducing-PAGE-like image (left panel) showing the molecular weights of TA106 Fab (expressed in *E. coli*) and TA106-derivative S33A Fab (expressed in CHO). Lane L contains molecular weight standards ("markers"). Lanes 1-3 represent TA106 S33A Fab (before concentration), TA106 S33A Fab (after concentration), and the flow-through fraction from the concentration process, respectively. Lane 4 contains TA106 Fab expressed in *E. coli*. The image was acquired after capillary electrophoresis using an AGILENT™ protein chip 230 with an AGILENT™ bioanalyzer 2100. The right panel of FIG. 18 depicts chromatographic traces of the same capillary electrophoresis result as in the left panel. The Y-axis represents the fluorescence units. The X-axis represents protein molecular weight in kDa.

The $IgG_1$ Fab fragment (CLS016) of the S33A variant was further prepared and compared with TA106 Fab. The construct transfection, expression and purification of TA106 Fab from *E. coli* were performed by Xoma (Berkeley, Calif.) using standard methods known in the art. The construction, transfection, expression and purification of TA106 variant S33A (CLS016) from CHO cells were performed by standard methods known in the art and as described previously in this disclosure. The expressed Fabs were analyzed with an AGILENT™ bioanalyzer 2100 (AGILENT™ Technologies), according to the manufacturer's recommended protocols and as described above. In one exemplary experiment, Fabs were loaded and analyzed in non-reducing conditions. As shown in FIG. 18, TA106 Fab has an apparent molecular weight of about 51.7 kDa, while TA106-derivative S33A Fab (CLS016) has an apparent molecular weight of about 47.9 kDa.

Figure 19:
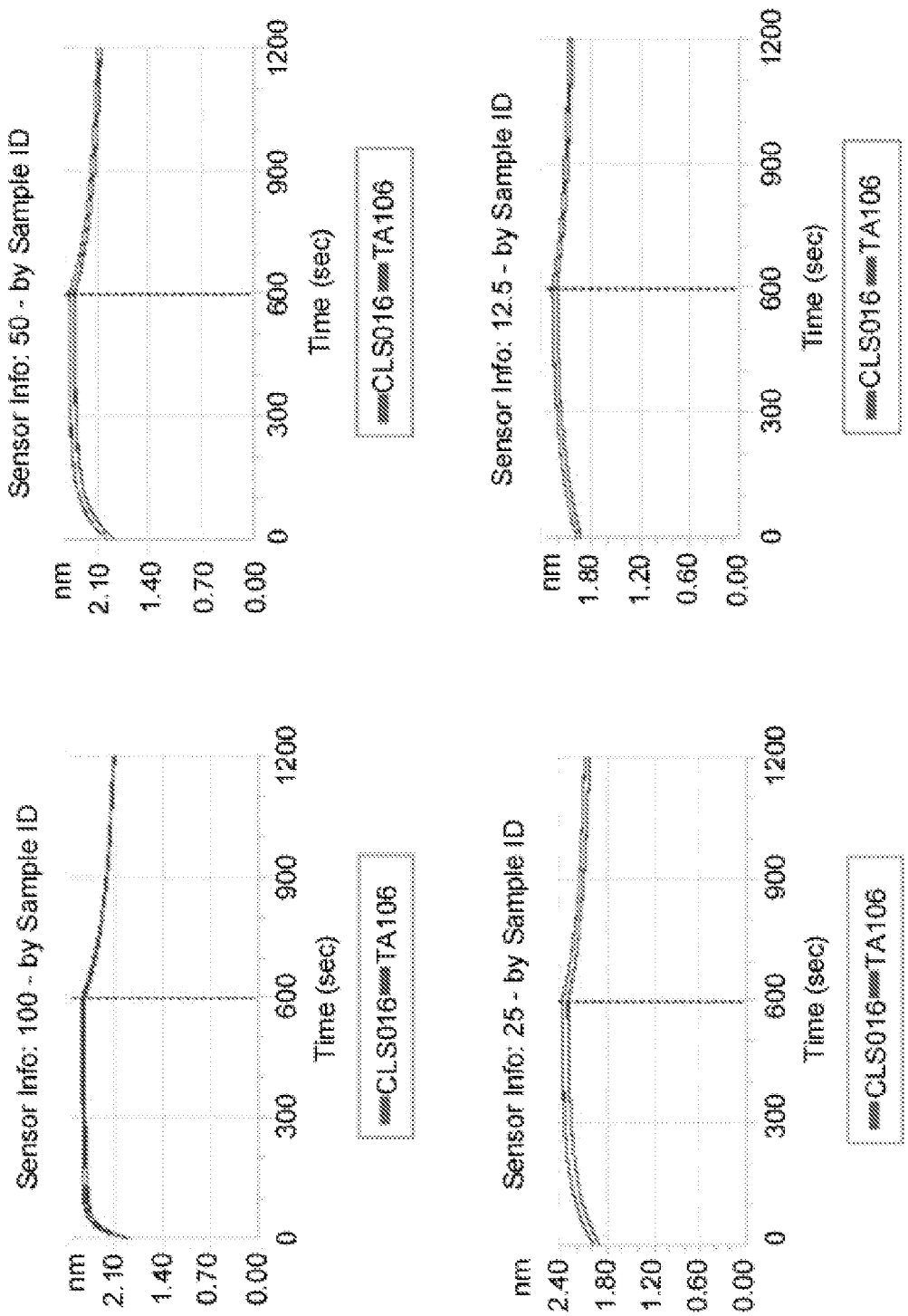
FIG. 19 depicts the kinetics of TA106 Fab and TA106-derivative S33A Fab (expressed in CHO) binding to factor B analyzed with the FORTÉBIO® OCTET® system by bio-layer interferometry. Different concentrations (12.5 nM, 25 nM, 50 nM, or 100 nM) of Fabs were used.
Figure 20:
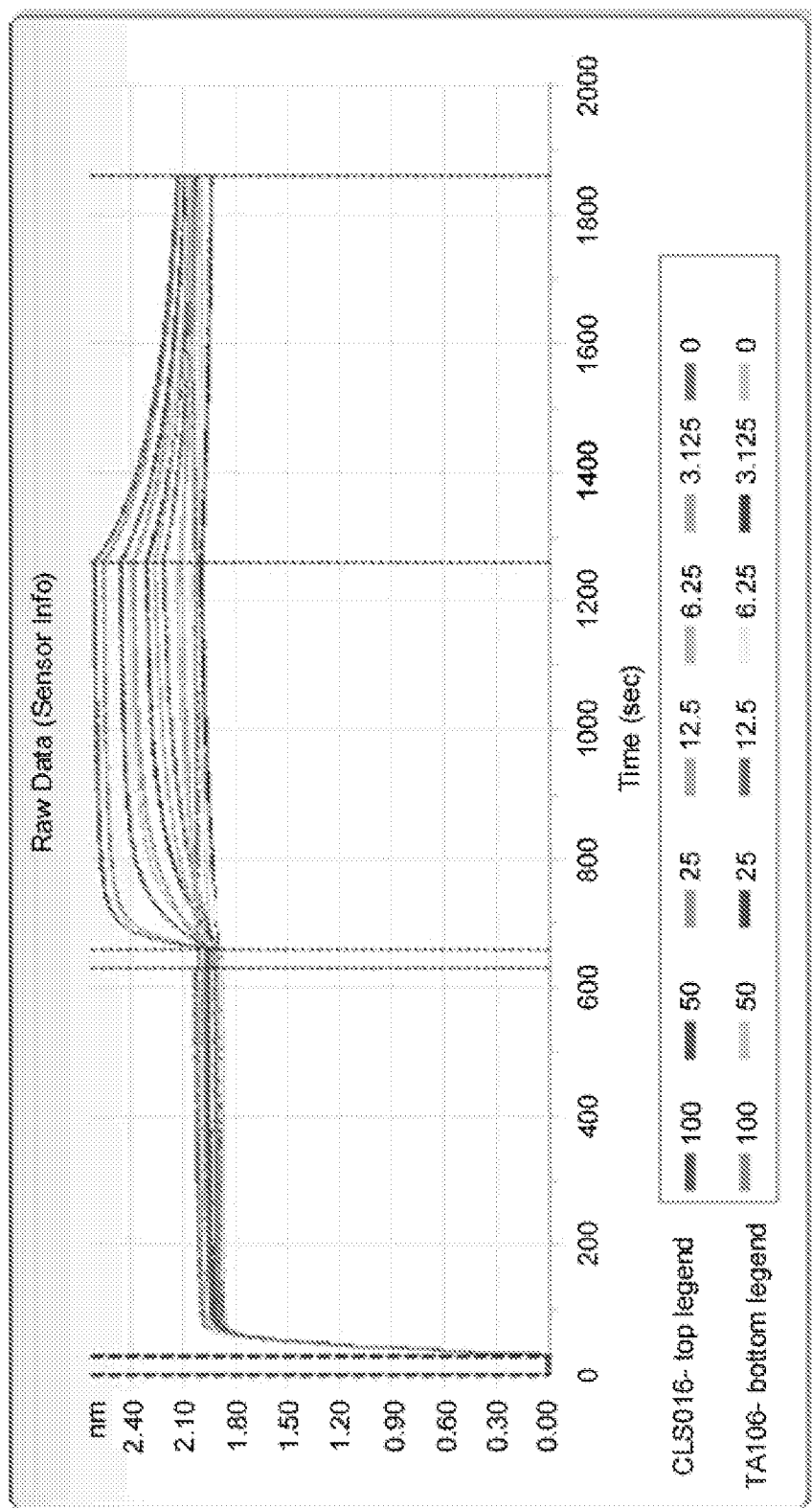
FIG. 20 depicts the kinetics of TA106 Fab and TA106-derivative S33A Fab (expressed in CHO) binding to factor B analyzed with the FORTÉBIO® OCTET® system by bio-layer interferometry. Different concentrations (0, 3.125 nM, 6.25 nM, 12.5 nM, 25 nM, 50 nM, or 100 nM) of Fabs were used.

Binding kinetics of TA106 and TA106 S33A Fab (CLS016) to Factor B were analyzed using a FORTÉBIO® OCTET® biosensor (FortéBio, Inc.) in a similar protocol as described previously. In one exemplary experiment, Factor B (Complement Technology) was biotinylated at a 1:10 ratio and coupled to a streptavidin biosensor at a concentration of 5 μg/mL for a loading time of 600 seconds. Biosensors were briefly dipped in 1× KB as a wash for 30 seconds. Associations with a titration series of Fab with a concentration range from 100 to 3 nM (diluted in 1× KB) were carried out for 600 seconds. Fabs were dissociated from the biosensor by immersing the biosensor in 1× KB during the 600 second dissociation phase. As depicted in FIGS. 19 and 20, both TA106 Fab and TA106-derivative S33A Fab (CLS016) bound to Factor B at various concentrations, resulting in nearly identical association and dissociation profiles. Kinetic assessments using partial local fit parameters yielded identical values for $K_D/k_a/K_d$ at each concentration tested. The detailed $K_D$, $K_{on}$ and $K_{dis}$ data are further listed in the following Table 3.

Figure 21:
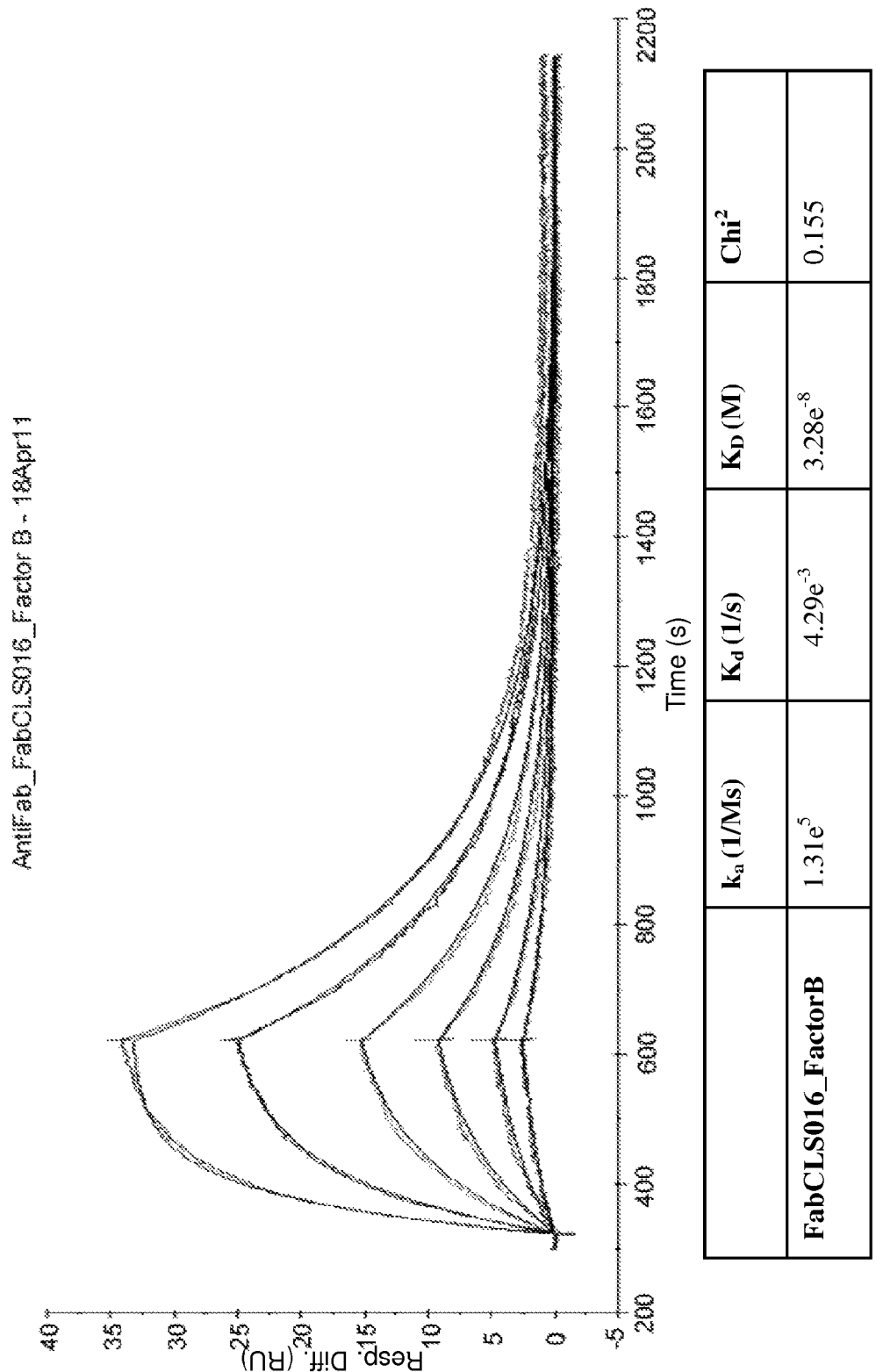
FIG. 21 shows the kinetics of captured TA106-derivative S33A Fab (CLS016) binding to soluble factor B using the Surface Plasmon Resonance (SPR) analysis.
Figure 22:
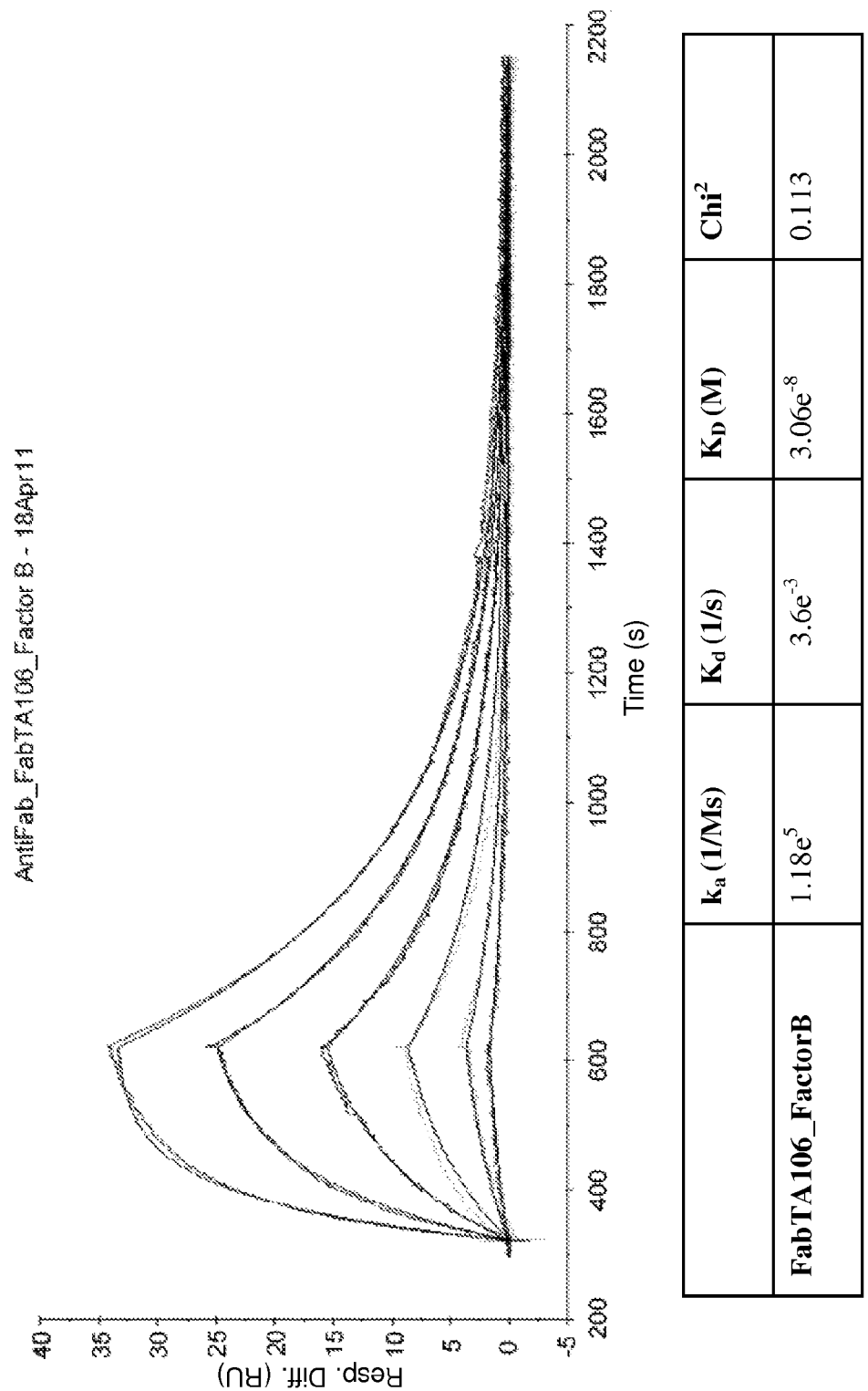
FIG. 22 shows the kinetics of captured TA106 wild type Fab binding to soluble factor B using the Surface Plasmon Resonance (SPR) analysis.
Figure 23:
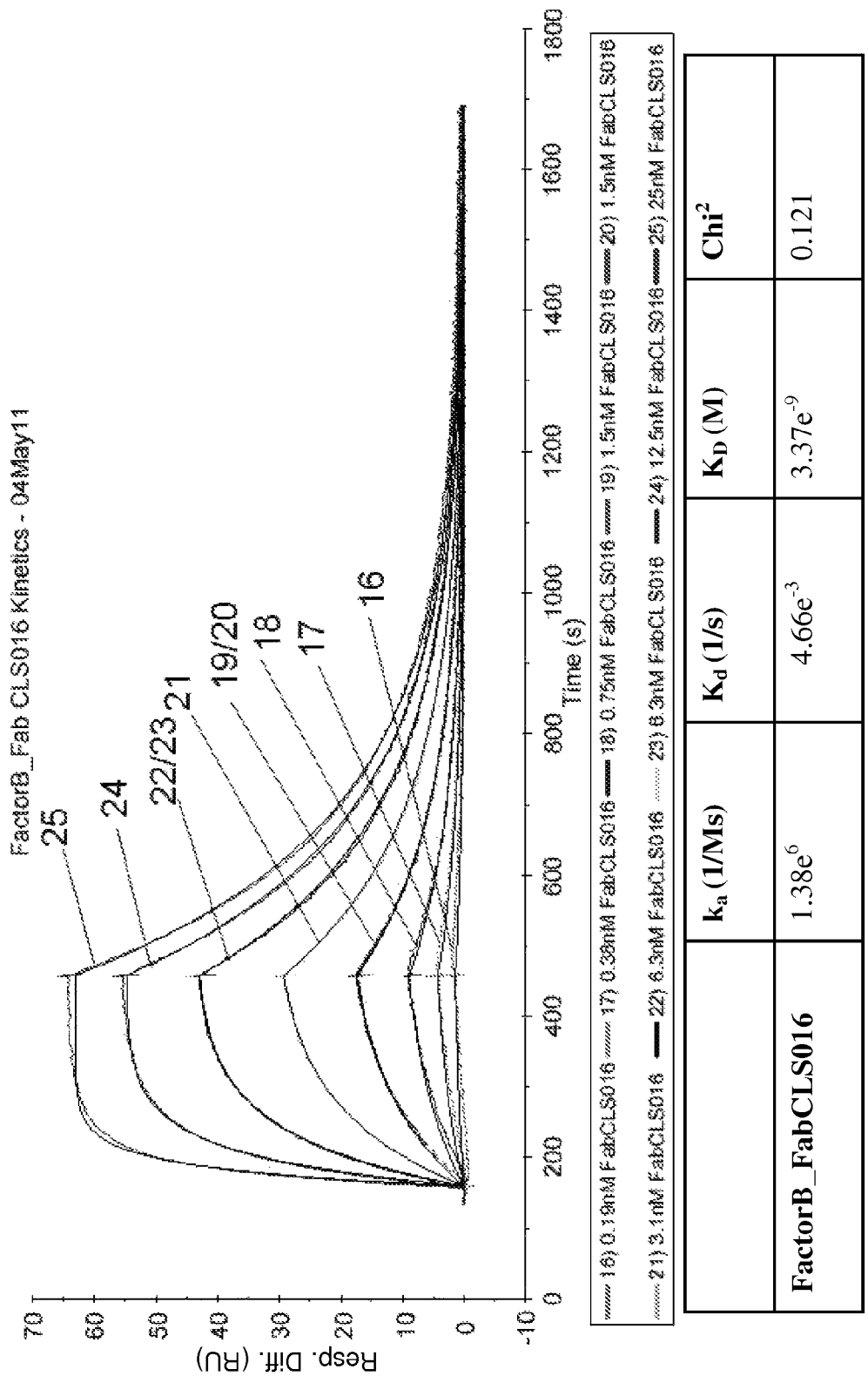
FIG. 23 shows the kinetics of free TA106-derivative S33A Fab (CLS016) binding to captured factor B using the Surface Plasmon Resonance (SPR) analysis. Sixteen to twenty-five represent different experimental data with CLS106 concentrations of 0.19, 0.38, 0.75, 1.5, 3.1, 6.3, 12.5, and 25 nM, respectively.
Figure 24:
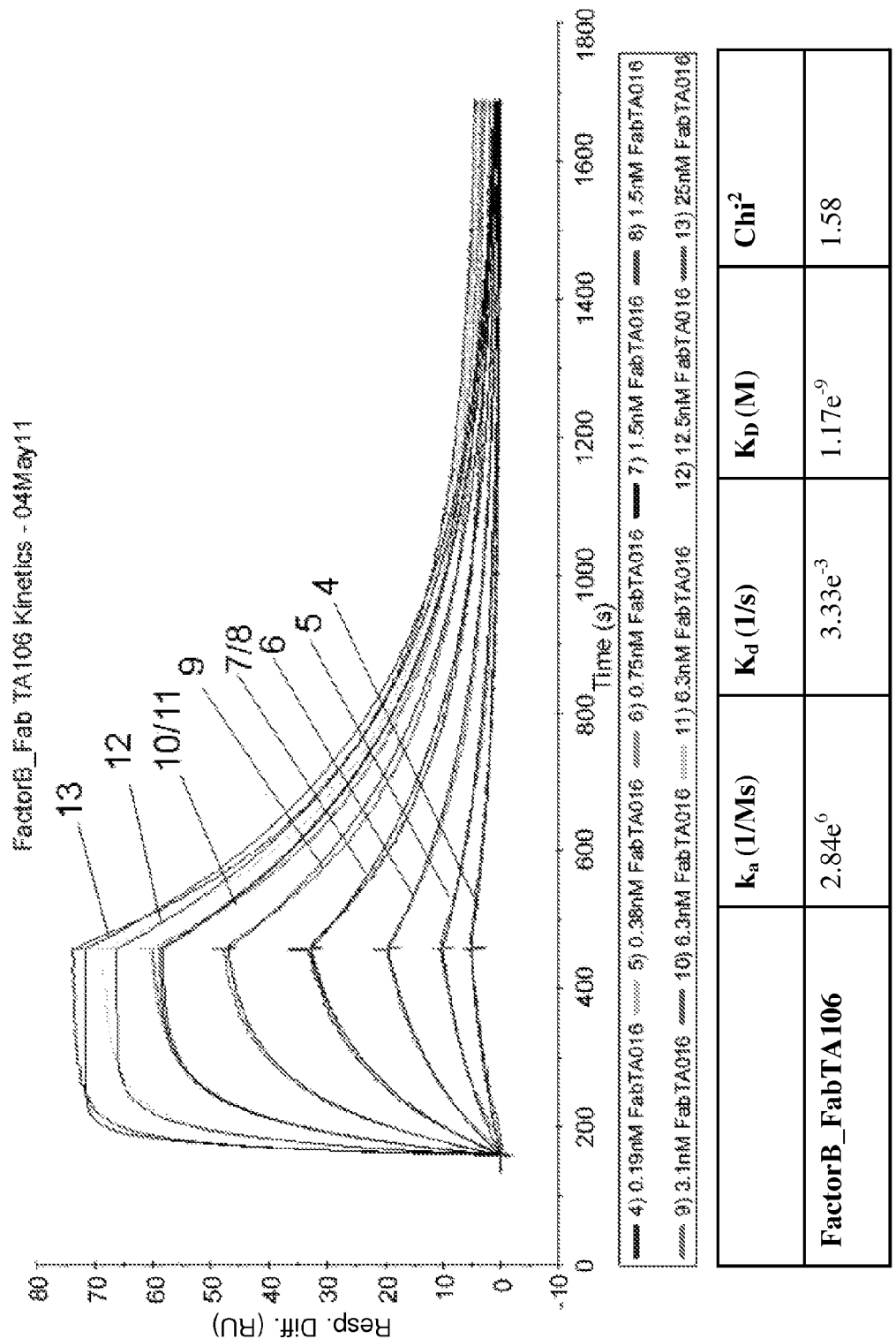
FIG. 24 shows the kinetics of free TA106 wild type Fab binding to captured factor B using the Surface Plasmon Resonance (SPR) analysis. Four to thirteen represent different experimental data with TA106 Fab concentrations of 0.19, 0.38, 0.75, 1.5, 3.1, 6.3, 12.5, and 25 nM, respectively.

Binding kinetics of TA106 Fab and variant S33A Fab (CLS016) were further characterized using Surface Plasmon Resonance (SPR) technology. In one exemplary experiment, both Fabs were captured on chips of a BIACORE™ 3000 analyzer and samples of human factor B of different concentrations were flowed as the antigen over the surface to model soluble human factor B binding, using protocols recommended by the manufacturer and described previously in the instant disclosure. As depicted in FIGS. 21 and 22, the affinities were determined to be approximately 32.8 nM for CLS016 (S33A Fab) and 30.6 nM for TA106 Fab (using only concentrations of 3.1-100 nM for data processing). The affinity of 30.6 nM obtained for Fab TA106 was comparable to that obtained in the initial screening (24.9 nM). In another exemplary experiment, the affinities of both Fabs were also measured by reversing the orientation of the previous experiment. Specifically, human factor B was directly coupled to one flow cell of a CM5 chip. The second flow cell was used as a blank reference with no coupled ligand. CLS016 or TA106 Fab was then flowed on both flow cells. Concentrations between 0.19 to 25 nM were run with duplicates. The surface was regenerated between each cycle. As depicted in FIGS. 23 and 24, the affinities were determined to be approximately 3.4 nM for CLS016 and 1.2 nM for TA106 Fab.

TABLE 3

Binding kinetics of TA106 Fab and TA106 variant S33A Fab

| Sample ID | Conc. (nM) | sensor | Response | KD (M) | kon (1/M s) | kdis (1/s) |
|---|---|---|---|---|---|---|
| CLS016 | 100 | A4 | 2.6066 | 1.30E−08 | 3.38E+05 | 4.38E−03 |
| CLS016 | 50 | B4 | 2.4585 | 2.15E−08 | 1.92E+05 | 4.12E−03 |
| CLS016 | 25 | C4 | 2.3816 | 2.22E−08 | 1.77E+05 | 3.92E−03 |
| CLS016 | 12.5 | D4 | 2.2616 | 3.14E−08 | 1.12E+05 | 3.53E−03 |
| CLS016 | 6.25 | E4 | 2.1352 | 4.19E−08 | 7.69E+04 | 3.22E−03 |
| CLS016 | 3.13 | F4 | 2.1055 | 2.80E−08 | 8.73E+04 | 2.44E−03 |
| CLS016 | 0 | G4 | 2.0273 | | | 6.67E−03 |
| TA106 | 100 | A7 | 2.5536 | 1.30E−08 | 3.12E+05 | 4.05E−03 |

TABLE 3-continued

Binding kinetics of TA106 Fab and TA106 variant S33A Fab

| Sample ID | Conc. (nM) | sensor | Response | KD (M) | kon (1/M s) | kdis (1/s) |
| --- | --- | --- | --- | --- | --- | --- |
| TA106 | 50 | B7 | 2.3939 | 2.27E−08 | 1.72E+05 | 3.90E−03 |
| TA106 | 25 | C7 | 2.3091 | 2.24E−08 | 1.57E+05 | 3.52E−03 |
| TA106 | 12.5 | D7 | 2.2102 | 2.98E−08 | 1.09E+05 | 3.24E−03 |
| TA106 | 6.25 | E7 | 2.0599 | 4.16E−08 | 7.06E+04 | 2.94E−03 |
| TA106 | 3.13 | F7 | 1.995 | 3.23E−08 | 7.40E+04 | 2.39E−03 |
| TA106 | 0 | G7 | 2.0074 | | | 1.79E−03 |

Figure 25:
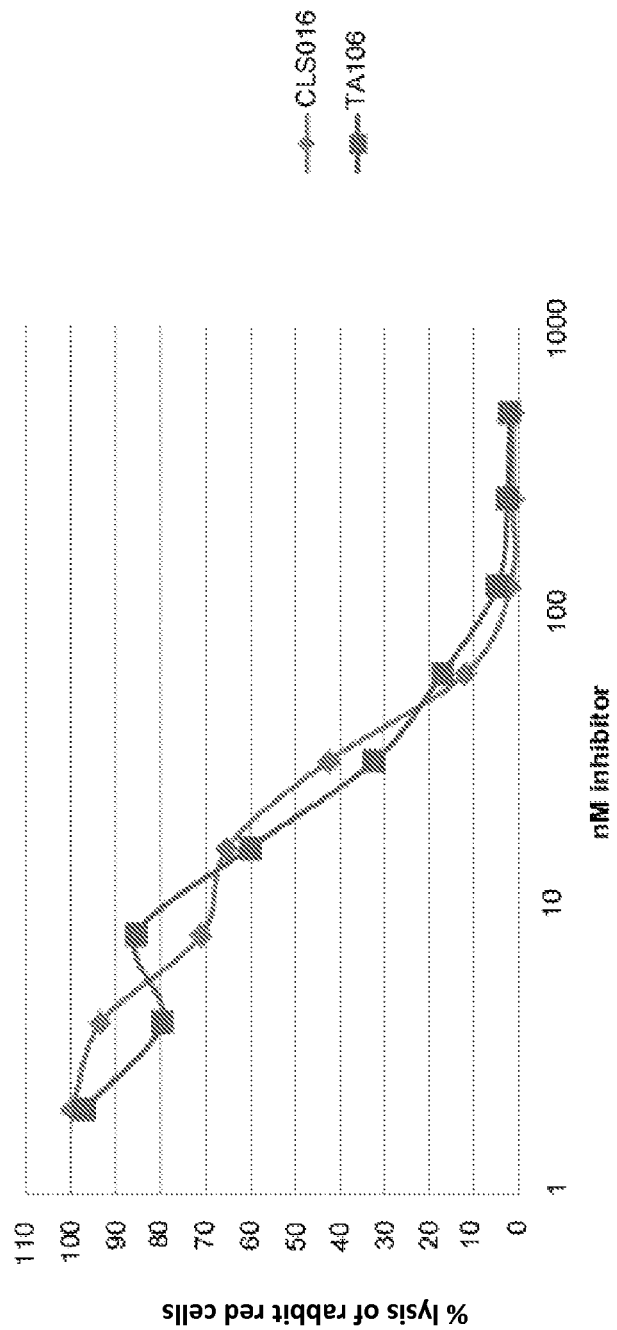
FIG. 25 shows antagonism of hemolysis of rabbit red blood cells in 10% normal human serum of TA106 Fab and TA106-derivative S33A Fab.

An in vitro alternative pathway functional assay (red blood cell hemolytic assay) was performed to compare the antagonism of hemolysis of wild type and S33A Fabs. The protocol for red blood cell hemolytic assay is well-known in the art and in one exemplary experiment, rabbit red blood cells were incubated with 10% normal human serum and Fabs in different concentrations for 10 minutes before calculating the percentage of cell lysis. The average results from duplicate experiments were calculated and compared. As shown in FIG. 25, TA106 wild type and variant S33A Fabs had comparable antagonism of hemolysis.

A summary of characterizations of TA106 variant Fabs is listed in the following Table 4:

TABLE 4

Summary of TA106 Fab and TA106 variant S33A Fab

| Sample | Apparent Molecular Weight (Agilent) | SPR $K_D$ | BLI (octet) $K_D$ | Intact Molecular Weight | In vitro function |
| --- | --- | --- | --- | --- | --- |
| CLS016 | 47.9 kDa | 2.6 nM (factor B on surface) | ~20-30 nM (binding to factor B) | As expected | ~20 nM for 50% hemolysis |
| TA106 Fab | 51.7 kDa | 1.5 nM (factor B on surface) | 20-30 nM (binding to factor B) | As expected | ~20 nM for 50% hemolysis |

Example 2

Formulations, Compositions, and Methods

One aspect of the present invention generally relates to compositions and methods for selectively inhibiting activation of the alternative complement pathway in an animal that has, or is at risk of developing, a condition or disease in which activation of the alternative complement pathway contributes to the condition or disease, exacerbates at least one symptom of the condition or disease, or causes the condition or disease.

Any of the methods of the present invention can be used in any animal, and particularly, in any animal of the vertebrate class Mammalia (i.e., mammals), including, without limitation, primates, rodents, livestock and domestic pets. Preferred mammals to treat with the methods of the present invention are humans.

We claim:

1. A humaneered anti-factor B antibody or antigen-binding fragment thereof that selectively binds to factor B within the third short consensus repeat ("SCR") domain and prevents formation of the C3bBb complex, wherein the humaneered anti-factor B antibody or antigen-binding fragment thereof has an equilibrium dissociation constant ("$K_D$") between about $1.0 \times 10^{-8}$ M and about $1.0 \times 10^{-10}$ M, wherein the humaneered anti-factor B antibody or antigen-binding fragment thereof lacks a glycosylation site in its light chain and exhibits comparable or higher binding affinity relative to an unmodified humaneered anti-factor B antibody or antigen-binding fragment thereof, and wherein the humaneered anti-factor B antibody or antigen-binding fragment thereof comprises:

i) the $V_K$ domain sequence of SEQ ID NO: 3 and the $V_H$ domain sequence of SEQ ID NO: 5 or 4;

ii) the light chain sequence of SEQ ID NO: 8 and the heavy chain sequence of SEQ ID NO: 10 or 9;

iii) the $V_K$ domain sequence of SEQ ID NO: 2 and the $V_H$ domain sequence of SEQ ID NO: 5 or 4; or iv) the light chain sequence SEQ ID NO: 7 and the heavy chain sequence SEQ ID NO: 10 or 9.

2. The humaneered anti-factor B antibody or antigen-binding fragment thereof of claim 1, wherein the antibody or antigen-binding fragment thereof comprises the $V_K$ domain sequence of SEQ ID NO: 2 and the $V_H$ domain sequence selected from SEQ ID NOs: 5 and 4.

3. The humaneered anti-factor B antibody or antigen-binding fragment thereof of claim 1, wherein the antibody or antigen-binding fragment thereof comprises the light chain sequence of SEQ ID NO: 7 and the heavy chain sequence selected from SEQ ID NOs: 10 and 9.

4. The humaneered anti-factor B antibody or antigen-binding fragment thereof of claim 1, wherein the antibody or antigen-binding fragment thereof comprises the $V_K$ domain sequence of SEQ ID NO: 3 and the $V_H$ domain sequence selected from SEQ ID NOs: 5 and 4.

5. The humaneered anti-factor B antibody or antigen-binding fragment thereof of claim 1, wherein the antibody or antigen-binding fragment thereof comprises the light chain sequence of SEQ ID NO: 8 and the heavy chain sequence selected from SEQ ID NOs: 10 and 9.

6. A method of treating a disease or disorder involving activation of the alternative complement pathway, comprising administering the humaneered anti-factor B antibody or antigen-binding fragment thereof of claim 1 to a mammal that has said disease or disorder.

7. The method of claim 6, wherein the disease or disorder is airway hyperresponsiveness ("AHR") or airway inflammation.

8. The method of claim 7, wherein the humaneered anti-factor B antibody or antigen-binding fragment thereof is administered to the individual in an amount effective to reduce AHR or airway inflammation in the mammal as compared to before administration of the antibody or antigen-binding fragment thereof.

9. The method of claim 7, wherein said AHR or airway inflammation is associated with a disease selected from the group consisting of asthma, chronic obstructive pulmonary disease ("COPD"), allergic bronchopulmonary aspergillosis, hypersensitivity pneumonia, eosinophilic pneumonia, emphysema, bronchitis, allergic bronchitis bronchiectasis, cystic fibrosis, tuberculosis, hypersensitivity pneumonitis, occupational asthma, sarcoid disease, reactive airway disease syndrome, interstitial lung disease, hyper-eosinophilic syndrome, rhinitis, sinusitis, exercise-induced asthma, pollution-induced asthma, cough variant asthma, parasitic lung disease, respiratory syncytial virus ("RSV") infection, parainfluenza virus ("PIV") infection, rhinovirus ("RV") infection, and adenovirus infection.

10. The method of claim 7, wherein the AHR or airway inflammation is associated with allergic inflammation.

11. The method of claim 7, wherein the AHR or airway inflammation is associated with asthma.

12. The method of claim 7, wherein the AHR or airway inflammation is associated with COPD.

13. A method of inhibiting activation of the alternative complement pathway in a mammal that has a condition or disease in which activation of the alternative complement pathway contributes to the condition or disease, exacerbates at least one symptom of the condition or disease, or causes the condition or disease, comprising administering the humaneered anti-factor B antibody or antigen-binding fragment thereof of claim 1 to said mammal.

14. A fusion protein comprising the humaneered anti-factor B antibody or antigen-binding fragment thereof of claim 1 and another agent.

15. A pharmaceutical composition comprising an effective amount of the humaneered anti-factor B antibody or antigen-binding fragment thereof of claim 1, and a pharmaceutically acceptable carrier.

16. The method of claim 6, wherein the mammal is a human.

17. The method of claim 13, wherein the mammal is a human.

18. The method of claim 13, wherein the humaneered anti-factor B antibody or antigen-binding fragment thereof reduces C3bBb complex formation in the mammal.

* * * * *